(12) United States Patent
Chorev et al.

(10) Patent No.: US 11,866,506 B2
(45) Date of Patent: Jan. 9, 2024

(54) ANTI-CD59 ANTIBODIES

(71) Applicant: Mellitus, LLC, Boston, MA (US)

(72) Inventors: Michael Chorev, Chestnut Hill, MA (US); Jose A. Halperin, Brookline, MA (US)

(73) Assignee: Mellitus, LLC, Boston, MA (US)

( * ) Notice: Subject to any disclaimer, the term of this patent is extended or adjusted under 35 U.S.C. 154(b) by 647 days.

(21) Appl. No.: 16/606,887

(22) PCT Filed: Apr. 17, 2018

(86) PCT No.: PCT/US2018/027856
§ 371 (c)(1),
(2) Date: Oct. 21, 2019

(87) PCT Pub. No.: WO2018/195008
PCT Pub. Date: Oct. 25, 2018

(65) Prior Publication Data
US 2021/0284751 A1  Sep. 16, 2021

Related U.S. Application Data

(60) Provisional application No. 62/488,346, filed on Apr. 21, 2017.

(51) Int. Cl.
*C07K 16/18* (2006.01)
*C07K 16/28* (2006.01)
*G01N 33/68* (2006.01)

(52) U.S. Cl.
CPC ..... *C07K 16/2896* (2013.01); *G01N 33/6893* (2013.01); *C07K 2317/34* (2013.01); *C07K 2317/56* (2013.01); *C07K 2317/565* (2013.01); *G01N 2800/042* (2013.01)

(58) Field of Classification Search
None
See application file for complete search history.

(56) References Cited

U.S. PATENT DOCUMENTS

| | | | |
|---|---|---|---|
| 4,208,479 A | 6/1980 | Maggio | |
| 4,485,045 A | 11/1984 | Regen | |
| 4,544,545 A | 10/1985 | Ryan et al. | |
| 4,950,712 A | 8/1990 | Didier | |
| 5,013,556 A | 5/1991 | Woodle et al. | |
| 5,208,020 A | 5/1993 | Chari et al. | |
| 5,248,832 A | 9/1993 | Lee | |
| 5,475,092 A | 12/1995 | Chari et al. | |
| 5,478,741 A | 12/1995 | Maret | |
| 5,585,499 A | 12/1996 | Chari et al. | |
| 5,591,828 A | 1/1997 | Bosslet et al. | |
| 5,670,377 A | 9/1997 | Peterson | |
| 5,846,545 A | 12/1998 | Chari et al. | |
| 6,348,584 B1 | 2/2002 | Hodgson et al. | |
| 6,673,901 B2 | 1/2004 | Koide | |
| 6,835,545 B2 | 12/2004 | Halperin | |
| 7,049,082 B2 | 5/2006 | Halperin | |
| 7,439,330 B2 | 10/2008 | Halperin | |
| 7,767,791 B2 | 8/2010 | Halperin | |
| 8,298,779 B2 | 10/2012 | Halperin | |
| 8,404,451 B2 | 3/2013 | Halperin | |
| 9,068,006 B2 | 6/2015 | Halperin | |
| 9,417,248 B2 | 8/2016 | Chorev | |
| 2004/0166531 A1 | 8/2004 | Halperin | |
| 2004/0213761 A1 | 10/2004 | Bowman et al. | |
| 2005/0032128 A1 | 2/2005 | Halperin | |
| 2006/0246524 A1 | 11/2006 | Bauer | |
| 2006/0257936 A1 | 11/2006 | Halperin | |
| 2007/0122404 A1 | 5/2007 | O'Keefe | |
| 2008/0081038 A1 | 4/2008 | Cho | |
| 2008/0267980 A1 | 10/2008 | Tomlinson | |
| 2008/0292639 A1 | 11/2008 | Shen et al. | |
| 2009/0023157 A1 | 1/2009 | Lee | |
| 2009/0028884 A1 | 1/2009 | Schwabe | |
| 2009/0162875 A1 | 6/2009 | Dattwyler | |
| 2009/0269840 A1 | 10/2009 | Popplewell et al. | |
| 2009/0280116 A1 | 11/2009 | Smith et al. | |
| 2010/0150914 A1 | 6/2010 | Wang et al. | |
| 2010/0260783 A1 | 10/2010 | Matsubara et al. | |
| 2010/0331200 A1 | 12/2010 | Gordon | |
| 2013/0189711 A1 | 7/2013 | Halperin | |
| 2014/0227294 A1 | 8/2014 | Anderson et al. | |
| 2014/0322723 A1 | 10/2014 | Halperin | |
| 2015/0284455 A1 | 10/2015 | Springer et al. | |
| 2015/0315286 A1 | 11/2015 | Halperin | |
| 2016/0299150 A1 | 10/2016 | Chorev et al. | |

(Continued)

FOREIGN PATENT DOCUMENTS

| | | |
|---|---|---|
| EP | 2348050 | 10/2017 |
| WO | WO1993011161 | 6/1993 |

(Continued)

OTHER PUBLICATIONS

Rudikoff, S., et al. P.N.A.S.;79:1979-1983 (Year: 1982).*
Rudikoff, Stuart et al. : "Single Amino Acid Substitution Altering Antigen-Binding Specificity", Proceedings of the National Academy of Sciences, National Academy of Sciences, vol. 79, pp. 1979-1983. Mar. 1, 1982.
Al-Lazikani et al., "Standard conformations for the canonical structures of immunoglobulins," J. Mol. Biol., Nov. 1997, 273(4):927-948.
Altschul et al., "Basic local alignment search tool," J. Mol. Biol., Oct. 5, 1990, 215(3):403-410.

(Continued)

*Primary Examiner* — G. R. Ewoldt
(74) *Attorney, Agent, or Firm* — Fish & Richardson P.C.

(57) ABSTRACT

Anti-CD59 and anti-glycated CD59 antibodies are disclosed. Assays, diagnostics, kits, and assay components including such antibodies are provided. Methods for the assessment of diabetes-related indications are included as well as inhibitors of CD59 glycation and methods of evaluating such inhibitors.

16 Claims, 3 Drawing Sheets

Specification includes a Sequence Listing.

(56) References Cited

U.S. PATENT DOCUMENTS

| | | | |
|---|---|---|---|
| 2017/0023589 | A1 | 1/2017 | Chorev |
| 2017/0073431 | A1 | 3/2017 | Marasco et al. |
| 2017/0108505 | A2 | 4/2017 | Chorev |
| 2017/0199201 | A2 | 7/2017 | Chorev |

FOREIGN PATENT DOCUMENTS

| | | | |
|---|---|---|---|
| WO | 2004045520 | A2 | 6/2004 |
| WO | 2005037989 | A2 | 4/2005 |
| WO | 2006009533 | A1 | 1/2006 |
| WO | 2006009533 | A1 | 1/2006 |
| WO | 2008137165 | A1 | 11/2008 |
| WO | 2008137165 | A1 | 11/2008 |
| WO | 2012027555 | A2 | 3/2012 |
| WO | 2012109538 | A2 | 8/2012 |
| WO | 2013008098 | A1 | 1/2013 |
| WO | 2015084994 | A1 | 6/2015 |
| WO | 2018195008 | A1 | 10/2018 |

OTHER PUBLICATIONS

American Diabetes Association, "Diagnosis and Classification of Diabetes Mellitus," Diabetes Care, Mar. 2010, 31(Suppl. 1):S62-S67.

Benoit et al., "Synthesis of Folate-Functionalized RAFT Polymers for Targeted siRNA Delivery," Biomacromolecules, 2011, 12(7):2708-2714.

Bjorge et al., "Relation of Height and Body Mass Index to Renal Cell Carcinoma in Two Million Norwegian Men and Women," Am. J. Epid., Dec. 15, 2004, 160(12):1168-1176.

Carrillo et al., "The Multiple Sequence Alignment Problem in Biology," SIAM J Applied Math., 1988, 48(5):1073-1082.

Chao et al., "Isolating and engineering human antibodies using yeast surface display," Nat. Protoc., Jul. 13, 2006, 1(2):755-768, 15 pages.

Chothia et al., "Canonical structures for the hypervariable regions of immunoglobulins," J. Mol. Biol., Aug. 20, 1987, 196(4):901-917.

Chothia et al., "Conformations of immunoglobulin hypervariable regions," Nature, Dec. 28, 1989, 342:877-883.

Davies et al., "CD59, an LY-6-like protein expressed in human lymphoid cells, regulates the action of the complement membrane attack complex on homologous cells," J. Exp. Med., Sep. 1, 1989, 170(3):637-654.

Davis, "Evidence of RNAi in humans from systemically administered siRNA via targeted nanoparticles," Nature, Mar. 21, 2010, 464:1067-1070, 5 pages.

Davis, "The First Targeted Delivery of siRNA in Humans via a Self-Assembling, Cyclodextrin Polymer-Based Nanoparticle: From Concept to Clinic," Mol. Pharm., 2009, 6(3):659-668.

Delpierre et al., "Fructosamine 3-kinase is involved in an intracellular deglycation pathway in human erythrocytes," Biochem J., Aug. 1, 2002, 365(3):801-808.

Devereux et al., "A comprehensive set of sequence analysis programs for the VAX," Nucleic Acids Research, Jan. 11, 1984, 12(1):387-395.

Dunn, "Dr Priscilla White (1900-1989) of Boston and pregnancy diabetes," Arch. Dis. Child. Fetal Neonatal Ed., May 2004, 89(3): F276-F278.

Edwards et al., "The Remarkable Flexibility of the Human Antibody Repertoire; Isolation of Over One Thousand Different Antibodies to a Single Protein, BLyS," J. Mol. Biol., Nov. 14, 2003, 334(1):103-118.

Eppstein et al., "Biological activity of liposome-encapsulated murine interferon gamma is mediated by a cell membrane receptor," Proc. Natl. Acad. Sci. USA, Jun. 1, 1985, 82(11):3688-3692.

Feig et al., "Preeclampsia as a Risk Factor for Diabetes: A Population-Based Cohort Study," PLoS Med., Apr. 16, 2013, 10(4):e1001425, 8 pages.

Hollinger et al., "Diabodies": Small bivalent and bispecific antibody fragments, Proc. Natl. Acad. Sci. USA, Jul. 15, 1993, 90(14):6444-6448.

Honegger et al., "Yet Another Numbering Scheme for Immunoglobulin Variable Domains: An Automatic Modeling and Analysis Tool," J. Mol. Biol., Jun. 8, 2001, 309(3):657-670.

Hwang et al., "Hepatic uptake and degradation of unilamellar sphingomyelin/cholesterol liposomes: a kinetic study," Proc. Natl, Acad, Sci, USA, Jul. 1, 1980, 77(7):4030-4034.

Johansen et al., "Analysis and prediction of mammalian protein glycation," Glycobiol., Jun. 8, 2006, 16(9):844-853.

Johnson et al., "Kabat Database and its applications: 30 years after the first variability plot," Nucleic Acids Res., Jan. 1, 2000, 28(1):214-218.

Kim et al., "Racial/ethnic differences in the percentage of gestational diabetes mellitus cases attributable to overweight and obesity," Prev. Chronic Dis., Apr. 19, 2012, 9:E88, 15 pages.

Lefranc, "IMGT, the international ImMunoGeneTics information system®: a standardized approach for immunogenetics and immunoinformatics," Immunome Res., Sep. 20, 2005, 1:3, 11 pages.

Li et al., "Utilization of Ig heavy chain variable, diversity, and joining gene segments in children with B-lineage acute lymphoblastic leukemia: implications for the mechanisms of VDJ recombination and for pathogenesis," Blood, Jun. 15, 2004, 103(12):4602-4609.

Ma et al., "Relationship Between Leg Length and Gestational Diabetes Mellitus in Chinese Pregnant Women," Diabetes Care, Nov. 2007, 30(11):2960-2961.

Martin et al., "Irreversible coupling of immunoglobulin fragments to preformed vesicles. An improved method for liposome targeting," J. Biol. Chem., Jan. 10, 1982, 257(1):286-288.

Marvin et al., "Recombinant approaches to IgG-like bispecific antibodies," Acta Pharmacologica Sinica, Jun. 2005, 26(6):649-658.

Massignani et al., "Cellular delivery of antibodies: effective targeted subcellular imaging and new therapeutic tool," Nature Proceedings, May 10, 2010, 17 pages.

Matsuda et al., "The Complete Nucleotide Sequence of the Human Immunoglobulin Heavy Chain Variable Region Locus," J. Exp. Med., 1998, 188(11); 2151-2162.

McCafferty et al., "Phage antibodies: filamentous phage displaying antibody variable domains," Nature, Dec. 6, 1990, 348:552-554.

McGill et al., "Circulating 1,5-Anhydroglucitol Levels in Adult Patients With Diabetes Reflect Longitudinal Changes of Glycemia," Diabetes Care, Aug. 2004, 27(8):1859-1865.

medlineplus.gov, "Gestational Diabetes," Medical Encyclopedia, available on or before Jun. 17, 2001, retrieved on Oct. 20, 2021, retrieved from URL <http://www.nlm.nih.gov/medlineplus/ency/article/000896.htm>, 5 pages.

Metzger et al., "International association of diabetes and pregnancy study groups recommendations on the diagnosis and classification of hyperglycemia in pregnancy," Diabetes Care, Mar. 2010, 33(3):676-682.

Meyers et al., "Optimal alignments in linear space," CABIOS, Mar. 1, 1989, 4(1):11-17.

Najafian et al., "Occurrence of Fetal Macrosomia Rate and Its Maternal and Neonatal Complications: A 5-Year Cohort Study," ISRN Obstetrics and Gynecology, 2012, 2012:353791, 6 pages.

Nelson, "Antibody fragments: hope and hype," mAbs, Jan.-Feb. 2010, 2(1):77-83.

Nikoloudis et al., "A complete, multi-level conformational clustering of antibody complementarity-determining regions," PeerJ, Jul. 1, 2014, 2:e456, 40 pages.

Okun et al., "Gestational diabetes mellitus. Unresolved issues and future research directions.," Can. Fam. Physician, Jan. 1997, 43:88-93.

Oliva et al., "An automated classification of the structure of protein loops," J. Mol. Biol., Mar. 7, 1997, 266(4):814-830.

Panowski et al., "Site-specific antibody drug conjugates for cancer therapy," mAbs, Jan.-Feb. 2014, 6:1, 34-45.

Pershad et al., "Generating a panel of highly specific antibodies to 20 human SH2 domains by phage display," Protein Engineering Design and Selection, Feb. 17, 2010, 23:279-288.

Pitella et al., "Enhanced endosomal escape of siRNA-incorporating hybrid nanoparticles from calcium phosphate and PEG-block charge-conversional polymer for efficient gene knockdown with negligible cytotoxicity," Biomaterials, Apr. 2011, 32(11):3106-3114.

(56) References Cited

OTHER PUBLICATIONS

Riethmuller, "Symmetry breaking: bispecific antibodies, the beginnings, and 50 years on,"Cancer Immunity, 2012, 12:12-18, 7 pages.
Rodger, "Insulin-dependent (type I) diabetes mellitus," CMAJ, Nov. 15, 1991, 145(10):1227-1237.
Rodger, "Non-insulin-dependent (type II) diabetes mellitus," CMAJ, Dec. 15, 1991, 145(12):1571-1581.
Ross, "Gestational diabetes," Australian Family Physician, Jun. 2006, 35(6):392-396.
Rozema et al., "Dynamic PolyConjugates for targeted in vivo delivery of siRNA to hepatocytes," Proc. Natl. Acad. Sci. USA, Aug. 7, 2007, 104:12982-12987.
Schaefer et al., "Immunoglobulin domain crossover as a generic approach for the production of bispecific IgG antibodies," Proc. Natl. Acad. Sci. USA, 2011, 108(27):11187-11192.
Schofield et al., "Application of phage display to high throughput antibody generation and characterization," Genome Biol., Nov. 29, 2007, 8:R254, 18 pages.
Sherwood et al., "Controlled Antibody Delivery Systems," Nature Biotechnology, Nov. 1, 1992, 10:1446-1449.
Siegwart et al., "Combinatorial synthesis of chemically diverse core-shell nanoparticles for intracellular delivery," Proc. Natl. Acad. Sci. USA, Aug. 9, 2011, 108:12996-13001.
Ukita et al., "Urinary excretion of glycated protein determined with a specific radioimmunoassay," Clin. Chem., Apr. 1, 1991, 37(4):504-507.
Wu et al., "An Analysis of the Sequences of the Variable Regions of Bence Jones Porteins and Myeloma Light Chains and Their Implications for Antibody Complementarity," J. Exp. Med., Aug. 1, 1970, 132(2):211-250.
Yessoufou et al., "Maternal Diabetes in Pregnancy: Early and Long-Term Outcomes on the Offspring and the Concept of "Metabolic Memory"," Experimental Diabetes Research, Nov. 21, 2011, 2011(218598):1-12.
"I. Properties," Sodium Borohydride Digest. John Yamamoto, Rohm and Haas Compamy, 6-13 (2003).
"Product Specification for Sodium borohydride solution—0.5 M in 2-methoxyethyl ether," Sigma-Aldrich (1 page).
Acosta et al. "Molecular basis for a link between complement and the vascular complications of diabetes" Proc Natl Acad Sci U SA. 97(10):5450-5 (2000).
Ghosh et al. "A Specific And Sensitive Assay For Blood Levels of Glycated Cd59: A Novel Biomarker For Diabetes," available in PMC Aug. 1, 2014, published in final edited form as: Am J Hematol. 88(8): 670-676 (2014) (15 pages).
Ghosh et al.,"Plasma Glycated CD59, a Novel Biomarker for Detection of Pregnancy-Induced Glucose Intolerance," Diabetes Care, vol. 40 (2017) (4 pages).
Petranka et al.,"Structure-function relationships of the complement regulatory portein, CD59," Blood Cells Mol Dis., 1996, vol. 22, No. 3, pp. 281-296.
Qin et al., "Glycation Inactivation of the Complement Regulatory Protein CD59," Diabetes. 53(10): 2653-2661 (2004).

* cited by examiner

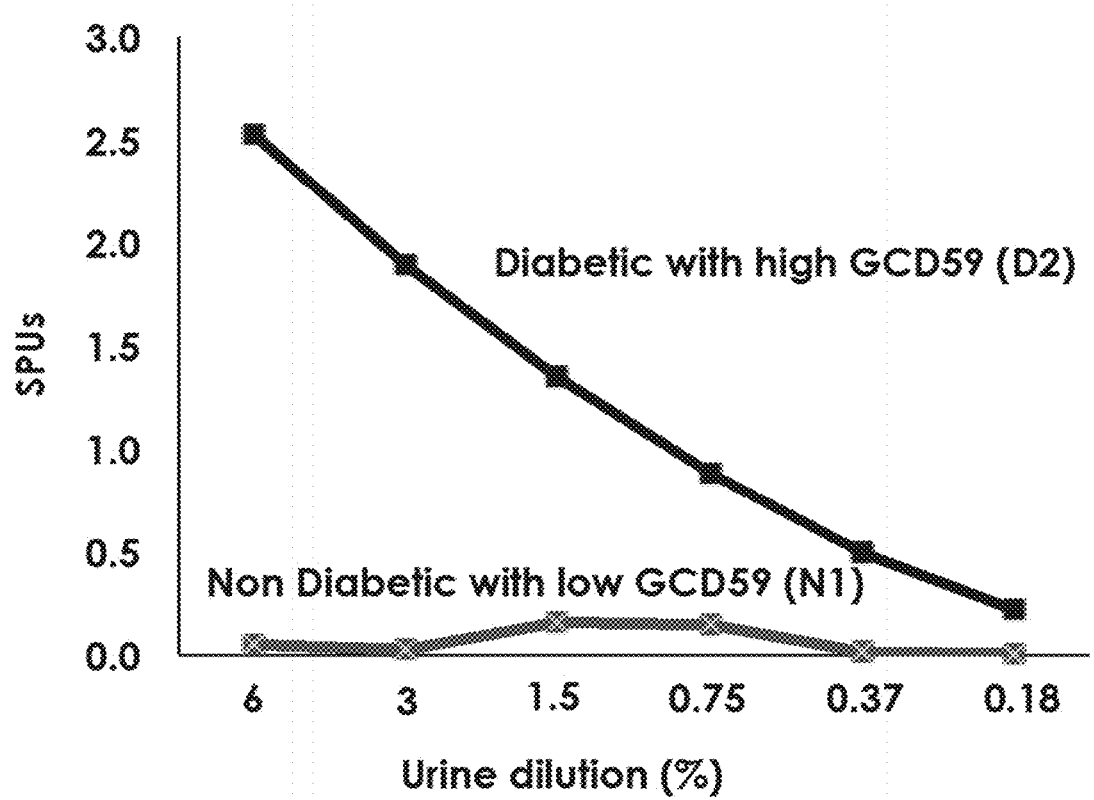

SEQUENCE LISTING

```
<160> NUMBER OF SEQ ID NOS: 57

<210> SEQ ID NO 1
<211> LENGTH: 77
<212> TYPE: PRT
<213> ORGANISM: Homo sapiens

<400> SEQUENCE: 1

Leu Gln Cys Tyr Asn Cys Pro Asn Pro Thr Ala Asp Cys Lys Thr Ala
1               5                   10                  15

Val Asn Cys Ser Ser Asp Phe Asp Ala Cys Leu Ile Thr Lys Ala Gly
            20                  25                  30

Leu Gln Val Tyr Asn Lys Cys Trp Lys Phe Glu His Cys Asn Phe Asn
        35                  40                  45

Asp Val Thr Thr Arg Leu Arg Glu Asn Glu Leu Thr Tyr Tyr Cys Cys
    50                  55                  60

Lys Lys Asp Leu Cys Asn Phe Asn Glu Gln Leu Glu Asn
65                  70                  75

<210> SEQ ID NO 2
<211> LENGTH: 238
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met Lys Leu Pro Val Arg Leu Leu Val Leu Met Phe Trp Ile Pro Ala
1               5                   10                  15

Ser Asn Ser Asp Val Leu Met Thr Gln Ile Pro Leu Ser Leu Pro Val
            20                  25                  30

Ser Leu Gly Asp His Ala Ser Ile Ser Cys Arg Ser Ser Gln Asn Ile
        35                  40                  45

Val Tyr Ser Asp Gly Asn Thr Tyr Leu Glu Trp Tyr Leu Gln Lys Pro
    50                  55                  60
```

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Arg Ile Ser Arg Val Glu Ala Glu Asp Leu Gly Val Tyr Tyr Cys
            100                 105                 110

Leu Gln Gly Ser His Val Pro Pro Thr Phe Gly Ser Gly Thr Lys Leu
        115                 120                 125

Glu Ile Lys Arg Ala Asp Ala Ala Pro Thr Val Ser Ile Phe Pro Pro
    130                 135                 140

Ser Ser Glu Gln Leu Thr Ser Gly Gly Ala Ser Val Val Cys Phe Leu
145                 150                 155                 160

Asn Asn Phe Tyr Pro Lys Asp Ile Asn Val Lys Trp Lys Ile Asp Gly
                165                 170                 175

Ser Glu Arg Gln Asn Gly Val Leu Asn Ser Trp Thr Asp Gln Asp Ser
            180                 185                 190

Lys Asp Ser Thr Tyr Ser Met Ser Ser Thr Leu Thr Leu Thr Lys Asp
        195                 200                 205

Glu Tyr Glu Arg His Asn Ser Tyr Thr Cys Glu Ala Thr His Lys Thr
    210                 215                 220

Ser Thr Ser Pro Ile Val Lys Ser Phe Asn Arg Asn Glu Cys
225                 230                 235

<210> SEQ ID NO 3
<211> LENGTH: 462
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Met Gly Trp Ser Cys Ile Ile Leu Phe Leu Val Ala Thr Ala Thr Gly
1               5                   10                  15

Val His Ser Gln Val Gln Leu Gln Gln Pro Gly Ala Glu Leu Val Arg
            20                  25                  30

Pro Gly Ala Ser Val Lys Leu Ser Cys Lys Ala Ser Gly Tyr Thr Phe
        35                  40                  45

Thr Ser Tyr Trp Ile Asn Trp Val Lys Gln Arg Pro Gly Gln Gly Leu
    50                  55                  60

Glu Trp Ile Gly Asn Ile Tyr Pro Ser Asp Ser Tyr Thr Asn Tyr Asn
65                  70                  75                  80

Gln Lys Phe Lys Asp Lys Ala Thr Leu Thr Val Asp Lys Ser Ser Ser
                85                  90                  95

Thr Ala Tyr Met Gln Leu Ser Ser Pro Thr Ser Glu Asp Ser Ala Val
            100                 105                 110

Tyr Tyr Cys Ala Arg Glu Arg Tyr Glu Arg Asp Ala Met Asp Tyr Trp
        115                 120                 125

Gly Gln Gly Thr Ser Val Thr Val Ser Ser Ala Lys Thr Thr Pro Pro
    130                 135                 140

Ser Val Tyr Pro Leu Ala Pro Gly Ser Ala Ala Gln Thr Asn Ser Met
145                 150                 155                 160

Val Thr Leu Gly Cys Leu Val Lys Gly Tyr Phe Pro Glu Pro Val Thr
                165                 170                 175

Val Thr Trp Asn Ser Gly Ser Leu Ser Ser Gly Val His Thr Phe Pro
            180                 185                 190

Ala Val Leu Gln Ser Asp Leu Tyr Thr Leu Ser Ser Val Thr Val
    195                 200                 205

Pro Ser Ser Thr Trp Pro Ser Glu Thr Val Thr Cys Asn Val Ala His
    210                 215                 220

Pro Ala Ser Ser Thr Lys Val Asp Lys Lys Ile Val Pro Arg Asp Cys
225                 230                 235                 240

Gly Cys Lys Pro Cys Ile Cys Thr Val Pro Glu Val Ser Ser Val Phe
                245                 250                 255

Ile Phe Pro Pro Lys Pro Lys Asp Val Leu Thr Ile Thr Leu Thr Pro
            260                 265                 270

Lys Val Thr Cys Val Val Asp Ile Ser Lys Asp Asp Pro Glu Val
    275                 280                 285

Gln Phe Ser Trp Phe Val Asp Asp Val Glu Val His Thr Ala Gln Thr
    290                 295                 300

Gln Pro Arg Glu Glu Gln Phe Asn Ser Thr Phe Arg Ser Val Ser Glu
305                 310                 315                 320

Leu Pro Ile Met His Gln Asp Trp Leu Asn Gly Lys Glu Phe Lys Cys
                325                 330                 335

Arg Val Asn Ser Ala Ala Phe Pro Ala Pro Ile Glu Lys Thr Ile Ser
            340                 345                 350

Lys Thr Lys Gly Arg Pro Lys Ala Pro Gln Val Tyr Thr Ile Pro Pro
    355                 360                 365

Pro Lys Glu Gln Met Ala Lys Asp Lys Val Ser Leu Thr Cys Met Ile
    370                 375                 380

Thr Asp Phe Phe Pro Glu Asp Ile Thr Val Glu Trp Gln Trp Asn Gly
385                 390                 395                 400

Gln Pro Ala Glu Asn Tyr Lys Asn Thr Gln Pro Ile Met Asp Thr Asp
                405                 410                 415

Gly Ser Tyr Phe Val Tyr Ser Lys Leu Asn Val Gln Lys Ser Asn Trp
            420                 425                 430

Glu Ala Gly Asn Thr Phe Thr Cys Ser Val Leu His Glu Gly Leu His
    435                 440                 445

Asn His His Thr Glu Lys Ser Leu Ser His Ser Pro Gly Lys
    450                 455                 460

<210> SEQ ID NO 4
<211> LENGTH: 238
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Met Lys Leu Pro Val Arg Leu Leu Val Leu Met Phe Trp Ile Pro Ala
1               5                   10                  15

Ser Ser Ser Asp Val Val Met Thr Gln Ser Pro Leu Ser Leu Pro Val
                20                  25                  30

Ser Leu Gly Asp Gln Ala Ser Ile Ser Cys Arg Ser Ser Gln Ser Leu
            35                  40                  45

Val His Ser Asn Gly Asn Thr Tyr Leu Gln Trp Tyr Leu Gln Lys Pro
    50                  55                  60

Gly Gln Ser Pro Asn Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr

```
                    85                  90                  95
Leu Lys Ile Ser Arg Val Glu Ala Glu Asp Leu Gly Val Tyr Phe Cys
                100                 105                 110

Ser Gln Ser Thr His Val Pro Phe Thr Phe Gly Ser Gly Thr Lys Leu
                115                 120                 125

Glu Ile Lys Arg Ala Asp Ala Ala Pro Thr Val Ser Ile Phe Pro Pro
            130                 135                 140

Ser Ser Glu Gln Leu Thr Ser Gly Gly Ala Ser Val Val Cys Phe Leu
145                 150                 155                 160

Asn Asn Phe Tyr Pro Lys Asp Ile Asn Val Lys Trp Lys Ile Asp Gly
                165                 170                 175

Ser Glu Arg Gln Asn Gly Val Leu Asn Ser Trp Thr Asp Gln Asp Ser
                180                 185                 190

Lys Asp Ser Thr Tyr Ser Met Ser Ser Thr Leu Thr Leu Thr Lys Asp
                195                 200                 205

Glu Tyr Glu Arg His Asn Ser Tyr Thr Cys Glu Ala Thr His Lys Thr
            210                 215                 220

Ser Thr Ser Pro Ile Val Lys Ser Phe Asn Arg Asn Glu Cys
225                 230                 235

<210> SEQ ID NO 5
<211> LENGTH: 460
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Met Asn Phe Gly Leu Ser Leu Ile Phe Leu Ala Leu Ile Leu Lys Gly
1               5                   10                  15

Val Gln Cys Glu Val Gln Leu Val Glu Ser Gly Gly Asp Leu Val Lys
            20                  25                  30

Pro Gly Gly Ser Leu Lys Leu Ser Cys Ala Ala Ser Gly Phe Thr Phe
        35                  40                  45

Ser Ser Tyr Gly Met Ser Trp Val Arg Gln Ser Pro Asp Lys Arg Met
50                  55                  60

Glu Trp Val Ala Thr Ile Ser Ser Gly Gly Ser Tyr Thr Tyr Tyr Pro
65                  70                  75                  80

Asp Ser Val Lys Gly Arg Phe Thr Val Ser Arg Asp Asn Ala Lys Asn
                85                  90                  95

Thr Leu Tyr Leu Gln Met Ser Ser Leu Arg Ser Glu Asp Thr Ala Ile
            100                 105                 110

Phe Tyr Cys Val Arg Asp Arg Tyr Asp Gly Met Asp Tyr Trp Gly Gln
        115                 120                 125

Gly Thr Ser Val Thr Val Ser Ser Ala Lys Thr Thr Pro Pro Ser Val
130                 135                 140

Tyr Pro Leu Ala Pro Gly Ser Ala Ala Gln Thr Asn Ser Met Val Thr
145                 150                 155                 160

Leu Gly Cys Leu Val Lys Gly Tyr Phe Pro Glu Pro Val Thr Val Thr
                165                 170                 175

Trp Asn Ser Gly Ser Leu Ser Ser Gly Val His Thr Phe Pro Ala Val
            180                 185                 190

Leu Gln Ser Asp Leu Tyr Thr Leu Ser Ser Ser Val Thr Val Pro Ser
        195                 200                 205
```

Ser Thr Trp Pro Ser Glu Thr Val Thr Cys Asn Val Ala His Pro Ala
210                 215                 220

Ser Ser Thr Lys Val Asp Lys Lys Ile Val Pro Arg Asp Cys Gly Cys
225                 230                 235                 240

Lys Pro Cys Ile Cys Thr Val Pro Glu Val Ser Ser Val Phe Ile Phe
            245                 250                 255

Pro Pro Lys Pro Lys Asp Val Leu Thr Ile Thr Leu Thr Pro Lys Val
            260                 265                 270

Thr Cys Val Val Val Asp Ile Ser Lys Asp Asp Pro Glu Val Gln Phe
        275                 280                 285

Ser Trp Phe Val Asp Asp Val Glu Val His Thr Ala Gln Thr Gln Pro
290                 295                 300

Arg Glu Glu Gln Phe Asn Ser Thr Phe Arg Ser Val Ser Glu Leu Pro
305                 310                 315                 320

Ile Met His Gln Asp Trp Leu Asn Gly Lys Glu Phe Lys Cys Arg Val
                325                 330                 335

Asn Ser Ala Ala Phe Pro Ala Pro Ile Glu Lys Thr Ile Ser Lys Thr
            340                 345                 350

Lys Gly Arg Pro Lys Ala Pro Gln Val Tyr Thr Ile Pro Pro Pro Lys
        355                 360                 365

Glu Gln Met Ala Lys Asp Lys Val Ser Leu Thr Cys Met Ile Thr Asp
370                 375                 380

Phe Phe Pro Glu Asp Ile Thr Val Glu Trp Gln Trp Asn Gly Gln Pro
385                 390                 395                 400

Ala Glu Asn Tyr Lys Asn Thr Gln Pro Ile Met Asp Thr Asp Gly Ser
                405                 410                 415

Tyr Phe Val Tyr Ser Lys Leu Asn Val Gln Lys Ser Asn Trp Glu Ala
            420                 425                 430

Gly Asn Thr Phe Thr Cys Ser Val Leu His Glu Gly Leu His Asn His
        435                 440                 445

His Thr Glu Lys Ser Leu Ser His Ser Pro Gly Lys
450                 455                 460

<210> SEQ ID NO 6
<211> LENGTH: 718
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6
atgaagttgc ctgttaggct gttggtgctg atgttctgga ttcctgcttc caacagtgat      60
gttttgatga cccaaattcc actctccctg cctgtcagtc ttggagatca cgcctccatc     120
tcttgcagat ctagtcagaa cattgtatat agtgatggaa acacctattt agaatggtac     180
ctgcagaaac caggacagtc tccaaagctc ctgatctaca agtttccaa ccgattttct      240 ggggtcccag acaggttcag tggcagtgga tcagggacag atttcacact caggatcagc     300
agagtggagg ctgaggatct gggagtttat tactgcttgc aaggttcaca tgttcctccc     360
acgttcggct cggggacaaa gttggagata aacggctg atgctgcacc aactgtatcc       420
atcttcccac catccagtga gcagttaaca tctggaggtg cctcagtcgt gtgcttcttg     480
aacaacttct accccaaaga catcaatgtc aagtggaaga ttgatggcag tgaacgacaa     540
aatggcgtcc tgaacagttg gactgatcag gacagcaaag acagcaccta cagcatgagc     600

```
agcaccctca cgttgaccaa ggacgagtat gaacgacata acagctatac ctgtgaggcc      660
actcacaaga catcaacttc acccattgtc aagagcttca acaggaatga gtgttaaa       718
```

<210> SEQ ID NO 7
<211> LENGTH: 1390
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7

```
atgggatgga gctgtatcat cctcttcttg gtagcaacag ctacaggtgt ccactcccag      60
gtccaactgc agcagcctgg ggctgagctg gtgaggcctg ggcttcagt gaaactgtcc      120 tgcaaggctt ctggctacac cttcaccagc tactggataa actgggtgaa gcagaggcct     180
ggacaaggcc ttgagtggat cggaaatatt tatccttctg atagttatac taactacaat     240
caaaagttca aggacaaggc cacattgact gtagacaaat cctccagcac agcctacatg     300
cagctcagca gcccgacatc tgaggactct gcggtctatt actgtgcaag agaaaggtac     360
gaaagggatg ctatggacta ctggggtcaa ggaacctcag tcactgtctc ctcagccaaa     420
acgacacccc catctgtcta tccactggcc cctggatctg ctgcccaaac taactccatg     480
gtgaccctgg gatgcctggt caagggctat ttccctgagc cagtgacagt gacctggaac     540
tctggatccc tgtccagcgg tgtgcacacc ttcccagctg tcctgcagtc tgacctctac     600
actctgagca gctcagtgac tgtccgctcc agcacctggc ccagcgagac cgtcacctgc     660
aacgttgccc acccggccag cagcaccaag gtggacaaga aaattgtgcc cagggattgt     720
ggttgtaagc cttgcatatg tacagtccca gaagtatcat ctgtcttcat cttcccccca     780
aagcccaagg atgtgctcac cattactctg actcctaagg tcacgtgtgt tgtggtagac     840
atcagcaagg atgatcccga ggtccagttc agctggtttg tagatgatgt ggaggtgcac     900
acagctcaga cgcaaccccg ggaggagcag ttcaacagca ctttccgctc agtcagtgaa     960
cttcccatca tgcaccagga ctggctcaat ggcaaggagt tcaaatgcag ggtcaacagt    1020
gcagctttcc ctgcccccat cgagaaaacc atctccaaaa ccaaaggcag accgaaggct    1080
ccacaggtgt acaccattcc acctcccaag gagcagatgg ccaaggataa agtcagtctg    1140
acctgcatga taacagactt cttccctgaa gacattactg tggagtggca gtggaatggg    1200
cagccagcgg agaactacaa gaacactcag cccatcatgg acacagatgg ctcttacttc    1260
gtctacagca agctcaatgt gcagaagagc aactgggagg caggaaatac tttcacctgc    1320
tctgtgttac atgagggcct gcacaaccac catactgaga agagcctctc ccactctcct    1380
ggtaaataaa                                                          1390
```

<210> SEQ ID NO 8
<211> LENGTH: 1390
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8

```
atgggatgga gctgtatcat cctcttcttg gtagcaacag ctacaggtgt ccactcccag      60
gtccaactgc agcagcctgg ggctgagctg gtgaggcctg ggcttcagt gaaactgtcc      120 tgcaaggctt ctggctacac cttcaccagc tactggataa actgggtgaa gcagaggcct     180
```

```
ggacaaggcc ttgagtggat cggaaatatt tatccttctg atagttatac taactacaat    240
caaaagttca aggacaaggc cacattgact gtagacaaat cctccagcac agcctacatg    300
cagctcagca gcccgacatc tgaggactct gcggtctatt actgtgcaag agaaaggtac    360
gaaagggatg ctatggacta ctggggtcaa ggaacctcag tcactgtctc ctcagccaaa    420
acgacacccc catctgtcta tccactggcc cctggatctg ctgcccaaac taactccatg    480
gtgaccctgg gatgcctggt caagggctat ttccctgagc cagtgacagt gacctggaac    540
tctggatccc tgtccagcgg tgtgcacacc ttcccagctg tcctgcagtc tgacctctac    600
actctgagca gctcagtgac tgtcccctcc agcacctggc ccagcgagac cgtcacctgc    660
aacgttgccc acccggccag cagcaccaag gtggacaaga aaattgtgcc cagggattgt    720
ggttgtaagc cttgcatatg tacagtccca gaagtatcat ctgtcttcat cttccccccca    780 aagcccaagg atgtgctcac cattactctg actcctaagg tcacgtgtgt tgtggtagac    840
atcagcaagg atgatcccga ggtccagttc agctggtttg tagatgatgt ggaggtgcac    900
acagctcaga cgcaaccccg ggaggagcag ttcaacagca ctttccgctc agtcagtgaa    960
cttcccatca tgcaccagga ctggctcaat ggcaaggagt tcaaatgcag ggtcaacagt   1020
gcagctttcc ctgcccccat cgagaaaacc atctccaaaa ccaaaggcag accgaaggct   1080
ccacaggtgt acaccattcc acctcccaag gagcagatgg ccaaggataa agtcagtctg   1140
acctgcatga taacagactt cttccctgaa gacattactg tggagtggca gtggaatggg   1200
cagccagcgg agaactacaa gaacactcag cccatcatgg acacagatgg ctcttacttc   1260
gtctacagca agctcaatgt gcagaagagc aactgggagg caggaaatac tttcacctgc   1320
tctgtgttac atgagggcct gcacaaccac catactgaga gagcctctc ccactctccg   1380 ggtaaataaa                                                           1390

<210> SEQ ID NO 9
<211> LENGTH: 718
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9
atgaagttgc ctgttaggct gttggtgctg atgttctgga ttcctgcttc cagcagtgat     60
gttgtgatga cccaaagtcc actctccctg cctgtcagtc ttggagatca agcctccatc    120
tcttgcagat ctagtcagag ccttgtacac agtaatggaa acacctattt acaatggtac    180
ctgcagaagc caggccagtc tccaaaacctc ctgatctaca agtttccaa ccgatttttct    240 ggggtcccag acaggttcag tggcagtgga tcagggacag atttcacact caagatcagt    300
agagtggagg ctgaggatct gggagtttat ttctgctctc aaagtacaca tgttccattc    360
acgttcggct cggggacaaa gttggaaata aaacggctga tgctgcacc aactgtatcc    420 atcttcccac catccagtga gcagttaaca tctggaggtg cctcagtcgt gtgcttcttg    480
aacaacttct accccaaaga catcaatgtc aagtggaaga ttgatggcag tgaacgacaa    540
aatggcgtcc tgaacagttg gactgatcag gacagcaaag acagcaccta cagcatgagc    600
agcaccctca cgttgaccaa ggacgagtat gaacgacata acagctatac ctgtgaggcc    660
actcacaaga catcaacttc acccattgtc aagagcttca caggaatga gtgttaaa      718
```

<210> SEQ ID NO 10
<211> LENGTH: 1384
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 10

| | | | | | |
|---|---|---|---|---|---|
| atgaacttcg | ggctcagctt | gattttcctt | gccctcattt | taaaaggtgt | ccagtgtgag | 60 |
| gtgcagctgg | tggagtctgg | gggagactta | gtgaagcctg | agggtccct | gaaactctcc | 120 |
| tgtgcagcct | ctggattcac | tttcagtagc | tatggcatgt | cttgggttcg | ccagagtcca | 180 |
| gacaagagga | tggaatgggt | cgcaaccatt | agtagtggtg | gtagttatac | gtattatcca | 240 |
| gacagcgtga | aggggcgatt | caccgtctcc | agagacaatg | ccaagaacac | cctgtacctg | 300 |
| caaatgagca | gtctgaggtc | tgaggacaca | gccatttttt | actgtgtaag | agataggtac | 360 |
| gacggtatgg | actattgggg | tcagggaacc | tcagtcaccg | tctcctcagc | caaaacgaca | 420 |
| cccccatctg | tctatccact | ggcccctgga | tctgctgccc | aaactaactc | catggtgacc | 480 |
| ctgggatgcc | tggtcaaggg | ctatttccct | gagccagtga | cagtgacctg | aactctgga | 540 |
| tccctgtcca | gcggtgtgca | caccttccca | gctgtcctgc | agtctgacct | ctacactctg | 600 |
| agcagctcag | tgactgtccc | ctccagcacc | tgggcccagcg | agaccgtcac | ctgcaacgtt | 660 |
| gcccaccegg | ccagcagcac | caaggtggac | aagaaaattg | tgcccaggga | ttgtggttgt | 720 |
| aagccttgca | tatgtacagt | cccagaagta | tcatctgtct | tcatcttccc | cccaaagccc | 780 |
| aaggatgtgc | tcaccattac | tctgactcct | aaggtcacgt | gtgttgtggt | agacatcagc | 840 |
| aaggatgatc | ccgaggtcca | gttcagctgg | tttgtagatg | atgtggaggt | gcacacagct | 900 |
| cagacgcaac | cccgggagga | gcagttcaac | agcactttcc | gctcagtcag | tgaacttccc | 960 |
| atcatgcacc | aggactggct | caatggcaag | gagttcaaat | gcagggtcaa | cagtgcagct | 1020 |
| ttccctgccc | ccatcgagaa | aaccatctcc | aaaaccaaag | gcagaccgaa | ggctccacag | 1080 |
| gtgtacacca | ttccacctcc | caaggagcag | atggccaagg | ataaagtcag | tctgacctgc | 1140 |
| atgataacag | acttcttccc | tgaagacatt | actgtggagt | ggcagtggaa | tgggcagcca | 1200 |
| gcggagaact | acaagaacac | tcagcccatc | atggacacag | atggctctta | cttcgtctac | 1260 |
| agcaagctca | atgtgcagaa | gagcaactgg | gaggcaggaa | atactttcac | ctgctctgtg | 1320 |
| ttacatgagg | gcctgcacaa | ccaccatact | gagaagagcc | tctcccactc | tcctggtaaa | 1380 |
| taaa | | | | | | 1384 |

<210> SEQ ID NO 11
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 11

Met Lys Leu Pro Val Arg Leu Leu Val Leu Met Phe Trp Ile Pro Ala
1               5                   10                  15

Ser Asn Ser

<210> SEQ ID NO 12
<211> LENGTH: 19
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 12

Met Lys Leu Pro Val Arg Leu Leu Val Leu Met Phe Trp Ile Pro Ala
1               5                   10                  15

Ser Ser Ser

<210> SEQ ID NO 13
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Met Gly Trp Ser Cys Ile Ile Leu Phe Leu Val Ala Thr Ala Thr Gly
1               5                   10                  15

Val His Ser

<210> SEQ ID NO 14
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Met Asn Phe Gly Leu Ser Leu Ile Phe Leu Ala Leu Ile Leu Lys Gly
1               5                   10                  15

Val Gln Cys

<210> SEQ ID NO 15
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Asp Val Leu Met Thr Gln Ile Pro Leu Ser Leu Pro Val Ser Leu Gly
1               5                   10                  15

Asp His Ala Ser Ile Ser Cys Arg Ser Ser
            20                  25

<210> SEQ ID NO 16
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Asp Val Val Met Thr Gln Ser Pro Leu Ser Leu Pro Val Ser Leu Gly
1               5                   10                  15

Asp Gln Ala Ser Ile Ser Cys Arg Ser Ser
            20                  25

<210> SEQ ID NO 17
```

```
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Leu Glu Trp Tyr Leu Gln Lys Pro Gly Gln Ser Pro Lys Leu Leu Ile
1               5                   10                  15

Tyr

<210> SEQ ID NO 18
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Leu Gln Trp Tyr Leu Gln Lys Pro Gly Gln Ser Pro Asn Leu Leu Ile
1               5                   10                  15

Tyr

<210> SEQ ID NO 19
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Asn Arg Phe Ser Gly Val Pro Asp Arg Phe Ser Gly Ser Gly Ser Gly
1               5                   10                  15

Thr Asp Phe Thr Leu Arg Ile Ser Arg Val Glu Ala Glu Asp Leu Gly
            20                  25                  30

Val Tyr Tyr Cys
        35

<210> SEQ ID NO 20
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Asn Arg Phe Ser Gly Val Pro Asp Arg Phe Ser Gly Ser Gly Ser Gly
1               5                   10                  15

Thr Asp Phe Thr Leu Lys Ile Ser Arg Val Glu Ala Glu Asp Leu Gly
            20                  25                  30

Val Tyr Phe Cys
        35

<210> SEQ ID NO 21
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 21

Phe Gly Ser Gly Thr Lys Leu Glu Ile Lys
1               5                   10

<210> SEQ ID NO 22
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gln Val Gln Leu Gln Gln Pro Gly Ala Glu Leu Val Arg Pro Gly Ala
1               5                   10                  15

Ser Val Lys Leu Ser Cys Lys Ala Ser
            20                  25

<210> SEQ ID NO 23
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Glu Val Gln Leu Val Glu Ser Gly Gly Asp Leu Val Lys Pro Gly Gly
1               5                   10                  15

Ser Leu Lys Leu Ser Cys Ala Ala Ser
            20                  25

<210> SEQ ID NO 24
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Ile Asn Trp Val Lys Gln Arg Pro Gly Gln Gly Leu Glu Trp Ile Gly
1               5                   10                  15

Asn

<210> SEQ ID NO 25
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Met Ser Trp Val Arg Gln Ser Pro Asp Lys Arg Met Glu Trp Val Ala
1               5                   10                  15

Thr

<210> SEQ ID NO 26
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 26

Asn Tyr Asn Gln Lys Phe Lys Asp Lys Ala Thr Leu Thr Val Asp Lys
1               5                   10                  15

Ser Ser Ser Thr Ala Tyr Met Gln Leu Ser Ser Pro Thr Ser Glu Asp
                20                  25                  30

Ser Ala Val Tyr Tyr Cys
            35

<210> SEQ ID NO 27
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Tyr Tyr Pro Asp Ser Val Lys Gly Arg Phe Thr Val Ser Arg Asp Asn
1               5                   10                  15

Ala Lys Asn Thr Leu Tyr Leu Gln Met Ser Ser Leu Arg Ser Glu Asp
                20                  25                  30

Thr Ala Ile Phe Tyr Cys
            35

<210> SEQ ID NO 28
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Trp Gly Gln Gly Thr Ser Val Thr Val Ser Ser
1               5                   10

<210> SEQ ID NO 29
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Asp Val Leu Met Thr Gln Ile Pro Leu Ser Leu Pro Val Ser Leu Gly
1               5                   10                  15

Asp His Ala Ser Ile Ser Cys Arg Ser Ser Gln Asn Ile Val Tyr Ser
                20                  25                  30

Asp Gly Asn Thr Tyr Leu Glu Trp Tyr Leu Gln Lys Pro Gly Gln Ser
            35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Arg Ile
65                  70                  75                  80

Ser Arg Val Glu Ala Glu Asp Leu Gly Val Tyr Tyr Cys Leu Gln Gly
                85                  90                  95

Ser His Val Pro Pro Thr Phe Gly Ser Gly Thr Lys Leu Glu Ile Lys
                100                 105                 110

```
<210> SEQ ID NO 30
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Gln Val Gln Leu Gln Gln Pro Gly Ala Glu Leu Val Arg Pro Gly Ala
1               5                   10                  15

Ser Val Lys Leu Ser Cys Lys Ala Ser Gly Tyr Thr Phe Thr Ser Tyr
            20                  25                  30

Trp Ile Asn Trp Val Lys Gln Arg Pro Gly Gln Gly Leu Glu Trp Ile
        35                  40                  45

Gly Asn Ile Tyr Pro Ser Asp Ser Tyr Thr Asn Tyr Asn Gln Lys Phe
    50                  55                  60

Lys Asp Lys Ala Thr Leu Thr Val Asp Lys Ser Ser Ser Thr Ala Tyr
65                  70                  75                  80

Met Gln Leu Ser Ser Pro Thr Ser Glu Asp Ser Ala Val Tyr Tyr Cys
                85                  90                  95

Ala Arg Glu Arg Tyr Glu Arg Asp Ala Met Asp Tyr Trp Gly Gln Gly
            100                 105                 110

Thr Ser Val Thr Val Ser Ser
        115

<210> SEQ ID NO 31
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Asp Val Val Met Thr Gln Ser Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu Gln Trp Tyr Leu Gln Lys Pro Gly Gln Ser
        35                  40                  45

Pro Asn Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Phe Thr Phe Gly Ser Gly Thr Lys Leu Glu Ile Lys
            100                 105                 110

<210> SEQ ID NO 32
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Glu Val Gln Leu Val Glu Ser Gly Gly Asp Leu Val Lys Pro Gly Gly
1               5                   10                  15
```

```
Ser Leu Lys Leu Ser Cys Ala Ala Ser Gly Phe Thr Phe Ser Ser Tyr
            20                  25                  30

Gly Met Ser Trp Val Arg Gln Ser Pro Asp Lys Arg Met Glu Trp Val
        35                  40                  45

Ala Thr Ile Ser Ser Gly Gly Ser Tyr Thr Tyr Tyr Pro Asp Ser Val
    50                  55                  60

Lys Gly Arg Phe Thr Val Ser Arg Asp Asn Ala Lys Asn Thr Leu Tyr
65                  70                  75                  80

Leu Gln Met Ser Ser Leu Arg Ser Glu Asp Thr Ala Ile Phe Tyr Cys
                85                  90                  95

Val Arg Asp Arg Tyr Asp Gly Met Asp Tyr Trp Gly Gln Gly Thr Ser
            100                 105                 110

Val Thr Val Ser Ser
        115

<210> SEQ ID NO 33
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Gln Asn Ile Val Tyr Ser Asp Gly Asn Thr Tyr
1               5                   10

<210> SEQ ID NO 34
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Gln Ser Leu Val His Ser Asn Gly Asn Thr Tyr
1               5                   10

<210> SEQ ID NO 35
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Lys Val Ser
1

<210> SEQ ID NO 36
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Leu Gln Gly Ser His Val Pro Pro Thr
1               5
```

```
<210> SEQ ID NO 37
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Ser Gln Ser Thr His Val Pro Phe Thr
1               5

<210> SEQ ID NO 38
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Gly Tyr Thr Phe Thr Ser Tyr Trp
1               5

<210> SEQ ID NO 39
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Gly Phe Thr Phe Ser Ser Tyr Gly
1               5

<210> SEQ ID NO 40
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Ile Tyr Pro Ser Asp Ser Tyr Thr
1               5

<210> SEQ ID NO 41
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Ile Ser Ser Gly Gly Ser Tyr Thr
1               5

<210> SEQ ID NO 42
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42
```

```
Ala Arg Glu Arg Tyr Glu Arg Asp Ala Met Asp Tyr
1               5                   10
```

<210> SEQ ID NO 43
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

```
Val Arg Asp Arg Tyr Asp Gly Met Asp Tyr
1               5                   10
```

<210> SEQ ID NO 44
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

```
Arg Ala Asp Ala Ala Pro Thr Val Ser Ile Phe Pro Pro Ser Ser Glu
1               5                   10                  15

Gln Leu Thr Ser Gly Gly Ala Ser Val Val Cys Phe Leu Asn Asn Phe
            20                  25                  30

Tyr Pro Lys Asp Ile Asn Val Lys Trp Lys Ile Asp Gly Ser Glu Arg
        35                  40                  45

Gln Asn Gly Val Leu Asn Ser Trp Thr Asp Gln Asp Ser Lys Asp Ser
    50                  55                  60

Thr Tyr Ser Met Ser Ser Thr Leu Thr Leu Thr Lys Asp Glu Tyr Glu
65                  70                  75                  80

Arg His Asn Ser Tyr Thr Cys Glu Ala Thr His Lys Thr Ser Thr Ser
                85                  90                  95

Pro Ile Val Lys Ser Phe Asn Arg Asn Glu Cys
            100                 105
```

<210> SEQ ID NO 45
<211> LENGTH: 324
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

```
Ala Lys Thr Thr Pro Pro Ser Val Tyr Pro Leu Ala Pro Gly Ser Ala
1               5                   10                  15

Ala Gln Thr Asn Ser Met Val Thr Leu Gly Cys Leu Val Lys Gly Tyr
            20                  25                  30

Phe Pro Glu Pro Val Thr Val Thr Trp Asn Ser Gly Ser Leu Ser Ser
        35                  40                  45

Gly Val His Thr Phe Pro Ala Val Leu Gln Ser Asp Leu Tyr Thr Leu
    50                  55                  60

Ser Ser Ser Val Thr Val Pro Ser Ser Thr Trp Pro Ser Glu Thr Val
65                  70                  75                  80

Thr Cys Asn Val Ala His Pro Ala Ser Ser Thr Lys Val Asp Lys Lys
                85                  90                  95
```

```
Ile Val Pro Arg Asp Cys Gly Cys Lys Pro Cys Ile Cys Thr Val Pro
            100                 105                 110
Glu Val Ser Ser Val Phe Ile Phe Pro Pro Lys Pro Lys Asp Val Leu
        115                 120                 125
Thr Ile Thr Leu Thr Pro Lys Val Thr Cys Val Val Val Asp Ile Ser
    130                 135                 140
Lys Asp Asp Pro Glu Val Gln Phe Ser Trp Phe Val Asp Asp Val Glu
145                 150                 155                 160
Val His Thr Ala Gln Thr Gln Pro Arg Glu Glu Gln Phe Asn Ser Thr
                165                 170                 175
Phe Arg Ser Val Ser Glu Leu Pro Ile Met His Gln Asp Trp Leu Asn
            180                 185                 190
Gly Lys Glu Phe Lys Cys Arg Val Asn Ser Ala Ala Phe Pro Ala Pro
        195                 200                 205
Ile Glu Lys Thr Ile Ser Lys Thr Lys Gly Arg Pro Lys Ala Pro Gln
    210                 215                 220
Val Tyr Thr Ile Pro Pro Pro Lys Glu Gln Met Ala Lys Asp Lys Val
225                 230                 235                 240
Ser Leu Thr Cys Met Ile Thr Asp Phe Phe Pro Glu Asp Ile Thr Val
                245                 250                 255
Glu Trp Gln Trp Asn Gly Gln Pro Ala Glu Asn Tyr Lys Asn Thr Gln
            260                 265                 270
Pro Ile Met Asp Thr Asp Gly Ser Tyr Phe Val Tyr Ser Lys Leu Asn
        275                 280                 285
Val Gln Lys Ser Asn Trp Glu Ala Gly Asn Thr Phe Thr Cys Ser Val
    290                 295                 300
Leu His Glu Gly Leu His Asn His His Thr Glu Lys Ser Leu Ser His
305                 310                 315                 320
Ser Pro Gly Lys

<210> SEQ ID NO 46
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Phe Glu His Cys Asn Phe Asn Asp Val Thr Thr Arg Leu Arg Glu Asn
1               5                   10                  15
Glu Leu Thr Tyr Tyr Cys Cys Lys Lys Asp Leu
            20                  25

<210> SEQ ID NO 47
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Phe Glu His Cys Asn Phe Asn Asp Val Thr Thr Arg Leu Arg Glu Asn
1               5                   10                  15
Glu Leu Thr Tyr Tyr Cys Cys Lys Lys
            20                  25
```

-continued

```
<210> SEQ ID NO 48
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

His Cys Asn Phe Asn Asp Val Thr Thr Arg Leu Arg Glu Asn Glu Leu
1               5                   10                  15

Thr Tyr Tyr Cys Cys Lys Lys
            20

<210> SEQ ID NO 49
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Ala Cys Asn Phe Asn Asp Val Thr Thr Arg Leu Arg Glu Asn Glu Leu
1               5                   10                  15

Thr Tyr Tyr Cys Ala Ala Lys
            20

<210> SEQ ID NO 50
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term NH2

<400> SEQUENCE: 50

Ala Cys Asn Phe Asn Asp Val Thr Thr Arg Leu Arg Glu Asn Glu Leu
1               5                   10                  15

Thr Tyr Tyr Cys Ala Ala Lys
            20

<210> SEQ ID NO 51
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Ala Phe Glu His Cys Asn Phe Asn Asp Val Thr Thr Arg Leu Arg Glu
1               5                   10                  15

Asn Glu Leu Thr Tyr Tyr Cys Ala Ala Lys Asp Leu
            20                  25

<210> SEQ ID NO 52
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (24)..(24)
<223> OTHER INFORMATION: Beta-Ala

<400> SEQUENCE: 52

Ala Phe Glu His Cys Asn Phe Asn Asp Val Thr Thr Arg Leu Arg Glu
1               5                   10                  15

Asn Glu Leu Thr Tyr Tyr Cys Ala Lys Asp Leu
            20                  25

<210> SEQ ID NO 53
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (24)..(24)
<223> OTHER INFORMATION: Alpha-amino-isobutyric acid

<400> SEQUENCE: 53

Ala Phe Glu His Cys Asn Phe Asn Asp Val Thr Thr Arg Leu Arg Glu
1               5                   10                  15

Asn Glu Leu Thr Tyr Tyr Cys Xaa Ala Lys Asp Leu
            20                  25

<210> SEQ ID NO 54
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Asn Lys Cys Trp Lys Phe Glu His Cys Asn Phe Asn Asp Val
1               5                   10

<210> SEQ ID NO 55
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Trp Lys Phe Glu His
1               5

<210> SEQ ID NO 56
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Asn Lys Ala Trp Lys Phe Glu His Ala Asn Phe Asn Asp
1               5                   10

<210> SEQ ID NO 57
<211> LENGTH: 14
```

-continued

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac

<400> SEQUENCE: 57

Asn Lys Ala Trp Lys Phe Glu His Ala Asn Phe Asn Asp Cys
1               5                   10
```

ANTI-CD59 ANTIBODIES

CROSS REFERENCE TO RELATED APPLICATIONS

This application is a 35 U.S.C. § 371 U.S. National Stage Entry of International Application No. PCT/US2018/027856 filed Apr. 17, 2018, entitled "METHODS AND ANTIBODIES FOR DIABETES-RELATED APPLICATIONS", which claims the benefit of priority of U.S. Provisional Patent Application No. 62/488,346, filed Apr. 21, 2017, entitled "METHODS AND ANTIBODIES FOR DIABETES-RELATED APPLICATIONS", the contents of each of which are herein incorporated by reference in their entirety.

SEQUENCE LISTING

The present application is being filed along with a Sequence Listing in electronic format. The Sequence Listing file, entitled 2047_1010US371_SL.txt, was created on Oct. 21, 2019, and is 43,245 bytes in size. The information in electronic format of the Sequence Listing is incorporated herein by reference in its entirety.

FIELD OF THE INVENTION

This disclosure relates to compounds, methods, and kits for detecting factors associated with elevated glucose levels. These factors include proteins that have been post-translationally modified due to elevated blood glucose levels. The disclosure also relates to methods of diagnosing, treating, monitoring, and stratifying patients based on detected factors.

BACKGROUND

Diabetes is characterized by elevated blood glucose levels. Sustained elevation of blood glucose levels may affect proteins by a process known as glycation. Glycation is the non-enzymatic attachment of glucose to proteins and is considered a major pathophysiological mechanism causing tissue damage in diabetic subjects. Glycation involves the reaction of glucose and/or other reducing sugars with amino groups in proteins resulting in the formation of a Schiff base or aldimine. This labile adduct can tautomerize via the Amadori rearrangement to the more stable ketoamine.

Different glycated proteins have been identified in diabetic subjects, including albumin, hemoglobin and others. The function of glycated proteins may be impaired, depending on the location of the amino group(s) affected. For example, amino-terminal glycation of the β-chains of hemoglobin gives rise to the glycated hemoglobin (HbA1c) in which responsiveness to 2,3-diphosphoglycerate is decreased and oxygen affinity increased. Glycation of the major thrombin inhibitor of the coagulation system, antithrombin III, decreases its affinity for heparin, and has been postulated to contribute to the hypercoagulable state associated with diabetes.

Measurement of the extent of protein "glycation" of certain proteins may be a valuable clinical tool to provide a more stable indicator of glycemic control than shorter term indicators such as measuring glucose levels directly, ultimately helping to improve the efficacy of treatments. The present inventors have previously shown that K41 glycation of CD59 is correlated to abnormal blood sugar levels and that glycation at K41 interferes with the normal activity of CD59 (U.S. Pat. Nos. 6,835,545; 7,049,082; and U.S. Pat. No. 7,439,330; the entire contents of each of which are incorporated herein by reference).

There remains; however, a need for improved methods of detecting and diagnosing diabetic conditions. In particular, there remains a need for simple, accurate and cost-effective methods, reagents, and kits for detecting and/or determining the level of glycated CD59 (GCD59) in subject samples.

SUMMARY

In some embodiments, the present disclosure provides an antibody, wherein the antibody includes a heavy chain variable domain (VH) with a complementarity determining region (CDR) having at least 70% amino acid sequence identity to an amino sequence selected from the group consisting of SEQ ID NOs: 38-43. The CDR may be a CDR-H3 selected from the group consisting of SEQ ID NOs: 42 and 43. The VH may include a CDR-H1 having an amino acid sequence with at least 70% sequence identity with a sequence selected from the group consisting of SEQ ID NOs: 38 and 39; a CDR-H2 having an amino acid sequence with at least 70% sequence identity with a sequence selected from the group consisting of SEQ ID NOs: 40 and 41; and a CDR-H3 having an amino acid sequence with at least 70% sequence identity with a sequence selected from the group consisting of SEQ ID NOs: 42 and 43. The antibody may include a light chain variable domain (VL) with a CDR having at least 70% amino acid sequence identity to an amino acid sequence selected from the group consisting of SEQ ID NOs: 33-37. The VL may include a CDR-L3 selected from the group consisting of SEQ ID NOs: 36 and 37. The VL may include a CDR-L1 having an amino acid sequence with at least 70% sequence identity with a sequence selected from the group consisting of SEQ ID NOs: 33 and 34; a CDR-L2 having an amino acid sequence with at least 30% sequence identity with the sequence of SEQ ID NOs: 35; and a CDR-L3 having an amino acid sequence with at least 70% sequence identity with a sequence selected from the group consisting of SEQ ID NOs: 36 and 37. The antibody may be a monoclonal antibody. The antibody may be a humanized antibody. The antibody may be an IgG1, IgG2, IgG3, or IgG4 antibody.

Antibodies of the present disclosure may include at least one variable domain with an amino acid sequence having at least 95% sequence identity to an amino acid sequence selected from the group consisting of SEQ ID NOs: 29-32. The at least one variable domain may include a VH with an amino acid sequence that is at least 95% identical to an amino acid sequence selected from the group consisting of SEQ ID NOs: 30 and 32. The at least one variable domain may include a VL with an amino acid sequence that is at least 95% identical to an amino acid sequence selected from the group consisting of SEQ ID NOs: 29 and 31.

Antibodies of the present disclosure may include a translated amino acid sequence having at least 95% sequence identity to an amino acid sequence selected from the group consisting of SEQ ID NOs: 3 and 5. The heavy chain may be encoded by a nucleotide sequence having at least 95% sequence identity to a nucleic acid sequence selected from the group consisting of SEQ ID NOs: 7, 8, and 10.

Antibodies of the present disclosure may include a light chain with a translated amino acid sequence having at least 95% sequence identity to an amino acid sequence selected from the group consisting of SEQ ID NOs: 2 and 4. The light chain may be encoded by a nucleotide sequence selected from the group consisting of SEQ ID NOs: 6 and 9.

In some embodiments, the present disclosure provides an antibody that includes a heavy chain with a translated amino acid sequence with at least 95% sequence identity to an amino acid sequence selected from the group consisting of SEQ ID NOs: 3 and 5; and a light chain with a translated amino acid sequence with at least 95% sequence identity to an amino acid sequence selected from the group consisting of SEQ ID NOs: 2 and 4. The antibody may bind to CD59. The antibody may bind to a non-glycated epitope of CD59. The antibody may bind to an epitope of CD59 that does not include lysine 41 (K41). The antibody may bind to a glycated epitope of glycated CD59 (GCD59). The glycated epitope of GCD59 may include an Amadori-modified K41. Binding to the glycated epitope of GCD59 may feature an equilibrium dissociation constant (KD) of from about 1.0 pM to about $5.0 \times 10^8$ pM. The KD may be from about 1.5 pM to about 150 pM. The GCD59 epitope may be presented in a format selected from at least one of a surface-associated format and a solution-based format. The solution-based format may include a solution of at least one of urine, plasma, serum, blood, sweat, and saliva. The serum may be diluted by from about 1:1 to about 1:100,000.

In some embodiments, the present disclosure provides a kit that includes a capture agent and instructions for use of the kit. The capture agent may be a capture antibody, wherein the capture antibody is an antibody described herein. The capture antibody may bind CD59. The kit may include a detection agent, wherein the detection agent is selected from a lectin and a detection antibody, wherein the detection antibody is an antibody described herein. The detection antibody may bind CD59. The detection agent may bind to a glycosylated epitope of GCD59. The glycosylated epitope of GCD59 may include an N-glycosylated epitope of GCD59. The kit may include a compound for generation of a calibration curve. The kit may include at least one buffer. The buffer may be used to contact a subject sample. The buffer may include at least one of a reducing agent, an oxidizing agent, dithiothreitol (DTT), and beta-mercaptoethanol (BME). The kit may include one or more internal controls. The one or more internal controls may include one or more plasma assay controls. The kit may include one or more of an assay diluent, conjugate diluent, and wash buffer. One or more reagents in the kit may be lyophilized.

Methods of the present disclosure include a method of detecting a target protein in a sample. The target protein may include GCD59. The method may include obtaining a sample; applying the sample to a substrate, the substrate having a capture antibody, wherein the capture antibody is selected from an antibody binding to an N-glycosylated epitope of CD59 or any of the antibodies described herein; applying a detection antibody to the substrate, wherein the detection antibody binds to a target epitope selected from a glycated or non-glycated epitope of GCD59; and analyzing the substrate for the presence of the detection antibody. The method may include obtaining a sample; applying the sample to a substrate, the substrate having a capture antibody, wherein the capture antibody is selected from an antibody described herein; applying a detection antibody, wherein the detection antibody binds to a non-glycated epitope of GCD59; and analyzing the substrate for the presence of the detection antibody. The detection antibody may be selected from any of the antibodies described herein. The target epitope may include a glycosylated epitope of GCD59. The target epitope may include an N-glycosylated epitope of GCD59. The sample may be a subject sample. The subject sample may be selected from at least one of urine, blood, plasma, serum, sweat, and saliva. The sample may be treated with at least one of a reducing agent, an oxidizing agent, dithiothreitol (DTT), and beta-mercaptoethanol (BME). The sample may be a diluted sample. The sample may be diluted by from about 1:1 to about 1:1.000.

In some embodiments, the present disclosure provides a method of detecting a target protein in a sample, wherein the target protein includes GCD59, the method including obtaining a sample, wherein the sample includes at least one of a cell, a tissue, and a tissue section; applying a detection antibody to the sample, wherein the detection antibody binds to a target epitope, the target epitope including a glycated epitope of GCD59; and analyzing the sample for the presence of the detection antibody. The detection antibody may include a detectable label. The detectable label may be selected from the group consisting of biotin, streptavidin, avidin, a fluorescent label, an enzymatic label, a luminescent label, and a radioactive label. The detection antibody may be detected using a secondary detection agent, wherein the secondary detection agent includes a detectable label. The secondary detection agent may be an antibody. The detectable label may be selected from the group consisting of biotin, streptavidin, avidin, a fluorescent label, an enzymatic label, a luminescent label, and a radioactive label. The substrate may be selected from at least one of an assay plate, a bead, a membrane, a conducting surface, and a conducting nanoparticle. The method may be carried out at the point of care. At least part of the method may be carried out in conjunction with a patient monitoring device. The patient monitoring device may be capable of receiving and/or transmitting an electronic signal. The patient monitoring device may be a smart device selected from at least one of a smart phone and a smart watch. The concentration or concentration equivalent of the target protein may be determined by measuring at least one signal associated with the detectable label.

In some embodiments, the present disclosure provides a method of evaluating a subject that includes collecting at least one test sample from a subject; carrying out any of the methods described herein, wherein the sample includes at least one test sample and at least one control sample; and comparing the concentration or concentration equivalent of a target protein in the at least one test sample to the concentration or concentration equivalent of the target protein detected in the at least one control sample.

In some embodiments, the present disclosure provides a method of screening, diagnosing, and monitoring of a diabetes-related indication in a subject by carrying out any of the methods described herein, wherein the subject is diagnosed with the diabetes-related indication if the concentration or concentration equivalent of a target protein in at least one test sample varies from the concentration or concentration equivalent of the target protein detected in at least one control sample by a threshold value. Methods of the present disclosure include a method of monitoring one or more diabetes-related indications in a subject, wherein the subject has one or more diabetes-related indications, the method including collecting at least two test samples from a subject, wherein the at least two test samples are obtained over at least two time periods; carrying out any of the methods described herein, wherein the sample includes the at least two test sample collected; and monitoring the variation between the concentration or concentration equivalent of the target protein in the at least two test samples. Methods of monitoring one or more diabetes-related indications in a subject may be carried out as part of a companion diagnostic method.

In some embodiments, methods of evaluating the effectiveness of a therapeutic method are provided. The therapeutic method may include the administration of at least one therapeutic compound to at least one subject.

Methods of the present disclosure may include a method of assigning a level of risk to a subject, wherein the level of risk includes a level of risk associated with developing one or more diabetes-related indications. The method may include comparing the concentration or concentration equivalent of a target protein in at least one test sample with the concentration or concentration equivalent of the target protein detected in the at least one control sample; and assigning the level of risk to the subject based on the comparison performed. The subject may be at least one of a pregnant subject, a subject suspected of being pregnant, and a subject capable of becoming pregnant. The diabetic-related indication may include gestational diabetes mellitus.

In some embodiments, the present disclosure provides a device for carrying out all or part of any of the methods described herein. The device may be a wearable device. The wearable device may include a wristband. The wearable device may be a smart watch.

In some embodiments, methods of the present disclosure used for screening, diagnosing, and monitoring of a diabetes-related indication in a subject may include detecting a target epitope, wherein the target epitope may include an N-glycosylated epitope of GCD59 that includes residue N18 of GCD59, wherein residue N18 is N-glycosylated. The one or more diabetes-related indications may be selected from at least one of diabetes, a predisposition to an organ specific complication of diabetes; pre-clinical diabetic peripheral neuropathy; pre-clinical diabetic nephropathy; pre-clinical diabetic retinopathy; and pre-clinical diabetic vascular disease.

Methods of the present disclosure include a method of detecting N-glycosylated GCD59, the method including isolating GCD59 using an antibody described herein; and analyzing the GCD59 isolated to detect the presence of an N-glycosylated residue. The analysis may include the use of mass spectrometry. The analysis may include the use of a lectin capable of binding the N-glycosylated residue. The N-glycosylated residue may be residue N18 of GCD59.

In some embodiments, the present disclosure provides a method of identifying an inhibitor of CD59 K41 glycation including contacting at least one sample with at least one test compound, wherein the at least one sample includes CD59 and conditions suitable for K41 glycation; determining the concentration or concentration equivalent of GCD59 in the at least one sample; and identifying one or more of the at least one test compound as an inhibitor of CD59 K41 glycation if the concentration or concentration equivalent of GCD59 determined is reduced as a result of contact with the at least one test compound. Determining the concentration or concentration equivalent of GCD59 may be carried out with an antibody described here. The at least one test compound may be selected from one or more of a small molecule, a peptide, a synthetic construct, a fusion protein, an aptamer, a nucleic acid, and an antibody. In some embodiments, the present disclosure provides an inhibitor developed according to a method of identifying an inhibitor of CD59 K41 glycation that includes a method presented herein.

In some embodiments, the present disclosure provides a vector encoding one or more of the antibodies described herein or a fragment or variant thereof. The present disclosure also provides recombinant antibodies produced using such a vector, cells including such a vector, and antibodies produced by such cells.

Methods of the present disclosure include a method of treating a diabetes-related indication using an inhibitor produced according to any of the methods described herein. The diabetes-related indication may be selected from one or more of complement dysfunction, hemolytic disease, paroxysmal nocturnal hemoglobinuria, atypical hemolytic-uremic syndrome, wound healing, complications associated with organ transplantation, a vascular indication, and age-related macular degeneration.

In some embodiments, the present disclosure provides a method of assigning a level of risk to a gestational subject, wherein the level of risk includes a level of risk associated with developing one or more GDM-related condition. The method may include collecting at least one test sample from a gestational carrier of a gestational subject; using an assay to determine the level of GCD59 in the test sample, wherein the assay utilizes a capture antibody and a detection antibody, each selected from any of those described herein; and assigning a level of risk associated with developing one or more GDM-related condition based on the level of GCD59 determined in the test sample. The one or more GDM-related conditions may be selected from one or more of macrosomia, large gestational age (LGA), a birth defect, birth trauma, hyperbilirubinemia, hypoglycemia, seizures, and still birth.

Methods of the present disclosure may be carried out through the use of a platform technology. The platform technology may include an automated platform technology.

BRIEF DESCRIPTION OF THE FIGURES

The foregoing and other objects, features and advantages will be apparent from the following description of particular embodiments of the invention, as illustrated in the accompanying drawings. The drawings are not necessarily to scale, emphasis instead being placed upon illustrating the principles of various embodiments of the invention.

FIG. 1B is a graph showing the correlation between the percent urine sample dilution and synthetic peptide units (SPU) detected using antibody D2.

DETAILED DESCRIPTION

Figure 1A:
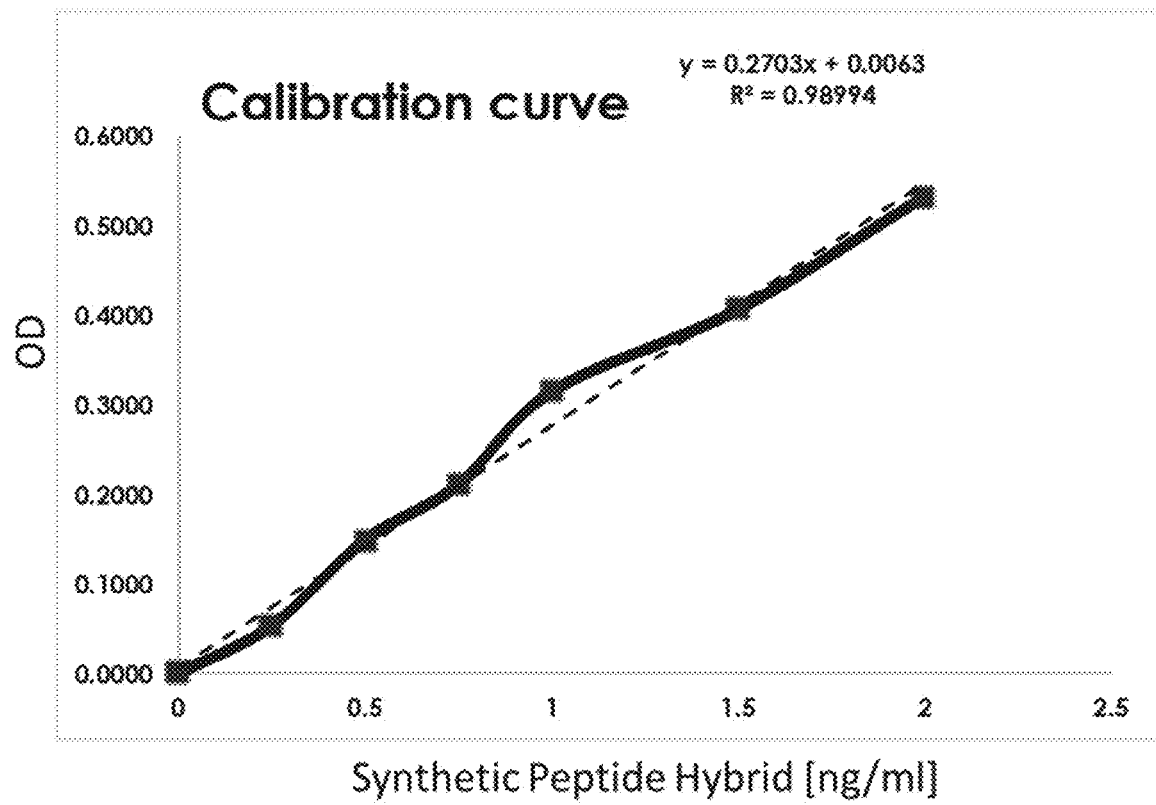
FIG. 1A is a graph of a calibration curve generated using an Amadori-modified GCD59 surrogate and an anti-Amadori-modified GCD59 antibody (D2).

In some embodiments, the present disclosure provides compounds, compositions, reagents, methods, kits, and devices for various therapeutic, diagnostic, monitoring, and/or research applications. Part of the present disclosure relates to kits, e.g., diagnostic kits, for detecting post-translational modifications to CD59. Included herein are amino acid and nucleic acid sequences encoding antibodies that bind to modified or unmodified CD59. These antibodies may be used in kits used to detect post-translationally modified CD59 for a variety of therapeutic applications. These and other antibody applications are described in further detail herein.

I. Compounds and Compositions

Proteins

Compounds of the present disclosure may include proteins. Proteins may exist as a whole polypeptide, a plurality of polypeptides or fragments of polypeptides, which independently may be encoded by one or more nucleic acids, a plurality of nucleic acids, fragments of nucleic acids or variants of any of the aforementioned. As used herein, "polypeptide" means a polymer of amino acid residues (natural or unnatural) linked together most often by peptide bonds. The term, as used herein, refers to proteins, polypeptides, and peptides of any size, structure, or function. In some instances, the polypeptide encoded is smaller than about 50 amino acids and the polypeptide is then termed a peptide. If the polypeptide is a peptide, it will be at least about 2, 3, 4, or at least 5 amino acid residues long. Thus, polypeptides include gene products, naturally occurring polypeptides, synthetic polypeptides, homologs, orthologs, paralogs, fragments and other equivalents, variants, and analogs of the foregoing. A polypeptide may be a single molecule or may be a multi-molecular complex such as a dimer, trimer or tetramer. They may also comprise single chain or multichain polypeptides and may be associated or linked. The term polypeptide may also apply to amino acid polymers in which one or more amino acid residues are an artificial chemical analogue of a corresponding naturally occurring amino acid.

The term "polypeptide variant" refers to molecules which differ in their amino acid sequence from a native or reference sequence. The amino acid sequence variants may possess substitutions, deletions, and/or insertions at certain positions within the amino acid sequence, as compared to a native or reference sequence. Ordinarily, variants will possess at least about 50% identity (homology) to a native or reference sequence, and preferably, they will be at least about 80%, more preferably at least about 90% identical (homologous) to a native or reference sequence.

In some embodiments "variant mimics" are provided. As used herein, the term "variant mimic" is one which contains one or more amino acids which would mimic an activated sequence. For example, glutamate may serve as a mimic for phosphoro-threonine and/or phosphoro-serine. Alternatively, variant mimics may result in deactivation or in an inactivated product containing the mimic, e.g., phenylalanine may act as an inactivating substitution for tyrosine; or alanine may act as an inactivating substitution for serine. The amino acid sequences of polypeptides of the present disclosure may comprise naturally occurring amino acids and as such may be considered to be proteins, peptides, polypeptides, or fragments thereof. Alternatively, polypeptides of the present disclosure may include both naturally and non-naturally occurring amino acids.

The term "amino acid sequence variant" refers to molecules with some differences in their amino acid sequences as compared to a native or starting sequence. The amino acid sequence variants may possess substitutions, deletions, and/or insertions at certain positions within the amino acid sequence. "Native" or "starting" sequence should not be confused with a wild type sequence. As used herein, a native or starting sequence is a relative term referring to an original molecule against which a comparison may be made. "Native" or "starting" sequences or molecules may represent the wild-type (that sequence found in nature) but do not have to be the wild-type sequence.

Ordinarily, variants will possess at least 70%, at least 75%, at least 80%, at least 85%, at least 90%, at least 95%, at least 96%, at least 97%, at least 98%, at least 99%, at least 99.5% at least 99.8%, or at least 99.9% sequence identity as compared to a native sequence. "Sequence identity" as it applies to amino acid sequences is defined as the percentage of residues in the candidate amino acid sequence that are identical with the residues in the amino acid sequence of a second sequence after aligning the sequences and taking gaps and fragments into consideration, if necessary, to achieve the maximum percent sequence identity. Calculation of the percent identity of two polymeric sequences, for example, can be performed by aligning the two sequences for optimal comparison purposes (e.g., gaps can be introduced in one or both of a first and a second polymeric sequence for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or 100% of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. For example, the percent identity between two nucleotide sequences can be determined using methods such as those described in Computational Molecular Biology, Lesk, A. M., ed., Oxford University Press, New York, 1988; Biocomputing: Informatics and Genome Projects, Smith, D. W., ed., Academic Press, New York, 1993; Sequence Analysis in Molecular Biology, von Heinje, G., Academic Press, 1987; Computer Analysis of Sequence Data, Part 1, Griffin, A. M., and Griffin, H. G., eds., Humana Press, New Jersey, 1994; and Sequence Analysis Primer, Gribskov, M. and Devereux. J., eds., M Stockton Press, New York, 1991; each of which is incorporated herein by reference. For example, the percent identity between two nucleotide sequences can be determined using the algorithm of Meyers and Miller (CABIOS, 1989, 4:11-17), which has been incorporated into the ALIGN program (version 2.0) using a PAM120 weight residue table, a gap length penalty of 12 and a gap penalty of 4. The percent identity between two nucleotide sequences can, alternatively, be determined using the GAP program in the GCG software package using an NWSgapdna.CMP matrix. Methods commonly employed to determine percent identity between sequences include, but are not limited to those disclosed in Carillo, H., and Lipman, D., SIAM J Applied Math., 48:1073 (1988); incorporated herein by reference. Techniques for determining identity are codified in publicly available computer programs. Exemplary computer software to determine homology between two sequences include, but are not limited to, GCG program package, Devereux, J., et al., *Nucleic Acids Research,* 12(1), 387 (1984)), BLASTP, BLASTN, and FASTA Altschul, S. F. et al., *J. Molec. Biol.,* 215, 403 (1990)).

By "homologs" as it applies to amino acid sequences is meant the corresponding sequence of other species having substantial identity to a second sequence of a second species. "Analogs" is meant to include polypeptide variants which differ by one or more amino acid alterations. e.g., substitutions, additions or deletions of amino acid residues that still maintain the properties of the parent polypeptide. "Homology" refers to the overall relatedness between polymeric molecules, e.g., between polypeptide molecules, nucleic acid molecules, and oligosaccharides. Determination of homology may take into account the sequence identity, sequence similarity, three dimensional conformation, and/or function of the polymeric molecules being compared.

The present invention contemplates several types of polypeptides which are amino acid based including variants and derivatives. These include substitutional, insertional, deletion and covalent variants and derivatives. As such, included within the scope of this invention are polypeptides containing substitutions, insertions and/or additions, deletions and covalently modifications. For example, sequence tags or amino acids, such as one or more lysines, can be added to the peptide sequences of the invention (e.g., at the N-terminal or C-terminal ends). Sequence tags can be used for peptide purification or localization. Lysines can be used to increase peptide solubility or to allow for biotinylation. Alternatively, amino acid residues located at the carboxy and amino terminal regions of the amino acid sequence of a peptide or protein may optionally be deleted providing for truncated sequences. Certain amino acids (e.g., C-terminal or N-terminal residues) may alternatively be deleted depending on the use of the sequence, as for example, expression of the sequence as part of a larger sequence which is soluble, or linked to a solid support.

"Substitutional variants" when referring to proteins are those that have at least one amino acid residue in a native or starting sequence removed and a different amino acid inserted in its place at the same position. The substitutions may be single, where only one amino acid in the molecule has been substituted, or they may be multiple, where two or more amino acids have been substituted in the same molecule.

As used herein the term "conservative amino acid substitution" refers to the substitution of an amino acid that is normally present in the sequence with a different amino acid of similar size, charge, or polarity. Examples of conservative substitutions include the substitution of a non-polar (hydrophobic) residue such as isoleucine, valine and leucine for another non-polar residue. Likewise, examples of conservative substitutions include the substitution of one polar (hydrophilic) residue for another such as between arginine and lysine, between glutamine and asparagine, and between glycine and serine. Additionally, the substitution of a basic residue such as lysine, arginine or histidine for another, or the substitution of one acidic residue such as aspartic acid or glutamic acid for another acidic residue are additional examples of conservative substitutions. Examples of non-conservative substitutions include the substitution of a non-polar (hydrophobic) amino acid residue such as isoleucine, valine, leucine, alanine, methionine for a polar (hydrophilic) residue such as cysteine, glutamine, glutamic acid or lysine and/or a polar residue for a non-polar residue.

"Insertional variants" when referring to proteins are those with one or more amino acids inserted immediately adjacent to an amino acid at a particular position in a native or starting sequence. "Immediately adjacent" to an amino acid means connected to either the alpha-carboxy or alpha-amino functional group of the amino acid.

"Deletional variants" when referring to proteins, are those with one or more amino acids in the native or starting amino acid sequence removed. Ordinarily, deletional variants will have one or more amino acids deleted in a particular region of the molecule.

As used herein, the term "derivative" is used synonymously with the term "variant" and refers to a molecule that has been modified or changed in any way relative to a reference molecule or starting molecule. In some embodiments, derivatives include native or starting proteins that have been modified with an organic proteinaceous or non-proteinaceous derivatizing agent, and post-translational modifications. Covalent modifications are traditionally introduced by reacting targeted amino acid residues of the protein with an organic derivatizing agent that is capable of reacting with selected side-chains or terminal residues, or by harnessing mechanisms of post-translational modifications that function in selected recombinant host cells. The resultant covalent derivatives are useful in programs directed at identifying residues important for biological activity, for immunoassays, or for the preparation of anti-protein antibodies for immunoaffinity purification of the recombinant protein. Such modifications are within the ordinary skill in the art and are performed without undue experimentation.

Certain post-translational modifications are the result of the action of recombinant host cells on the expressed polypeptide. Glutaminyl and asparaginyl residues are frequently post-translationally deamidated to the corresponding glutamyl and aspartyl residues. Alternatively, these residues are deamidated under mildly acidic conditions. Either form of these residues may be present in the proteins used in accordance with the present invention.

Other post-translational modifications include hydroxylation of proline and lysine, phosphorylation of hydroxyl groups of seryl or threonyl residues, methylation of the alpha-amino groups of lysine, arginine, and histidine side chains (T. E. Creighton. Proteins: Structure and Molecular Properties, W.H. Freeman & Co., San Francisco, pp. 79-86 (1983)).

Covalent derivatives specifically include fusion molecules in which proteins of the invention are covalently bonded to a non-proteinaceous polymer. The non-proteinaceous polymer ordinarily is a hydrophilic synthetic polymer. i.e. a polymer not otherwise found in nature. However, polymers which exist in nature and are produced by recombinant or in vitro methods are useful, as are polymers which are isolated from nature. Hydrophilic polyvinyl polymers fall within the scope of this invention. e.g. polyvinylalcohol and polyvinylpyrrolidone. Particularly useful are polyvinylalkylene ethers such a polyethylene glycol, polypropylene glycol. The proteins may be linked to various non-proteinaceous polymers, such as polyethylene glycol, polypropylene glycol or polyoxyalkylenes, in the manner set forth in U.S. Pat. Nos. 4,640,835; 4,496,689; 4,301,144; 4,670,417; 4,791,192 or 4,179,337.

"Features" when referring to proteins are defined as distinct amino acid sequence-based components of a molecule. Features of the proteins of the present invention include surface manifestations, local conformational shape, folds, loops, half-loops, domains, half-domains, sites, termini or any combination thereof.

As used herein when referring to proteins the term "surface manifestation" refers to a polypeptide based component of a protein appearing on an outermost surface.

As used herein when referring to proteins the term "local conformational shape" means a polypeptide based structural manifestation of a protein which is located within a definable space of the protein.

As used herein when referring to proteins the term "fold" means the resultant conformation of an amino acid sequence upon energy minimization. A fold may occur at the secondary or tertiary level of the folding process. Examples of secondary level folds include beta sheets and alpha helices. Examples of tertiary folds include domains and regions formed due to aggregation or separation of energetic forces. Regions formed in this way include hydrophobic and hydrophilic pockets, and the like.

As used herein the term "turn" as it relates to protein conformation means a bend which alters the direction of the backbone of a peptide or polypeptide and may involve one, two, three or more amino acid residues.

As used herein when referring to proteins the term "loop" refers to a structural feature of a peptide or polypeptide which reverses the direction of the backbone of a peptide or polypeptide and comprises four or more amino acid residues. Oliva et al. have identified at least 5 classes of protein loops (J. Mol Biol 266 (4): 814-830; 1997).

As used herein when referring to proteins the term "half-loop" refers to a portion of an identified loop having at least half the number of amino acid resides as the loop from which it is derived. It is understood that loops may not always contain an even number of amino acid residues. Therefore, in those cases where a loop contains or is identified to comprise an odd number of amino acids, a half-loop of the odd-numbered loop will comprise the whole number portion or next whole number portion of the loop (number of amino acids of the loop/2±0.5 amino acids). For example, a loop identified as a 7 amino acid loop could produce half-loops of 3 amino acids or 4 amino acids (7/2=3.5±0.5 being 3 or 4).

As used herein when referring to proteins the term "domain" refers to a motif of a polypeptide having one or more identifiable structural or functional characteristics or properties (e.g., binding capacity, serving as a site for protein-protein interactions.

As used herein when referring to proteins the term "half-domain" means portion of an identified domain having at least half the number of amino acid resides as the domain from which it is derived. It is understood that domains may not always contain an even number of amino acid residues. Therefore, in those cases where a domain contains or is identified to comprise an odd number of amino acids, a half-domain of the odd-numbered domain will comprise the whole number portion or next whole number portion of the domain (number of amino acids of the domain/2±0.5 amino acids). For example, a domain identified as a 7 amino acid domain could produce half-domains of 3 amino acids or 4 amino acids (7/2=3.5±0.5 being 3 or 4). It is also understood that sub-domains may be identified within domains or half-domains, these subdomains possessing less than all of the structural or functional properties identified in the domains or half domains from which they were derived. It is also understood that the amino acids that comprise any of the domain types herein need not be contiguous along the backbone of the polypeptide (i.e., nonadjacent amino acids may fold structurally to produce a domain, half-domain or subdomain).

As used herein when referring to proteins the terms "site" as it pertains to amino acid based embodiments is used synonymous with "amino acid residue" and "amino acid side chain". A site represents a position within a peptide or polypeptide that may be modified, manipulated, altered, derivatized or varied within the polypeptide based molecules of the present invention.

As used herein the terms "termini or terminus" when referring to proteins refers to an extremity of a peptide or polypeptide. Such extremity is not limited only to the first or final site of the peptide or polypeptide but may include additional amino acids in the terminal regions. The polypeptide based molecules of the present invention may be characterized as having both an N-terminus (terminated by an amino acid with a free amino group ($NH_2$)) and a C-terminus (terminated by an amino acid with a free carboxyl group ($CO_2H$)). Proteins of the invention are in some cases made up of multiple polypeptide chains brought together by disulfide bonds or by non-covalent forces (multimers, oligomers). These sorts of proteins will have multiple N- and C-termini. Alternatively, the termini of the polypeptides may be modified such that they begin or end, as the case may be, with a non-polypeptide based moiety such as an organic conjugate.

Once any of the features have been identified or defined as a component of a molecule of the invention, any of several manipulations and/or modifications of these features may be performed by moving, swapping, inverting, deleting, randomizing or duplicating. Furthermore, it is understood that manipulation of features may result in the same outcome as a modification to the molecules of the invention. For example, a manipulation which involved deleting a domain would result in the alteration of the length of a molecule just as modification of a nucleic acid to encode less than a full length molecule would.

Modifications and manipulations can be accomplished by methods known in the art such as site-directed mutagenesis. The resulting modified molecules may then be tested for sequence, structure, and/or activity using in vitro or in vivo assays such as those described herein or any other suitable screening assay known in the art.

Isotopic Variants

Compounds of the present disclosure may contain one or more atoms that are isotopes. As used herein, the term "isotope" refers to a chemical element that has one or more additional neutron. In one embodiment, compounds of the present invention may be deuterated. As used herein, the term "deuterated" refers to a substance that has had one or more hydrogen atoms replaced by deuterium isotopes. Deuterium isotopes are isotopes of hydrogen. The nucleus of hydrogen contains one proton while deuterium nuclei contain both a proton and a neutron. Compounds may be deuterated in order to change a physical property of the compound, such as stability, or to allow the compounds to be used in diagnostic and experimental applications.

Antibodies

In some embodiments, the present disclosure provides antibodies that bind to target proteins. As used herein, a "target protein" refers to any protein of interest including proteins that are being analyzed as part of an assay, diagnostic method, or any other method described herein that involves protein detection and/or analysis. Target proteins may also include synthetic constructs having one or more amino acid-based segments. Synthetic constructs may include one or more non-amino acid based elements such as linkers, chemical moieties, or chemical groups. In some cases, target proteins include moieties or tags, including, but not limited to detectable labels.

In some embodiments, target proteins include CD59, fragments of CD59, variants of CD59, post-translationally modified versions of CD59, and/or synthetic constructs that include CD59, CD59 fragments, CD59 variants, post-translationally modified CD59, post-translationally modified CD59 fragments, and/or post-translationally modified variants of CD59. Mature human CD59 (hCD59; lacking the signal sequence) has the amino acid sequence of LQCYNCPNPT$^{10}$ADCKTAVNCS$^{20}$SDFDACLITK$^{30}$AGL QVYNKCW$^{40}$KFEHCNFNDV$^{50}$ TTRLRENELT$^{60}$ YYCCKKDLCN$^{70}$FNEQLEN$^{77}$ (SEQ ID NO: 1). Residue numbers of hCD59 referred to herein refer to residue numbers present in this sequence, hCD59 fragments and variants may include any of those described in in European Patent Number EP2348050, International Publication Number WO2015084994, and U.S. Pat. Nos. 9,068,006, 9,417,248, the contents of each of which are herein incorporated by reference in their entireties.

In some embodiments, antibodies of the present disclosure bind to non-glycated epitopes of CD59. Some capture antibodies bind to epitopes of hCD59 that do not include lysine 41 (referred to herein as "K41") of hCD59 (SEQ ID NO: 1). Some antibodies of the present disclosure bind to glycated epitopes of glycated CD59 (GCD59). Such glycated epitopes may include K41-glycated human GCD59. Some glycated epitopes include Amadori-modified K41.

Glycated epitopes of hCD59 may include any of those described in in European Patent Number EP2348050, International Publication Number WO2015084994, and U.S. Pat. Nos. 9,068,006, 9,417,248, the contents of each of which are herein incorporated by reference in their entireties.

In some embodiments, antibodies binding to glycated epitopes that include Amadori-modified K41 of GCD59 (also referred to herein as "anti-Amadori-modified GCD59 antibodies" or "anti-Amadori antibodies") may bind with an equilibrium dissociation constant ($K_D$) of from about 1.0 pM to about $5.0 \times 10^8$ pM. In some cases, the $K_D$ is from about 1.5 pM to about 150 pM.

Antibodies of the present disclosure may include capture antibodies. Capture antibodies refer to antibodies that bind to target proteins for the purposes of isolation, immobilization, and/or further analysis of such target proteins. Capture antibodies may bind CD59 or fragments and/or variants thereof. Some capture antibodies bind to CD59 regardless of the presence of one or more post-translational modification.

Some capture antibodies bind to target epitopes of target proteins.

As used herein, a "target epitope" refers to a specific sequence, feature, or moiety that an antibody or other molecule has a specific affinity for. Target epitopes present on CD59, CD59 fragments, or CD59 variants, may include, but are not limited to specific amino acids, amino acid sequences, and/or three-dimensional features, in some cases including glycated, non-glycated, glycosylated, and non-glycosylated features thereof. Target epitopes of hCD59 may include any of the aforementioned CD59 epitopes or any of the hCD59 (human CD59) epitopes described in in European Patent Number EP2348050, International Publication Number WO2015084994, and U.S. Pat. Nos. 9,068,006, 9,417,248, the contents of each of which are herein incorporated by reference in their entireties. Such epitopes may be captured or detected in a variety of ways including the use of antibodies or other biomolecules such as lectins, aptamers, other proteins or nucleic acids. For example, CD59, e.g., hCD59 epitopes such as N-glycosylated epitopes may be detected using any detection agent which is specific enough to bind to and/or separate CD59 from other proteins or milieu in which the CD59 protein is found. Detection agents may be antibodies which bind to or recognize CD59 irrespective of its glycosylation state, e.g., glycated or non-glycated.

Detection antibodies, as used herein, are antibodies that bind target proteins for the purposes of determining the presence, absence, and/or level of such target proteins or for the characterization of a target protein. In some cases, detection antibodies may be used to determine the presence or absence of a target epitope on a target protein. Such target epitopes may include post-translationally modified epitopes present on target proteins. In some embodiments, detection antibodies may target CD59. Such detection antibodies may recognize an epitope of CD59 that may vary among CD59 species (e.g., different post-translationally modified CD59 species). In some embodiments, detection antibodies recognize post-translationally modified epitopes present on CD59. In one example, detection antibodies recognize glycated CD59 (GCD59). Glycated hCD59 may include K41 glycated hCD59. In some cases, detection antibodies may recognize K41 glycated CD59 that bears a sugar residue in Amadori form. Examples of K41 Amadori-modified hCD59 are described, for example, in U.S. Pat. No. 9,068,006 and International Publication Number WO2015/084994, the contents of each of which are herein incorporated by reference in their entirety. Some detection antibodies bind only GCD59, but not non-glycated forms. Antibodies described herein as "capture" or "detection" antibodies are not to be limited to capture and detection functions, respectively. In some cases, such antibodies may be useful for other purposes (e.g., therapeutic or manufacturing), including, but not limited to any of the purposes described herein.

In some embodiments, antibodies of the present disclosure bind to target proteins presented in a solution-based format. As used herein, a "solution-based format" refers to a protein conformation that is present in a solution. Such solutions may include, but are not limited to saline, buffer (e.g., phosphate buffered saline), serum, plasma, blood, lymph, sweat, urine, and saliva. In some cases, antibodies may be capable of binding target proteins in diluted serum or plasma. In some cases, serum may be diluted by from about 1:1 to about 1:100,000.

As used herein, the term "antibody" is referred to in the broadest sense and specifically covers various embodiments including, but not limited to monoclonal antibodies, polyclonal antibodies, multispecific antibodies (e.g. bispecific antibodies formed from at least two intact antibodies), and antibody fragments (e.g., diabodies) so long as they exhibit a desired biological activity (e.g., "functional"). Antibodies are primarily amino-acid based molecules but may also comprise one or more modifications (including, but not limited to the addition of sugar moieties, fluorescent moieties, chemical tags, etc.).

As used herein, "antibody-based" or "antibody-derived" compositions are monomeric or multi-meric polypeptides which comprise at least one amino-acid region derived from a known or parental antibody sequence and at least one amino acid region derived from a non-antibody sequence, e.g., mammalian protein.

Antibodies of the present disclosure may be therapeutic, diagnostic, industrial, or used for research purposes. Further, antibodies of the disclosure may include fragments of such antibodies or antibodies that have been developed to include one or more of such fragments (e.g., variable domains or complementarity determining regions (CDRs)).

In some embodiments, antibodies of the present disclosure may be used capture CD59 and/or GCD59 in samples (e.g., clinical samples).

Antibody Generation

Antibodies of the present disclosure may be produced using methods known in the art. Such methods may include, but are not limited to immunization and display technologies (e.g., phage display, yeast display, and ribosomal display). Antibodies may be developed, for example, using naturally occurring or synthetic antigens. As used herein, an "antigen" is an entity which induces or evokes an immune response in an organism. An immune response is characterized by the reaction of the cells, tissues and/or organs of an organism to the presence of a foreign entity. Such an immune response typically leads to the production by the organism of one or more antibodies against the foreign entity, e.g., antigen or a portion of the antigen. As used herein, "antigens" also refer to binding partners for specific antibodies or binding agents in a display library.

Antibodies of the present disclosure may be derived from antibodies produced using hybridoma technology. Host animals (e.g. mice, rabbits, goats, and llamas) may be immunized by an injection with an antigenic protein to elicit lymphocytes that specifically bind to the antigen. Lymphocytes may be collected and fused with immortalized cell lines to generate hybridomas which can be cultured in a suitable culture medium to promote growth. The antibodies produced by the cultured hybridomas may be subjected to analysis to determine binding specificity of the antibodies for the target antigen. Once antibodies with desirable characteristics are identified, corresponding hybridomas may be subcloned through limiting dilution procedures and grown by standard methods. The antibodies produced by these cells may be isolated and purified using standard immunoglobulin purification procedures.

Recombinant antibodies, as used herein, are antibodies produced by expression of recombinant DNA. Recombinant antibodies of the present disclosure may be generated using standard techniques known in the art. Recombinant antibodies may be produced using variable domains obtained from hybridoma cell-derived antibodies produced according to methods described herein. Heavy and light chain variable region cDNA sequences of antibodies may be determined using standard biochemical techniques. Total RNA may be extracted from antibody-producing hybridoma cells and converted to cDNA by reverse transcriptase (RT) polymerase chain reaction (PCR). PCR amplification may be carried out on resulting cDNA to amplify variable region genes. Such amplification may comprise the use of primers specific for amplification of heavy and light chain sequences. In other embodiments, recombinant antibodies may be produced using variable domains obtained from other sources. This includes the use of variable domains selected from one or more antibody fragment library, such as an scFv library used in antigen panning. Resulting PCR products may then be subcloned into plasmids and may be subjected to sequence analysis for verification and/or optimization. Antibody coding sequences may be placed into expression vectors. For humanization, coding sequences for human heavy and light chain constant domains and/or variable domain framework regions may be used to substitute for homologous or otherwise corresponding murine sequences. The resulting constructs may then be transfected into cells (e.g., mammalian cells) for large scale translation. In some embodiments, recombinant antibodies and/or vectors encoding recombinant antibodies may be produced using one or more of any of the sequences presented herein.

Antibodies of the present disclosure may be generated using display technologies. Display technologies used to generate polypeptides of the invention may include any of the display techniques (e.g., display library screening techniques) disclosed in US Publication No. US2015/0284455, the contents of which are herein incorporated by reference in their entirety. In some embodiments, synthetic antibodies may be designed, selected or optimized by screening target antigens using display technologies (e.g. phage display technologies). Display libraries may comprise millions to billions of display particles (e.g. phage or cellular display particles), each expressing unique antibody fragments on their surfaces (e.g., as part of viral coat proteins or cell surface molecules or proteins). Such libraries may provide richly diverse resources that may be used to select potentially hundreds of antibody fragments with diverse levels of affinity for one or more antigens of interest (McCafferty, et al., 1990. Nature, 348:552-4; Edwards. B. M. et al., 2003. JMB. 334: 103-18; Schofield. D. et al., 2007. Genome Biol. 8, R254 and Pershad, K. et al., 2010. Protein Engineering Design and Selection. 23:279-88; the contents of each of which are herein incorporated by reference in their entirety). Antibody fragments present in such libraries may be scFv antibody fragments, comprising a fusion protein of VH and VL antibody domains joined by a flexible linker. In some cases, scFvs may contain the same sequence with the exception of unique sequences encoding variable loops of the CDRs. In some cases, scFvs are expressed as fusion proteins, linked to surface molecules (e.g. the N-terminus of the viral pill coat protein when using phage display particles). VL chains may be expressed separately for assembly with VH chains in the periplasm or intracellularly prior to complex incorporation into surface molecules. Precipitated library members may be sequenced from the bound display particles to obtain cDNA encoding desired scFvs. Antibody variable domains or CDRs from such sequences may be directly incorporated into antibody sequences for recombinant antibody production, or mutated and utilized for further optimization through affinity maturation.

In some embodiments, antibodies may be produced using yeast surface display technology, wherein antibody variable domain sequences may be expressed on the cell surface of *Saccharomyces cerevisiae*. Recombinant antibodies may be developed by displaying the antibody fragment of interest as a fusion to e.g. Aga2p protein on the surface of the yeast, where the protein interacts with proteins and small molecules in a solution, scFvs with affinity for desired antigens may be isolated from the yeast surface using magnetic separation and flow cytometry. Several cycles of yeast surface display and isolation may be done to attain scFvs with desired properties through directed evolution. Yeast display may, for example, be carried out according to any of the methods taught in Chao, G. et al., Nat Protoc. 2006, 1(2):755-68, the contents of which are herein incorporated by reference in their entirety.

IgG Synthesis

In some embodiments, antibodies of the present disclosure are IgG antibodies. IgG antibodies (e.g. IgG1, IgG2, IgG3 or IgG4) may include one or more variable domain and/or CDR amino acid sequences presented herein (or fragment or variants thereof). Such IgG antibodies may be synthesized for further testing and/or product development. Some IgG antibodies may be produced by insertion of one or more segments of cDNA encoding desired amino acid sequences into expression vectors suited for IgG production. Expression vectors may comprise mammalian expression vectors suitable for IgG expression in mammalian cells. Mammalian expression of IgGs may be carried out to ensure that antibodies produced comprise modifications (e.g. glycosylation) characteristic of mammalian proteins and/or to ensure that antibody preparations lack endotoxin and/or other contaminants that may be present in protein preparations from bacterial expression systems.

Antibody Fragments and Variants

Antibodies of the present disclosure may include antibody fragments (e.g., antigen binding regions) from intact antibodies. Examples of antibody fragments may include, but are not limited to Fab, Fab', F(ab')$_2$, and Fv fragments; diabodies; linear antibodies; and single-chain antibody molecules. In some embodiments, antibodies of the present disclosure include multispecific antibodies formed from antibody fragments. Papain digestion of antibodies produces two identical antigen-binding fragments, called "Fab" fragments, each with a single antigen-binding site. Also produced is a residual "Fc" fragment, whose name reflects its ability to crystallize readily. Pepsin treatment yields an F(ab')$_2$ fragment that has two antigen-binding sites and is still capable of cross-linking antigen. Antibodies of the present disclosure may comprise one or more of these fragments. For the purposes herein, an "antibody" may be made up of a heavy and light chain variable domain as well as an Fc region.

In one embodiment, the Fc region may be a modified Fc region, as described in US Patent Publication US20150065690, wherein the Fc region may have a single amino acid substitution as compared to the corresponding sequence for the wild-type Fc region, wherein the single amino acid substitution yields an Fc region with preferred properties to those of the wild-type Fc region. Non-limiting examples of Fc properties that may be altered by the single amino acid substitution include binding properties and response to pH conditions (e.g., altered stability and/or target affinity).

As used herein, the term "native antibody" refers to an usually heterotetrameric glycoprotein of about 150,000 Daltons, composed of two identical light (L) chains and two identical heavy (H) chains. Genes encoding native antibody heavy and light chains are known and segments making up each have been well characterized and described (Matsuda, F. et al., 1998. The Journal of Experimental Medicine. 188(11); 2151-62 and Li, A. et al., 2004. Blood. 103(12: 4602-9, the content of each of which are herein incorporated by reference in their entirety). Each light chain is linked to a heavy chain by one covalent disulfide bond, while the number of disulfide linkages varies among the heavy chains of different immunoglobulin isotypes. Each heavy and light chain typically have regularly spaced intrachain disulfide bridges. Each heavy chain has at one end a heavy chain variable domain ($V_H$) followed by a number of constant domains. Each light chain has a light chain variable domain at one end ($V_L$) and a constant domain at its other end; the constant domain of the light chain is aligned with the first constant domain of the heavy chain, and the light chain variable domain is aligned with the variable domain of the heavy chain.

As used herein, the term "variable domain" refers to specific antibody domains found on both the antibody heavy and light chains that may differ extensively in sequence among antibodies and are used in the binding and specificity of each particular antibody for its particular antigen. Variable domains typically include hypervariable regions. As used herein, the term "hypervariable region" refers to a region within a variable domain having amino acid residues responsible for antigen binding. The amino acids present within the hypervariable regions determine the structure of the complementarity determining regions (CDRs) that become part of the antigen-binding site of the antibody. As used herein, the term "CDR" refers to a region of an antibody having a structure that is complementary to its target antigen or epitope. Other portions of the variable domain, not interacting with the antigen, are referred to as framework (FW) regions. The antigen-binding site (also known as the antigen combining site or paratope) typically includes amino acid residues necessary to interact with a particular antigen. The exact residues making up antigen-binding sites are typically elucidated by co-crystallography with bound antigen, however computational assessments can also be used based on comparisons with other antibodies (Strohl, W. R. Therapeutic Antibody Engineering. Woodhead Publishing, Philadelphia Pa. 2012. Ch. 3, p 47-54, the contents of which are herein incorporated by reference in their entirety). Determining residues making up CDRs may include the use of numbering schemes including, but not limited to, those taught by Kabat [Wu, T. T. et al., 1970, JEM, 132(2):211-50 and Johnson, G. et al., 2000, Nucleic Acids Res. 28(1): 214-8, the contents of each of which are herein incorporated by reference in their entirety]. Chothia [Chothia and Lesk, J. Mol. Biol. 196, 901 (1987), Chothia et al., Nature 342, 877 (1989) and Al-Lazikani, B. et al., 1997, J. Mol. Biol. 273(4):927-48, the contents of each of which are herein incorporated by reference in their entirety], and Lefranc (Lefranc, M. P. et al., 2005, Immunome Res. 1:3) and Honegger (Honegger, A. and Pluckthun, A. 2001. J. Mol. Biol. 309(3):657-70, the contents of each of which are herein incorporated by reference in their entirety).

$V_H$ and $V_L$ domains typically have three CDRs each. $V_L$ CDRs are referred to herein as CDR-L1, CDR-L2 and CDR-L3, in order of occurrence when moving from N- to C-terminus along the variable domain polypeptide. $V_H$ CDRs are referred to herein as CDR-H1, CDR-H2 and CDR-H3, in order of occurrence when moving from N- to C-terminus along the variable domain polypeptide. Each of the CDRs typically have favored canonical structures with the exception of the CDR-H3, which may include amino acid sequences that may be highly variable in sequence and length between antibodies resulting in a variety of three-dimensional structures in antigen-binding domains (Nikoloudis, D. et al., 2014. Peer J. 2:e456; the contents of which are herein incorporated by reference in their entirety). In some cases, CDR-H3s may be analyzed among a panel of related antibodies to assess antibody diversity. Various methods of determining CDR sequences are known in the art and may be applied to known antibody sequences (Strohl, W. R. Therapeutic Antibody Engineering. Woodhead Publishing, Philadelphia Pa. 2012. Ch. 3, p 47-54, the contents of which are herein incorporated by reference in their entirety).

In some embodiments, antibodies of the present disclosure may be formatted as Fv fragments. As used herein, the term "Fv" refers to an antibody fragment comprising the minimum fragment on an antibody needed to form a complete antigen-binding site. These regions consist of a dimer of one heavy chain and one light chain variable domain in tight, non-covalent association. Fv fragments can be generated by proteolytic cleavage, but are largely unstable. Recombinant methods are known in the art for generating stable Fv fragments, typically through insertion of a flexible linker between the light chain variable domain and the heavy chain variable domain [to form a single chain Fv (scFv)] or through the introduction of a disulfide bridge between heavy and light chain variable domains (Strobl, W. R. Therapeutic Antibody Engineering. Woodhead Publishing, Philadelphia Pa. 2012. Ch. 3, p 46-47, the contents of which are herein incorporated by reference in their entirety).

As used herein, the term "light chain" refers to a component of an antibody from any vertebrate species assigned to one of two clearly distinct types, called kappa and lambda based on amino acid sequences of constant domains.

In some embodiments, antibodies of the present disclosure may be formatted as scFvs. As used herein, the term "single chain Fv" or "scFv" refers to a fusion protein of $V_H$ and $V_L$ antibody domains, wherein these domains are linked together into a single polypeptide chain by a flexible peptide linker. In some embodiments, the Fv polypeptide linker enables the scFv to form the desired structure for antigen binding. In some embodiments, scFvs are utilized in conjunction with antibody display methods (e.g., phage display, yeast display or other display format) where they may be expressed in association with a surface member (e.g. phage coat protein or cell surface molecule) and used in the identification of high affinity peptides for a given antigen.

Antibodies of the present disclosure may be formatted as bispecific antibodies. As used herein, the term "bispecific antibody" refers to an antibody capable of binding two different antigens. Such antibodies typically comprise regions from at least two different antibodies. Bispecific antibodies may include any of those described in Riethmuller. G. 2012. Cancer Immunity. 12:12-18, Marvin. J. S. et al., 2005. Acta Pharmacologica Sinica. 26(6):649-58 and Schaefer, W. et al., 2011. PNAS. 108(27):11187-92, the contents of each of which are herein incorporated by reference in their entirety.

In some embodiments, antibodies of the present disclosure may be produced as diabodies. As used herein, the term "diabody" refers to a small antibody fragment with two antigen-binding sites. Diabodies comprise a heavy chain variable domain $V_H$ connected to a light chain variable domain $V_L$ in the same polypeptide chain. By using a linker that is too short to allow pairing between the two domains on the same chain, the domains are forced to pair with the complementary domains of another chain and create two antigen-binding sites. Diabodies are described more fully in, for example, EP404097; WO1993011161; and Hollinger et al. (Hollinger, P. et al., "Diabodies": Small bivalent and bispecific antibody fragments. PNAS. 1993. 90:6444-8) the contents of each of which are incorporated herein by reference in their entirety.

Antibodies of the present disclosure may be monoclonal antibodies. As used herein, the term "monoclonal antibody" refers to an antibody obtained from a population of substantially homogeneous cells (or clones), i.e., the individual antibodies comprising the population are identical and/or bind the same epitope, except for possible variants that may arise during production of the monoclonal antibodies, such variants generally being present in minor amounts. In contrast to polyclonal antibody preparations that typically include different antibodies directed against different determinants (epitopes), each monoclonal antibody is directed against a single determinant on the antigen The modifier "monoclonal" indicates the character of the antibody as being obtained from a substantially homogeneous population of antibodies, and is not to be construed as requiring production of the antibody by any particular method. The monoclonal antibodies herein include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies.

In some embodiments, antibodies of the present disclosure may be humanized antibodies. As used herein, the term "humanized antibody" refers to a chimeric antibody comprising a minimal portion from one or more non-human (e.g., murine) antibody source(s) with the remainder derived from one or more human immunoglobulin sources. For the most part, humanized antibodies are human immunoglobulins (recipient antibody) in which residues from the hypervariable region from an antibody of the recipient are replaced by residues from the hypervariable region from an antibody of a non-human species (donor antibody) such as mouse, rat, rabbit or nonhuman primate having the desired specificity, affinity, and/or capacity. Antibody humanization may be carried out according to any of the methods taught in US Publication No. US20150284455, the contents of which are herein incorporated by reference in their entirety.

Antibodies of the present disclosure may include antibody mimetics. As used herein, the term "antibody mimetic" refers to any molecule which mimics the function or effect of an antibody and which binds specifically and with high affinity to their molecular targets. In some embodiments, antibody mimetics may be monobodies, designed to incorporate the fibronectin type III domain (Fn3) as a protein scaffold (U.S. Pat. Nos. 6,673,901; 6,348,584). In some embodiments, antibody mimetics may be those known in the art including, but are not limited to affibody molecules, affilins, affitins, anticalins, avimers, Centyrins, DARPINS™, Fynomers and Kunitz and domain peptides. In other embodiments, antibody mimetics may include one or more non-peptide regions.

In some embodiments, antibodies of the present disclosure may include antibody variants. As used herein, the term "antibody variant" refers to a modified antibody (in relation to a native or starting antibody) or a biomolecule resembling a native or starting antibody in structure and/or function (e.g., an antibody mimetic). Antibody variants may be altered in their amino acid sequence, composition or structure as compared to a native antibody. Antibody variants may include, but are not limited to, antibodies with altered isotypes (e.g., IgA, IgD, IgE, $IgG_1$, $IgG_2$, $IgG_3$, $IgG_4$, or IgM), humanized variants, optimized variants, multispecific antibody variants (e.g., bispecific variants), and antibody fragments.

In some embodiments, antibodies of the present disclosure may include "unibodies," in which the hinge region has been removed from IgG4 molecules. While IgG4 molecules are unstable and can exchange light-heavy chain heterodimers with one another, deletion of the hinge region prevents heavy chain-heavy chain pairing entirely, leaving highly specific monovalent light/heavy heterodimers, while retaining the Fc region to ensure stability and half-life in vivo. This configuration may minimize the risk of immune activation or oncogenic growth, as IgG4 interacts poorly with FcRs and monovalent unibodies fail to promote intracellular signaling complex formation. Other antibodies may be "miniaturized" antibodies, which are compacted 100 kDa antibodies (see, e.g., Nelson, A. L., *MAbs.*, 2010. January-February; 2(1):77-83).

The preparation of antibodies, whether monoclonal or polyclonal, may be carried out using any methods known in the art. Techniques for the production of antibodies may be carried out as described, e.g. in Harlow and Lane "Antibodies, A Laboratory Manual", Cold Spring Harbor Laboratory Press, 1988; Harlow and Lane "Using Antibodies: A Laboratory Manual" Cold Spring Harbor Laboratory Press, 1999 and "Therapeutic Antibody Engineering: Current and Future Advances Driving the Strongest Growth Area in the Pharmaceutical Industry" Woodhead Publishing, 2012, the contents of each of which are herein incorporated by reference in their entirety.

Multispecific Antibodies

In some embodiments, antibodies of the present disclosure may bind more than one epitope. As used herein, the terms "multibody" or "multispecific antibody" refer to an antibody wherein two or more variable regions bind to different epitopes. The epitopes may be on the same or different targets. In certain embodiments, a multi-specific antibody is a "bispecific antibody," which recognizes two different epitopes on the same or different antigens.

Antibody-Drug Conjugates

In some embodiments, antibodies of the present disclosure may include antibodies developed for antibody-drug conjugate (ADC) therapeutic applications. ADCs are antibodies in which one or more cargo (e.g., therapeutic agents)

are attached (e.g., directly or via linker) ADCs are useful for delivery of therapeutic agents (e.g., drugs) to one or more target cells or tissues (Panowski, S. et al., 2014, mAbs 6:1, 34-45). In some cases, ADCs may be designed to bind to a surface antigen on a targeted cell. Upon binding, the entire antibody-antigen complex may be internalized and directed to a cellular lysosome. ADCs may then be degraded, releasing the bound cargo.

Antibody Sequences

In some embodiments, antibodies of the present disclosure may be produced using one or more of the translated polypeptides listed in Table 1 Signal peptides are marked in bold. In mature antibodies, the signal peptide may be removed prior to assembly of the full antibody.

TABLE 1

| | | Antibody chain translated polypeptides | |
|---|---|---|---|
| Antibody | Antibody chain | Sequence | SEQ ID NO |
| D2 | Light chain | MKLPVRLLVLMFWIPASNSDVLMTQIPLSLPVSL GDHASISCRSSQNIVYSDGNTYLEWYLQKPGQSP KLLIYKVSNRFSGVPDRFSGSGSGTDFTLRISRVEA EDLGVYYCLQGSHVPPTFGSGTKLEIKRADAAPT VSIFPPSSEQLTSGGASVVCFLNNFYPKDINVKWKI DGSERQNGVLNSWTDQDSKDSTYSMSSTLTLTKD EYERHNSYTCEATHKTSTSPIVKSFNRNEC | 2 |
| D2 | Heavy chain | MGWSCHILFLVATATGVHSQVQLQQPGAELVRP GASVKLSCKASGYTFTSYWINWVKQRPGQGLEW IGNIYPSDSYTNYNQKFKDKATLTVDKSSSTAYM QLSSPTSEDSAVYYCARERYERDAMDYWGQGTS VTVSSAKTIPPSVYPLAPGSAAQTNSMVTLGCLV KGYFPEPVTVTWNSGSLSSGVHTFPAVLQSDLYT LSSSVTVPSSTWPSETVTCNVAHPASSTKVDKKIV PRDCGCKPCICTVPEVSSVFIFPPKPKDVLTITLTPK VTCVVVDISKDDPEVQFSWFVDDVEVHTAQTQPR EEQFNSTFRSVSELPIMHQDWLNGKEFKCRVNSA AFPAPIEKTISKTKGRPKAPQVYTIPPPKEQMAKD KVSLTCMITDFFPEDITVEWQWNGQPAENYKNTQ PIMDTDGSYFVYSKLNVQKSNWEAGNTFTCSVLH EGLHNHHTEKSLSHSPGK | 3 |
| D3 | Light chain | MKLPVRLLVLMFWIPASNSDVLMTQIPLSLPVSL GDHASISCRSSQNIVYSDGNTYLEWYLQKPGQSP KLLIYKVSNRFSGVPDRFSGSGSGTDFTLRISRVEA EDLGVYYCLQGSHVPPTFGSGTKLEIKRADAAPT VSIFPPSSEQLTSGGASVVCFLNNFYPKDINVKWKI DGSERQNGVLNSWTDQDSKDSTYSMSSTLTLTKD EYERHNSYTCEATHKTSTSPIVKSFNRNEC | 2 |
| D3 | Heavy chain | MGWSCHILFLVATATGVHSQVQLQQPGAELVRP GASVKLSCKASGYTFTSYWINWVKQRPGQGLEW IGNIYPSDSYTNYNQKFKDKATLTVDKSSSTAYM QLSSPTSEDSAVYYCARERYERDAMDYWGQGTS VTVSSAKTIPPSVYPLAPGSAAQTNSMVTLGCLV KGYFPEPVTVTWNSGSLSSGVHTFPAVLQSDLYT LSSSVTVPSSTWPSETVTCNVAHPASSTKVDKKIV PRDCGCKPCICTVPEVSSVFIFPPKPKDVLTITLTPK VTCVVVDISKDDPEVQFSWFVDDVEVHTAQTQPR EEQFNSTFRSVSELPIMHQDWLNGKEFKCRVNSA AFPAPIEKTISKTKGRPKAPQVYTIPPPKEQMAKD KVSLTCMITDFFPEDITVEWQWNGQPAENYKNTQ PIMDTDGSYFVYSKLNVQKSNWEAGNTFTCSVLH EGLHNHHTEKSLSHSPGK | 3 |
| H9 | Light chain | MKLPVRLLVLMFWIPASSSDVVMTQSPLSLPVS LGDQASISCRSSQSLVHSNGNTYLQWYLQKPGQS PNLLIYKVSNRFSGVPDRFSGSGSGTDFTLKISRVE AEDLGVYFCSQSTHVPFTFGSGTKLEIKRADAAPT VSIFPPSSEQLTSGGASVVCFLNNFYPKDINVKWKI DGSERQNGVLNSWTDQDSKDSTYSMSSTLTLTKD EYERHNSYTCEATHKTSTSPIVKSFNRNEC | 4 |
| H9 | Heavy chain | MNFGLSLIFLALILKGVQCEVQLVESGGDLVKP GGSLKLSCAASGFTFSSYGMSWVRQSPDKRMEW VATISSGGSYTYYPDSVKGRFTVSRDNAKNTLYL QMSSLRSEDTAIFYCVRDRYDGMDYWGQGTSVT VSSAKTIPPSVYPLAPGSAAQTNSMVTLGCLVKG YFPEPVTVTWNSGSLSSGVHTFPAVLQSDLYTLSS SVTVPSSTWPSETVTCNVAHPASSTKVDKKIVPRD CGCKPCICTVPEVSSVFIFPPKPKDVLTITLTPKVTC VVVDISKDDPEVQFSWFVDDVEVHTAQTOPREEQ FNSTFRSVSELPIMHQDWLNGKEFKCRVNSAAFP APIEKTISKTKGRPKAPQVYTIPPPKEQMAKDVS LTCMITDFFPEDITVEWQWNGQPAENYKNTQPIM DTDGSYFVYSKLNVQKSNWEAGNTFTCSVLHEG LHNHHTEKSLSHSPGK | 5 |

Some antibodies may be produced using translated polypeptides having at least 60%, at least 65%, at least 70%, at least 75%, at least 80%, at least 85%, at least 90%, at least 95%, at least 96%, at least 97%, at least 98%, at least 98.5%, at least 99%, or at least 99.5% sequence identity to any of those listed in the previous table. Some antibodies may be produced using fragments of one or more of the amino acid sequences listed in the previous table.

In some embodiments, antibodies of the present disclosure may be produced using one or more of the nucleic acids listed in Table 2. Some antibodies may include heavy or light chains encoded by one or more nucleic acids having at least 60%, at least 65%, at least 70%, at least 75%, at least 80%, at least 85%, at least 90%, at least 95%, at least 96%, at least 97%, at least 98%, at least 98.5%, at least 99%, or at least 99.5% sequence identity to any of those listed. Some antibodies may be encoded by nucleic acids that include fragments and/or codon-optimized variants of one or more of the nucleic acid sequences listed. Antibodies may be produced from constructs carrying one or more of these nucleic acids, their variants, and/or fragments thereof.

TABLE 2

Nucleic acids encoding antibody heavy and light chains

| Antibody | Antibody chain | Sequence | SEQ ID NO |
|---|---|---|---|
| D2 | Light chain | ATGAAGTIGCCTGTTAGGCTGTTGGTGCTGATG TTCTGGATTCCTGCTTCCAACAGTGATGTTTTGA TGACCCAAATTCCACTCTCCCTGCCTGTCAGTCT TGGAGATCACGCCTCCATCTCTTGCAGATCTAG TCAGAACATTGTATATAGTGATGGAAACACCTA TTTAGAATGGTACCTGCAGAAACCAGGACAGTC TCCAAAGCTCCTGATCTACAAAGTTTCCAACCG ATTTTCTGGGGTCCCAGACAGGTTCAGTGGCAG TGGATCAGGGACAGATTTCACACTCAGGATCAG CAGAGTGGAGGCTGAGGATCTGGGAGTTTATTA CTGCTTGCAAGGTTCACATGTTCCTCCCACGTTC GGCTCGGGGACAAAGTTGGAGATAAAACGGGC TGATGCTGCACCAACTGTATCCATCTTCCCACC ATCCAGTGAGCAGTTAACATCTGGAGGTGCCTC AGTCGTGTGCTTCTTGAACAACTTCTACCCCAA AGACATCAATGTCAAGTGGAAGATTGATGGCA GTGAACGACAAAATGGCGTCCTGAACAGTTGG ACTGATCAGGACAGCAAAGACAGCACCTACAG CATGAGCAGCACCCTCACGTTGACCAAGGACG AGTATGAACGACATAACAGCTATACCTGTGAGG CCACTCACAAGACATCAACTTCACCCATTGTCA AGAGCTTCAACAGGAATGAGTGTTAAA | 6 |
| D2 | Heavy chain | ATGGGATGGAGCTGTATCATCCTCTTCTTGGTA GCAACAGCTACAGGTGTCCACTCCCAGGTCCAA CTGCAGCAGCCTGGGGCTGAGCTGGTGAGGCCT GGGGCTTCAGTGAAACTGTCCTGCAAGGCTTCT GGCTACACCTTCACCAGCTACTGGATAAACTGG GTGAAGCAGAGGCCTGGACAAGGCCTTGAGTG GATCGGAAATATTTATCCTTCTGATAGTTATACT AACTACAATCAAAAGTTCAAGGACAAGGCCAC ATTGACTGTAGACAAATCCTCCAGCACAGCCTA CATGCAGCTCAGCAGCCCGACATCTGAGGACTC TGCGGTCTATTACTGTGCAAGAGAAAGGTACGA AAGGGATGCTATGGACTACTGGGGTCAAGGAA CCTCAGTCACTGTCTCCTCAGCCAAAACGACAC CCCCATCTGTCTATCCACTGGCCCCTGGATCTGC TGCCCAAACTAACTCCATGGTGACCCTGGGATG CCTGGTCAAGGGCTATTTCCCTGAGCCAGTGAC AGTGACCTGGAACTCTGGATCCCTGTCCAGCGG TGTGCACACCTTCCCAGCTGTCCTGCAGTCTGA CCTCTACACTCTGAGCAGCTCAGTGACTGTCCC CTCCAGCACCTGGCCCAGCGAGACCGTCACCTG CAACGTTGCCCACCCGGCCAGCAGCACCAAGGT GGACAAGAAAATTGTGCCCAGGGATTGTGGTTG TAAGCCTTGCATATGTACAGICCCAGAAGTATC ATCTGTCTTCATCTTCCCCCCAAAGCCCAAGGA TGTGCTCACCATTACTCTGACTCCTAAGGTCAC GTGTGTIGTGGTAGACATCAGCAAGGATGATCC CGAGGTCCAGTTCAGCTGGITTGTAGATGATGT GGAGGTGCACACAGCTCAGACGCAACCCCGGG AGGAGCAGTTCAACAGCACTTTCCGCTCAGTCA GTGAACTTCCCATCATGCACCAGGACTGGCTCA ATGGCAAGGAGTTCAAATGCAGGGTCAACAGT GCAGCTTTCCCTGCCCCCATCGAGAAAACCATC TCCAAAACCAAAGGCAGACCGAAGGCTCCACA GGTGTACACCATTCCACCTCCCAAGGAGCAGAT GGCCAAGGATAAAGTCAGTCTGACCTGCATGAT AACAGACTTCTTCCCTGAAGACATTACTGTGGA GTGGCAGTGGAATGGGCAGCCAGCGGAGAACT ACAAGAACACTCAGCCCATCATGGACACAGAT GGCTCTTACTTCGTCTACAGCAAGCTCAATGTG | 7 |

TABLE 2-continued

Nucleic acids encoding antibody heavy and light chains

| Antibody | Antibody chain | Sequence | SEQ ID NO |
|---|---|---|---|
| | | CAGAAGAGCAACTGGGAGGCAGGAAATACTTT CACCTGCTCTGTGTTACATGAGGGCCTGCACAA CCACCATACTGAGAAGAGCCTCTCCCACTCTCC TGGTAAATAAA | |
| D3 | Light chain | ATGAAGTIGCCTGTTAGGCTGTTGGTGCTGATG TTCTGGATTCCTGCTTCCAACAGTGATGTTTTGA TGACCCAAATTCCACTCTCCCTGCCTGTCAGTCT TGGAGATCACGCCTCCATCTCTTGCAGATCTAG TCAGAACATTGTATATAGTGATGGAAACACCTA TTTAGAATGGTACCTGCAGAAACCAGGACAGTC TCCAAAGCTCCTGATCTACAAAGTTTCCAACCG ATTTTCTGGGGTCCCAGACAGGTTCAGTGGCAG TGGATCAGGGACAGATTCACACTCAGGATCAG CAGAGTGGAGGCTGAGGATCTGGGAGTTTATTA CTGCTTGCAAGGTTCACATGTTCCTCCCACGTTC GGCTCGGGGACAAAGTTGGAGATAAAACGGGC TGATGCTGCACCAACTGTATCCATCTTCCCACC ATCCAGTGAGCAGTTAACATCTGGAGGTGCCTC AGTCGTGTGCTTCTTGAACAACTTCTACCCCAA AGACATCAATGTCAAGTGGAAGATTGATGGCA GTGAACGACAAAATGGCGTCCTGAACAGTTGG ACTGATCAGGACAGCAAAGACAGCACCTACAG CATGAGCAGCACCCTCACGTTGACCAAGGACG AGTATGAACGACATAACAGCTATACCTGTGAGG CCACTCACAAGACATCAACTTCACCCATTGTCA AGAGCTTCAACAGGAATGAGTGTTAAA | 6 |
| D3 | Heavy chain | ATGGGATGGAGCTGTATCATCCTCTTCTTGGTA GCAACAGCTACAGGTGTCCACTCCCAGGTCCAA CTGCAGCAGCCTGGGGCTGAGCTGGTGAGGCCT GGGGCTTCAGTGAAACTGTCCTGCAAGGCTTCT GGCTACACCTTCACCAGCTACTGGATAAACTGG GTGAAGCAGAGGCCTGGACAAGGCCTTGAGTG GATCGGAAATATTTATCCTTCTGATAGTTATACT AACTACAATCAAAAGTTCAAGGACAAGGCCAC ATTGACTGTAGACAAATCCTCCAGCACAGCCTA CATGCAGCTCAGCAGCCCGACATCTGAGGACTC TGCGGTCTATTACTGTGCAAGAGAAAGGTACGA AAGGGATGCTATGGACTACTGGGGTCAAGGAA CCTCAGTCACTGTCTCCTCAGCCAAAACGACAC CCCCATCTGTCTATCCACTGGCCCCTGGATCTGC TGCCCAAACTAACTCCATGGTGACCCTGGGATG CCTGGTCAAGGGCTATTTCCCTGAGCCAGTGAC AGTGACCTGGAACTCTGGATCCCTGTCCAGCGG TGTGCACACCTTCCCAGCTGTCCTGCAGTCTGA CCTCTACACTCTGAGCAGCTCAGTGACTGTCCC CTCCAGCACCTGGCCCAGCGAGACCGTCACCTG CAACGTTGCCCACCCGGCCAGCAGCACCAAGGT GGACAAGAAAATTGTGCCCAGGGATTGTGGTTG TAAGCCTTGCATATGTACAGTCCCAGAAGTATC ATCTGTCTTCATCTTCCCCCCAAAGCCCAAGGA TGTGCTCACCATTACTCTGACTCCTAAGGTCAC GTGTGTTGTGGTAGACATCAGCAAGGATGATCC CGAGGTCCAGTTCAGCTGGTTTGTAGATGATGT GGAGGTGCACACAGCTCAGACGCAACCCCGGG AGGAGCAGTTCAACAGCACTTTCCGCTCAGTCA GTGAACTTCCCATCATGCACCAGGACTGGCTCA ATGGCAAGGAGTTCAAATGCAGGGTCAACAGT GCAGCTTTCCCTGCCCCCATCGAGAAAACCATC TCCAAAACCAAAGGCAGACCGAAGGCTCCACA GGTGTACACCATTCCACCTCCCAAGGAGCAGAT GGCCAAGGATAAAGTCAGTCTGACCTGCATGAT AACAGACTTCTTCCCTGAAGACATTACTGTGGA GTGGCAGTGGAATGGGCAGCCAGCGGAGAACT ACAAGAACACTCAGCCCATCATGGACACAGAT GGCTCTTACTTCGTCTACAGCAAGCTCAATGTG CAGAAGAGCAACTGGGAGGCAGGAAATACTTT CACCTGCTCTGTGTTACATGAGGGCCTGCACAA CCACCATACTGAGAAGAGCCTCTCCCACTCTCC GGGTAAATAAA | 8 |
| H9 | Light chain | ATGAAGTIGCCTGTTAGGCTGTTGGTGCTGATG TTCTGGATTCCTGCTTCCAGCAGTGATGTTGTGA TGACCCAAAGTCCACTCTCCCTGCCTGTCAGTC TTGGAGATCAAGCCTCCATCTCTTGCAGATCTA GTCAGAGCCTTGTACACAGTAATGGAAACACCT ATTTACAATGGTACCTGCAGAAGCCAGGCCAGT | 9 |

TABLE 2-continued

Nucleic acids encoding antibody heavy and light chains

| Antibody | Antibody chain | Sequence | SEQ ID NO |
|---|---|---|---|
| | | CTCCAAACCTCCTGATCTACAAAGTTTCCAACC<br>GATTTTCTGGGGTCCCAGACAGGTTCAGTGGCA<br>GTGGATCAGGGACAGATTTCACACTCAAGATCA<br>GTAGAGTGGAGGCTGAGGATCTGGGAGTTTATT<br>TCTGCTCTCAAAGTACACATGTTCCATTCACGTT<br>CGGCTCGGGGACAAAGTTGGAAATAAAACGGG<br>CTGATGCTGCACCAACTGTATCCATCTTCCCAC<br>CATCCAGTGAGCAGTTAACATCTGGAGGTGCCT<br>CAGTCGTGTGCTTCTTGAACAACTTCTACCCCA<br>AAGACATCAATGTCAAGTGGAAGATTGATGGC<br>AGTGAACGACAAAATGGCGTCCTGAACAGTTG<br>GACTGATCAGGACAGCAAAGACAGCACCTACA<br>GCATGAGCAGCACCCTCACGTTGACCAAGGAC<br>GAGTATGAACGACATAACAGCTATACCTGTGAG<br>GCCACTCACAAGACATCAACTTCACCCATTGTC<br>AAGAGCTTCAACAGGAATGAGTGTTAAA | |
| H9 | Heavy chain | ATGAACTTCGGGCTCAGCTTGATTTTCCTTGCCC<br>TCATTTTAAAAGGTGTCCAGTGTGAGGTGCAGC<br>TGGTGGAGTCTGGGGGAGACTTAGTGAAGCCTG<br>GAGGGTCCCTGAAACTCTCCTGTGCAGCCTCTG<br>GATTCACTTTCAGTAGCTATGGCATGTCTTGGG<br>TTCGCCAGAGTCCAGACAAGAGGATGGAATGG<br>GTCGCAACCATTAGTAGTGGTGGTAGTTATACG<br>TATTATCCAGACAGCGTGAAGGGGCGATTCACC<br>GTCTCCAGAGACAATGCCAAGAACACCCTGTAC<br>CTGCAAATGAGCAGTCTGAGGTCTGAGGACAC<br>AGCCATTTTTTACTGTGTAAGAGATAGGTACGA<br>CGGTATGGACTATTGGGGTCAGGGAACCTCAGT<br>CACCGTCTCCTCAGCCAAAACGACACCCCCATC<br>TGTCTATCCACTGGCCCCTGGATCTGCTGCCCA<br>AACTAACTCCATGGTGACCCTGGGATGCCTGGT<br>CAAGGGCTATTTCCCTGAGCCAGTGACAGTGAC<br>CTGGAACTCTGGATCCCTGTCCAGCGGTGTGCA<br>CACCTTCCCAGCTGTCCTGCAGTCTGACCTCTAC<br>ACTCTGAGCAGCTCAGTGACTGTCCCCTCCAGC<br>ACCTGGCCCAGCGAGACCGTCACCTGCAACGTT<br>GCCCACCCGGCCAGCAGCACCAAGGTGGACAA<br>GAAAATTGTGCCCAGGGATTGTGGTTGTAAGCC<br>TTGCATATGTACAGTCCCAGAAGTATCATCTGT<br>CTTCATCTTCCCCCCAAAGCCCAAGGATGTGCT<br>CACCATTACTCTGACTCCTAAGGTCACGTGTGT<br>TGTGGTAGACATCAGCAAGGATGATCCCGAGGT<br>CCAGTTCAGCTGGTTTGTAGATGATGTGGAGGT<br>GCACACAGCTCAGACGCAACCCCGGGAGGAGC<br>AGTTCAACAGCACTTTCCGCTCAGTCAGTGAAC<br>TTCCCATCATGCACCAGGACTGGCTCAATGGCA<br>AGGAGTTCAAATGCAGGGTCAACAGTGCAGCTT<br>TCCCTGCCCCCATCGAGAAAACCATCTCCAAAA<br>CCAAAGGCAGACCGAAGGCTCCACAGGTGTAC<br>ACCATTCCACCTCCCAAGGAGCAGATGGCCAAG<br>GATAAAGTCAGTCTGACCTGCATGATAACAGAC<br>TTCTTCCCTGAAGACATTACTGTGGAGTGGCAG<br>TGGAATGGGCAGCCAGCGGAGAACTACAAGAA<br>CACTCAGCCCATCATGGACACAGATGGCTCTTA<br>CTTCGTCTACAGCAAGCTCAATGTGCAGAAGAG<br>CAACTGGGAGGCAGGAAATACTTTCACCTGCTC<br>TGTGTTACATGAGGGCCTGCACAACCACCATAC<br>TGAGAAGAGCCTCTCCCACTCTCCTGGTAAATA<br>AA | 10 |

In some embodiments, antibodies of the present disclosure may include translated variable domains amino acid sequences having one or more of the translated leader amino acid sequences listed in Table 3. Some antibodies may have translated variable domain amino acid sequences having at least 60%, at least 65%, at least 70%, at least 75%, at least 80%, at least 85%, at least 90%, at least 95%, at least 96%, at least 97%, at least 98%, at least 98.5%, at least 99%, or at least 99.5% sequence identity to any of the amino acid sequences listed.

TABLE 3

Leader Sequences

| Antibody | Leader, Variable domain | Sequence | SEQ ID NO. |
|---|---|---|---|
| D2 | Leader 1, Light chain | MKLPVRLLVLMFWIPASNS | 11 |
| D3 | Leader 1, Light chain | MKLPVRLLVLMFWIPASNS | |11 |
| H9 | Leader 2, Light chain | MKLPVRLLVLMFWIPASSS | 12 |
| D2 | Leader 3, Heavy chain | MGWSCHILFLVATATGVHS | 13 |

TABLE 3-continued

Leader Sequences

| Antibody | Leader, Variable domain | Sequence | SEQ ID NO. |
|---|---|---|---|
| D3 | Leader 3, Heavy chain | MGWSCHILFLVATATGVHS | 13 |
| H9 | Leader 4, Heavy chain | MNFGLSLIFLALILKGVQC | 14 |

In some embodiments, antibodies of the present disclosure may include framework region (FR) amino acid sequences that include one or more of the amino acid sequences listed in Table 4. FR1, FR2, FR3, and FR4 refer to framework regions in order of location from the N-terminus of a variable domain to the C-terminus of a variable domain. Framework regions are typically followed by complementarity determining regions (CDRs) with the exception of FR4, which typically lies after the last CDR in a variable domain.

TABLE 4

Framework region sequences

| Antibody | Framework, Variable domain | Sequence | SEQ ID NO. |
|---|---|---|---|
| D2 | FR1, Light chain | DVLMTQIPLSLPVSLGDHASISCRSS | 15 |
| D3 | FRl, Light chain | DVLMTQIPLSLPVSLGDHASISCRSS | 15 |
| H9 | FR1, Light chain | DVVMTQSPLSLPVSLGDQASISCRSS | 16 |
| D2 | FR2, Light chain | LEWYLQKPGQSPKLLIY | 17 |
| D3 | FR2, Light chain | LEWYLQKPGQSPKLLIY | 17 |
| H9 | FR2, Light chain | LQWYLQKPGQSPNLLIY | 18 |
| D2 | FR3, Light chain | NRFSGVPDRFSGSGSGTDFTLRISRVEAEDLGVYYC | 19 |
| D3 | FR3, Light chain | NRFSGVPDRFSGSGSGTDFTLRISRVEAEDLGVYYC | 19 |
| H9 | FR3, Light chain | NRFSGVPDRFSGSGSGTDFTLKISRVEAEDLGVYFC | 20 |
| D2 | FR4, Light chain | FGSGTKLEIK | 21 |
| D3 | FR4, Light chain | FGSGTKLEIK | 21 |
| H9 | FR4, Light chain | FGSGTKLEIK | 21 |
| D2 | FR1, Heavy chain | QVQLQQPGAELVRPGASVKLSCKAS | 22 |
| D3 | FR1, Heavy chain | QVQLQQPGAELVRPGASVKLSCKAS | 22 |
| H9 | FR1, Heavy chain | EVOLVESGGDLVKPGGSLKLSCAAS | 23 |
| D2 | FR2, Heavy chain | INWVKQRPGQGLEWIGN | 24 |
| D3 | FR2, Heavy chain | INWVKQRPGQGLEWIGN | 24 |
| H9 | FR2, Heavy chain | MSWVRQSPDKRMEWVAT | 25 |
| D2 | FR3, Heavy chain | NYNQKFKDKATLTVDKSSSTAYMQLSSPTSEDSAVYYC | 26 |
| D3 | FR3, Heavy chain | NYNQKFKDKATLTVDKSSSTAYMQLSSPTSEDSAVYYC | 26 |
| H9 | FR3, Heavy chain | YYPDSVKGRFTVSRDNAKNTLYLQMSSLRSEDTAIFYC | 27 |
| D2 | FR4, Heavy chain | WGQGTSVTVSS | 28 |
| D3 | FR4, Heavy chain | WGQGTSVTVSS | 28 |
| H9 | FR4, Heavy chain | WGQGTSVTVSS | 28 |

In some embodiments, antibodies of the present disclosure may include one or more of the heavy chain variable domain ($V_H$) and light chain variable domain ($V_L$) amino acid sequences presented in Table 5. Some antibodies may include at least one variable domain with an amino acid sequence having at least 60%, at least 65%, at least 70%, at least 75%, at least 80%, at least 85%, at least 90%, at least 95%, at least 96%, at least 97%, at least 98%, at least 98.5%, at least 99%, or at least 99.5% sequence identity to any of those listed. Some antibodies may include variable domains having fragments or variants of one or more of the amino acid sequences listed.

TABLE 5

Antibody variable domain sequences

| Antibody | Antibody chain | Sequence | SEQ ID NO |
|---|---|---|---|
| D2 | Light chain | DVLMTQIPLSLPVSLGDHASISCRSSQNIVYSDGNTYLEWYLQKPGQSPKLLIYKVSNRFSGVPDRFSGSGSGTDFTLRISRVEAEDLGVYYCLQGSHVPPTFGSGTKLEIK | 29 |
| D2 | Heavy chain | QVQLQQPGAELVRPGASVKLSCKASGYTFTSYWINWVKQRPGOGLEWIGNIYPSDSYTNYNQKFKDKATLTVDKSSSTAYMQLSSPTSEDSAVYYCARERYERDAMDYWGQGTSVTVSS | 30 |
| D3 | Light chain | DVLMTQIPLSLPVSLGDHASISCRSSQNIVYSDGNTYLEWYLQKPGQSPKLLIYKVSNRFSGVPDRFSGSGSGTDFTLRISRVEAEDLGVYYCLQGSHVPPTFGSGTKLEIK | 29 |
| D3 | Heavy chain | QVQLQQPGAELVRPGASVKLSCKASGYTFTSYWINWVKQRPGQGLEWIGNIYPSDSYTNYNQKFKDKATLTVDKSSSTAYMQLSSPTSEDSAVYYCARERYERDAMDYWGQGTSVTVSS | 30 |
| H9 | Light chain | DVVMTQSPLSLPVSLGDQASISCRSSQSLVHSNGNTYLQWYLQKPGQSPNLLIYKVSNRFSGVPDRFSGSGSGTDFTLKISRVEAEDLGVYFCSQSTHVPFTFGSGTKLEIK | 31 |
| H9 | Heavy chain | EVOLVESGGDLVKPGGSLKLSCAASGFTFSSYGMSWVRQSPDKRMEWVATISSGGSYTYYPDSVKGRFTVSRDNAKNTLYLQMSSLRSEDTAIFYCVRDRYDGMDYWGQGTSVTVSS | 32 |

In some embodiments, antibodies of the present disclosure may be produced using one or more of the translated CDR polypeptides listed in Table 6. CDR-L1, CDR-L2, and CDR-L3 refer to CDRs present on the light chain variable domain in order of position from the N-terminus of the variable domain to the C-terminus of the variable domain. CDR-H1. CDR-H2, and CDR-H3 refer to CDRs present on the heavy chain variable domain in order of position from the N-terminus of the variable domain to the C-terminus of the variable domain. Some antibodies may be produced using translated polypeptides having at least 60%, at least 65%, at least 70%, at least 75%, at least 80%, at least 85%, at least 90%, at least 95%, at least 96%, at least 97%, at least 98%, at least 98.5%, at least 99%, or at least 99.5% sequence identity to any of those listed. Some antibodies may be produced using fragments of one or more of the amino acid sequences listed. In some embodiments, antibodies of the present disclosure include a heavy chain variable domain ($V_H$) having a CDR having at least 30%, at least 40%, at least 50%, at least 60%, at least 70%, at least 80%, or at least 90% amino acid sequence identity to an amino acid sequence selected from any of the CDR sequences presented. In some cases the heavy chain CDR is a CDR-H3. Some antibodies include $V_H$ domains, wherein the CDR-H1, CDR-H2, and CDR-H3 are all selected from any of the heavy chain CDRs presented or variants thereof having at least 30%, at least 40%, at least 50%, at least 60%, at least 70%, at least 80%, or at least 90% sequence identity to one or more of the heavy chain variable domains presented. In some embodiments, antibodies of the present disclosure include a light chain variable domain (VL) having a CDR having at least 30%, at least 40%, at least 50%, at least 60%, at least 70%, at least 80%, or at least 90% amino acid sequence identity to an amino acid sequence selected from any of the CDR sequences presented. In some cases the light chain CDR is a CDR-L3. Some antibodies include VL domains, wherein the CDR-L1, CDR-L2, and CDR-L3 are all selected from any of the light chain CDRs presented or variants thereof having at least 30%, at least 40%, at least 50%, at least 60%, at least 70%, at least 80%, or at least 90% sequence identity to one or more of the light chain variable domains presented.

TABLE 6

CDR sequences

| Antibody | CDR | Sequence | SEQ ID NO |
|---|---|---|---|
| D2 | CDR-LI | ONIVYSDGNTY | 33 |
| D3 | CDR-LI | QNIVYSDGNTY | 33 |
| H9 | CDR-LI | QSLVHSNGNTY | 34 |
| D2 | CDR-L2 | KVS | 35 |
| D3 | CDR-L2 | KVS | 35 |
| H9 | CDR-L2 | KVS | 35 |
| D2 | CDR-L3 | LOGSHVPPT | 36 |
| D3 | CDR-L3 | LOGSHVPPT | 36 |
| H9 | CDR-L3 | SQSTHVPFT | 37 |
| D2 | CDR-H1 | GYTFTSYW | 38 |
| D3 | CDR-H1 | GYTFTSYW | 38 |
| H9 | CDR-H1 | GFTFSSYG | 39 |
| D2 | CDR-H2 | IYPSDSYT | 40 |
| D3 | CDR-H2 | TYPSDSYT | 40 |
| H9 | CDR-H2 | ISSGGSYT | 41 |
| D2 | CDR-H3 | ARERYERDAMDY | 42 |
| D3 | CDR-H3 | ARERYERDAMDY | 42 |
| H9 | CDR-H3 | VRDRYDGMDY | 43 |

In some embodiments, antibodies of the present disclosure may include one or more of the constant region amino acid sequences listed in Table 7. Some antibodies may include constant domain amino acid sequences having at least 60%, at least 65%, at least 70% at least 75, at least 80, at least 85%, at least 90%, at least 95%, at least 96, at least 97%, at least 98%, at least 98.5%, at least 99%, or at least 99.5% sequence identity to any of those listed. Some antibodies may include constant domains that include fragments or variants of one or more of the amino acid sequences listed.

TABLE 7

Constant region sequences

| Antibody | Leader, Variable domain | Sequence | SEQ ID NO. |
|---|---|---|---|
| D2 | Constant region, Light chain | RADAAPTVSIFPPSSEQLTSGGASVVCF LNNFYPKDINVKWKIDGSERQNGVLN SWTDQDSKDSTYSMSSTLTLTKDEYER HNSYTCEATHKTSTSPIVKSFNRNEC | 44 |
| D3 | Constant region, Light chain | RADAAPTVSIFPPSSEQLTSGGASVVCF LNNFYPKDINVKWKIDGSERQNGVLN SWTDQDSKDSTYSMSSTLTLTKDEYER HNSYTCEATHKTSTSPIVKSFNRNEC | 44 |
| H9 | Constant region, Light chain | RADAAPTVSIFPPSSEQLTSGGASVVCF LNNFYPKDINVKWKIDGSERQNGVLN SWTDQDSKDSTYSMSSTLTLTKDEYER HNSYTCEATHKTSTSPIVKSFNRNEC | 44 |
| D2 | Constant region, Heavy chain | AKTTPPSVYPLAPGSAAQTNSMVTLGC LVKGYFPEPVTVTWNSGSLSSGVHTFP AVLQSDLYTLSSSVTVPSSTWPSETVT CNVAHPASSTKVDKKIVPRDCGCKPCI CTVPEVSSVFIFPPKPKDVLTITLTPKVT CVVVDISKDDPEVQFSWFVDDVEVHT AQTQPREEQFNSTFRSVSELPIMHQDW LNGKEFKCRVNSAAFPAPIEKTISKTKG RPKAPQVYTIPPPKEQMAKDKVSLTC MITDFFPEDITVEWQWNGQPAENYKN TOPIMDTDGSYFVYSKLNVQKSNWEA GNTFTCSVLHEGLHNHHTEKSLSHSPG K | 45 |
| D3 | Constant region, Heavy chain | AKTIPPSVYPLAPGSAAQTNSMVTLGC LVKGYFPEPVTVTWNSGSLSSGVHTFP AVLQSDLYTLSSSVTVPSSTWPSETVT CNVAHPASSTKVDKKIVPRDCGCKPCI CTVPEVSSVFIFPPKPKDVLTITLTPKVT CVVVDISKDDPEVQFSWFVDDVEVHT AQTQPREEQFNSTFRSVSELPIMHQDW LNGKEFKCRVNSAAFPAPIEKTISKTKG RPKAPQVYTIPPPKEQMAKDKVSLTC MITDFFPEDITVEWQWNGQPAENYKN TOPIMDTDGSYFVYSKLNVQKSNWEA GNTFTCSVLHEGLHNHHTEKSLSHSPG K | 45 |
| H9 | Constant region, Heavy chain | AKTTPPSVYPLAPGSAAQTNSMVTLGC LVKGYFPEPVTVTWNSGSLSSGVHTFP AVLQSDLYTLSSSVTVPSSTWPSETVT CNVAHPASSTKVDKKIVPRDCGCKPCI CTVPEVSSVFIFPPKPKDVLTITLTPKVT CVVVDISKDDPEVQFSWFVDDVEVHT AQTQPREEQFNSTFRSVSELPIMHQDW LNGKEFKCRVNSAAFPAPIEKTISKTKG RPKAPQVYTIPPPKEQMAKDKVSLTC MITDFFPEDITVEWQWNGQPAENYKN TOPIMDTDGSYFVYSKLNVQKSNWEA GNTFTCSVLHEGLHNHHTEKSLSHSPG K | 45 |

Epitopes and Fragments

In some embodiments, capture antibodies bind to epitopes that include or are present on hCD59 fragments and/or variants described in International Publication Number WO2015084994. Such fragments and/or variants may include: FEHCNFNDVTTRLRENELTYYCCKKDL (SEQ ID NO: 46); FEHCNFNDVTTRLRENELTYYCCKK (SEQ ID NO: 47); HCNFNDVTTRLRENELTYYCCKK (SEQ ID NO: 48); ACNFNDVTTRLRENELTYYCAAK (SEQ ID NO: 49); Ac-ACNFNDVTTRLRENELTYYCAAK-NH$_2$ (SEQ ID NO: 50, Ac is an acetyl group and NH$_2$ is an amine group): AFEHCNFNDVTTRLRENELTYYCAAKDL (SEQ ID NO: 51); AFEHCNFNDVTTRLRENELTYYC (βA)KDL (SEQ ID NO: 52, βA is β-alanine); or AFEHCNFNDVTTRLRENELTYYC(Aib)AKDL (SEQ ID NO: 53, Aib is alpha-amino-isobutyric acid). In some embodiments, these fragments and/or variants may include disulfide bonds between cysteine residues. In some embodiments, these fragments and/or variants may include or exclude N- and/or C-terminal groups (e.g., hydroxyl groups "—OH," acetyl groups "Ac-" or amine groups "—NH$_2$"). In some embodiments, capture antibodies are generated by immunizing mammals with any of these fragments and/or variants and isolating resulting antibodies from immunized mammals or from antibody-producing cells obtained from immunized mammals. In some embodiments, capture antibodies are produced recombinantly or synthetically from antibody amino acid or nucleic acid sequences obtained from immunized mammals or from antibody-producing cells obtained from immunized mammals.

In some embodiments, detection antibodies bind to epitopes that include or are present on glycated CD59 fragments and/or variants described in International Publication Number WO2015084994. Such fragments and/or variants may include: NKCWKFEHCNFNDV (SEQ ID NO: 54); WKFEH (SEQ ID NO: 55); NKAWKFEHANFND (SEQ ID NO: 56): Ac-NKAWKFEHANFNDC-OH (SEQ ID NO:57, Ac is an acetyl group and OH is a hydroxyl group). In some embodiments, these fragments and/or variants may include or exclude N- and/or C-terminal groups (e.g., hydroxyl groups "—OH," acetyl groups "Ac-" or amine groups "—NH$_2$"). The fragments and/or variants may include glycated lysine residues. Glycated residues may include different arrangements of chemical bonds and stereochemical structures. Such residues may include structures or intermediate forms occurring during lysine glycation and/or rearrangement. Glycated residues may include any of structures I-VII shown below.

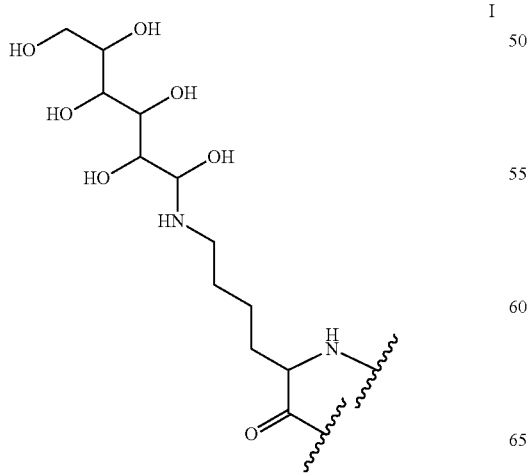

I

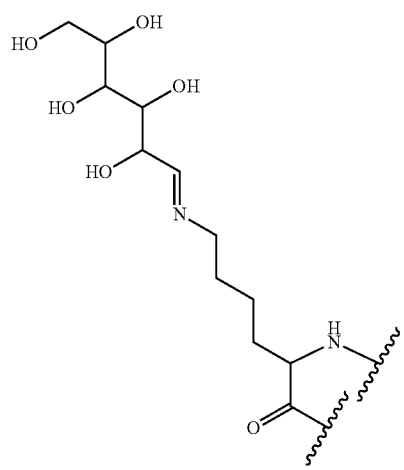

II

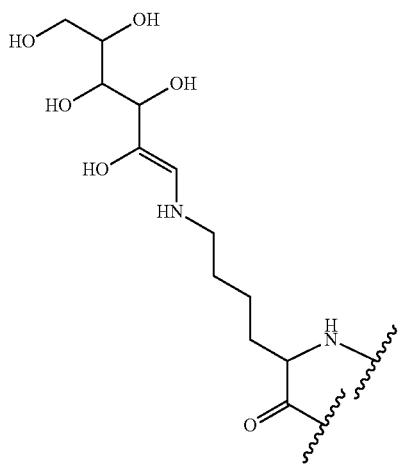

III

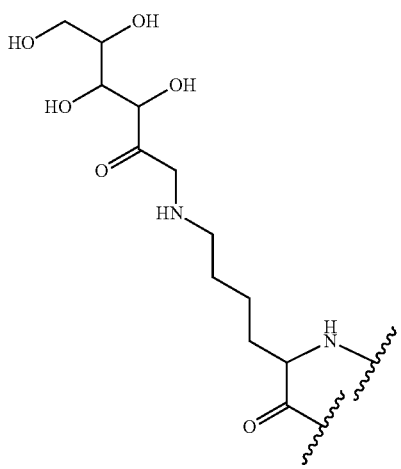

IV

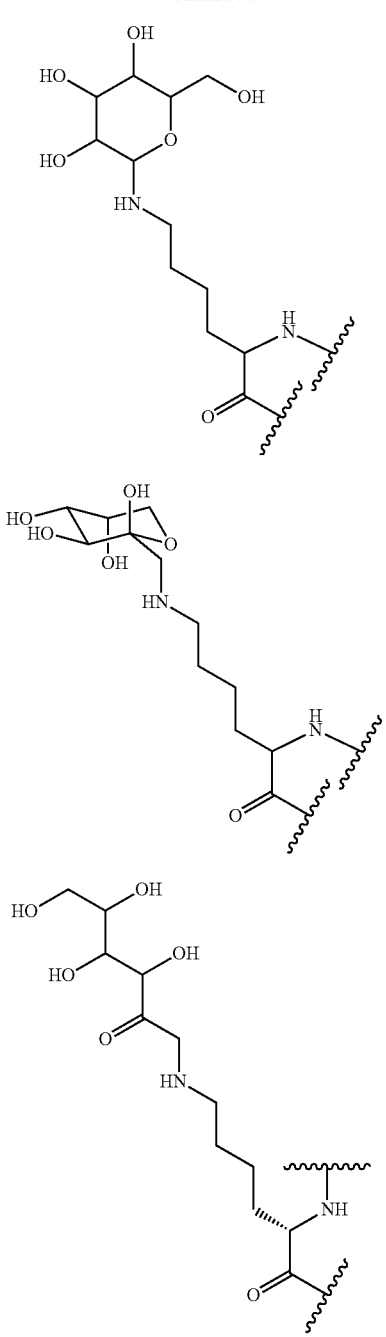

In some embodiments, detection antibodies are generated by immunizing mammals with any of the fragments and/or variants of glycated CD59 presented above and isolating resulting antibodies from immunized mammals or from antibody-producing cells obtained from immunized mammals. In some embodiments, detection antibodies are produced recombinantly or synthetically from antibody amino acid or nucleic acid sequences obtained from immunized mammals or from antibody-producing cells obtained from immunized mammals.

Modulators of K41 Glycation

In some embodiments, present disclosure provides compounds for modulating glycation of CD59, referred to herein as "glycation modulators." Glycation modulators may include, but are not limited to, small molecules, peptides, synthetic constructs, fusion proteins, aptamers, nucleic acids, and antibodies. Some glycation modulators may modulate glycation of residue K41 of hCD59. Some glycation modulators may modulate CD59 glycation without inhibiting the function of CD59 as a complement regulator. Glycation modulators inhibiting glycation of residue K41 of hCD59 are referred to herein as "K41 glycation inhibitors." K41 glycation inhibitors may, for example, bind to or otherwise interact with K41 or one or more residues near K41 (e.g., near K41 along the length of the polypeptide and/or near K41 due to secondary and tertiary protein structures). In some embodiments, K41 glycation inhibitors may physically block glycation at K41 or may alter the hCD59 protein conformation in a way that prevents K41 from becoming glycated. Some K41 glycation inhibitors may bind to residue H44 of hCD59 and block chemical reactions necessary for K41 glycation.

In some embodiments, K41 glycation inhibitors may include antibodies disclosed herein. Such antibodies may physically block glycation at K41 or may alter the hCD59 protein conformation in a way that prevents K41 from becoming glycated. Some antibodies may inhibit K41 glycation, for example, by targeting H44 of human hCD59. In some embodiments, such antibodies may block chemical reactions necessary for K41 glycation.

II. Methods of Use

Methods of the disclosure include methods of detecting the presence, measurement of levels, and or changes in levels of various factors described herein. Such factors may include, but are not limited to, target proteins, post-translational modifications, and standard agents. "Levels" may refer to an actual number of factors detected, a concentration of a factor, or a relative level (e.g., through comparison of detection signals between a detected factor and a surrogate factor or standard agent). Such methods may include the use of capture agent to capture CD59. As used herein, the term "capture agent" refers to any compound capable of binding an assay component (e.g., assay target protein or compound). Capture agents may include capture antibodies. Capture antibodies may include any of the antibodies described herein. In some cases, capture agents are lectins capable of binding glycosylated assay components.

Additional methods may include the use of a detection agent. As used herein, the term "detection agent" refers to an assay component capable of binding or otherwise indicating the presence and/or level of an analyte. In some embodiments, detection agents are antibodies (detection antibodies). Detection agents may include antibodies used to detect GCD59. Detection antibodies may include any antibodies described herein. Further detection agents may include lectins capable of detecting glycosylated assay components. Detection agents may comprise a detectable label. Such detectable labels may include, but are not limited to biotin, streptavidin, avidin, fluorescent labels, enzymatic labels, luminescent labels, and radioactive labels. In some methods, detection agents may be detected using a secondary antibody.

In some embodiments, methods of the invention may include the use of other antibodies known in the art for capturing or detecting CD59 and/or GCD59. Such antibodies may include any of those described and/or claimed in European Patent Number EP2348050, International Publication Number WO2015084994, and U.S. Pat. Nos. 9,068,006, 9,417,248, the contents of each of which are herein incorporated by reference in their entireties.

Methods may include standard immunological assay formats for capturing proteins and detecting one or more specific epitopes present on such proteins. Such epitopes may include post-translationally modified epitopes. Post-translationally modified epitopes may include glycated and/or glycosylated epitopes.

Methods may include immunological assays. As used herein, an "immunological assay" refers to any assay which utilizes at least one antibody for detection of an analyte. Immunological assays may include, but are not limited to, enzyme linked immunosorbent assays (ELISAs), immunoprecipitation assays, immunofluorescence assays, enzyme immunoassays (EIA), radioimmunoassays (RIA), and Western blot analysis. Methods of the present disclosure may include the use of surface-associated formats or solution-based formats. As used herein, the term "surface-associated format" refers to a method that includes immobilization of one or more assay components on a surface. Such surfaces may include, but are not limited to assay plates, membranes, sensors, or other substrates that include a surface. In some embodiments, the surface-associated format may include a magnetic interaction surface, bead or coated magnetic beads. In some embodiments, they may include the use of ferromagnetic labels.

As used herein, the term "solution-based format" refers to a method that includes immobilization of one or more assay components on a substrate that is able to move freely in a liquid medium. Substrates suitable for solution-based formats may include beads or other particles that are mobile in liquid media. Methods utilizing solution-based formats may be analyzed by forcing liquid media through tubes, channels, or other passageways where detection of bound analytes may be carried out. Assay components may be immobilized on surface or solution-based formats in varying levels and/or coating densities. Immobilization may be facilitated through the formation of any number of interactions that include, but are not limited to, covalent bonds, non-covalent bonds, hydrogen bonds, and hydrophobic bonds.

In some embodiments, methods of the disclosure include the use of a capture antibody to immobilize CD59 to a surface or substrate. Such methods may further include the use of a detection agent (e.g., lectin or detection antibody) to detect a specific epitope present on CD59. Such epitopes may include glycated and/or glycosylated epitopes. Glycated epitopes may include glycated K41 of hCD59. Such epitopes may include Amadori-modified K41 of GCD59. Glycosylated epitopes may include N-glycosylated epitopes on hCD59 and/or GCD59. Detection of N-glycosylated epitopes may be carried out using a lectin as a detection agent, wherein the lectin binds to such N-glycosylated eptitopes (e.g., an N-glycosylated residue of GCD59). In some embodiments, detection of N-glycosylated epitopes may be carried out using a detection antibody.

According to some methods of the present disclosure, anti-Amadori-modified GCD59 antibodies may be used as a capture antibody to immobilize GCD59 to a surface or substrate. Such methods may further include the use of a detection antibody that recognizes a non-glycated epitope of GCD59. Some methods may include the use of a detection antibody that recognizes a glycosylated epitope of GCD59. Such epitopes may include an N-glycosylated epitope of GCD59.

Methods of the disclosure may include the use of one or more internal controls. Such internal controls may include plasma assay controls. Some methods include one or more of an assay diluent, a conjugate diluent, and a wash buffer. In some cases, methods include at least one buffer having one or more of reducing agents, oxidizing agents, dithiothreitol (DTT), and/or beta-mercaptoethanol (BME).

In some embodiments, methods of the present disclosure may include the use of one or more of the antibodies described herein to carry out any of the methods described in any of European Patent Number EP2348050, International Publication Number WO2015084994, and U.S. Pat. Nos. 6,835,545, 9,068,006, 9,417,248, the contents of each of which are herein incorporated by reference in their entireties.

Methods of determining concentration levels may include comparison to a standard curve to determine concentrations of a target protein. A standard curve is a set a data obtained from samples having a range of concentrations of a standard agent. As used herein, a "standard agent" is an agent that is the same as or representative of a target protein being detected in an assay. In some embodiments, standard agents are surrogate compounds. As used herein, a "surrogate compound" is a compound that exhibits one or more features of a target protein or other molecule. Such features may include epitopes present on one or more target proteins. In some embodiments, surrogate compounds include CD59 fragments or variants thereof. In some embodiments, surrogate compounds include fragments that include SEQ ID NO: 50. In some embodiments, capture agents bind to such fragments. In some embodiments, surrogate compounds include glycated CD59 fragments or variants thereof. Glycated fragments may include SEQ ID NO: 57. Such fragments may include glycated lysine residues. In some embodiments, the glycated lysine residue includes glucitollysine. In some embodiments, the glycated lysine residue includes Amadori-modified glycated lysine. In some embodiments, detection agents bind to such fragments. Surrogate compounds may include one or more non-protein components. Such non-protein components may include linkers, labels (e.g., detectable labels), moieties, or other features not present on native or target proteins. In some embodiments, surrogate compounds may include any of those disclosed in U.S. Pat. No. 9,417,248 or U.S. Publication No. US2016/0299150, the contents of each of which are herein incorporated by reference in their entirety. Such surrogate compounds may include the compound depicted in FIG. 27 of U.S. Pat. No. 9,417,248.

In some embodiments, concentration equivalents of a target protein are used to indicate the concentration of a target protein. As used herein, a "concentration equivalent" is an indicator of concentration that is based on a comparison to a standard curve generated using a surrogate compound.

In some embodiments, methods of diagnosing, screening, and/or monitoring described herein may include comparison of factor levels from a subject to a threshold value or receiver operating characteristic (ROC) curve.

In some embodiments, the present disclosure provides methods for therapeutic, diagnostic, and monitoring applications. Such methods may include the use of one or more antibodies described herein. Such antibodies may include, but are not limited to, anti-Amadori-modified GCD59 antibodies.

Therapeutic Applications

In some embodiments, methods of the invention include therapeutic applications that may be used to treat, prevent, and/or reduce the occurrence or symptoms of one or more diseases and/or disorders in a subject. As used herein a "subject" is any person, individual, fetus, newborn, infant, animal, and/or patient. Subjects may include gestational subjects. As used herein, a "gestational subject" is a subject residing within a womb, although the term may be used to refer to a subject over a period of time that includes both periods where a subject is within and outside of a womb. For example, diagnosis of a gestational subject may refer to a diagnosis that is confirmed at the time of or after birth. As used herein, a "pregnant subject" or "gestational carrier" refers to an individual that bears a gestational subject in the subject's womb and includes individuals with or without a biological relationship with the gestational subject. As used herein, the term "infant subject" refers to subjects who are infants and embraces subjects from birth to about 1 year of age. Subjects may be undergoing treatment, may be in need of treatment, may have undergone treatment, or may be screened or stratified for possible or potential treatments. Subjects may include animals, e.g., primates, non-human primates or any animals such as farm animals and the like.

Diabetes

In some embodiments, methods of the present disclosure may be used to treat, prevent, and/or reduce the occurrence or symptoms of one or more diabetes-related indications. As used herein, the term "diabetes-related indication" refers to any disease, disorder, and/or condition related to elevated blood glucose levels, decreased cellular glucose uptake, reduced insulin levels, or reduced insulin sensitivity. Diabetes-related indications include diabetes and pre-diabetes.

In some embodiments, the present disclosure provides methods of diagnosing, monitoring, screening, and/or treating one or more diabetes-related indications that may include, but are not limited to, indications related to complement dysfunction, hemolytic disease, paroxysmal nocturnal hemoglobinuria, atypical hemolytic-uremic syndrome, wound healing, complications associated with organ transplantation, vascular indications, and age-related macular degeneration. In some embodiments, diabetes-related indications may include a pre-clinical diabetes-related indication. Pre-clinical diabetes-related indications may include, but are not limited to predisposition to an organ specific complication of diabetes, pre-clinical diabetic peripheral neuropathy, pre-clinical diabetic nephropathy, pre-clinical diabetic retinopathy, and pre-clinical diabetic vascular disease.

Diabetes is a disease characterized by elevated blood glucose levels, also referred to as hyperglycemia. Insulin, along with other hormones including, but not limited to glucagon and epinephrine, is critical for maintenance of normal glucose levels in the blood. Insulin binding to cellular receptors facilitates cellular uptake of glucose, providing an energy source for cells and lowering glucose levels in the blood (Rodger, W., CMAJ. 1991. 145(10):1227-37). Insulin is expressed by pancreatic p cells and its expression is upregulated when blood glucose levels rise. In diabetes, insulin levels and/or sensitivity to insulin are disrupted, reducing cellular glucose uptake and elevating circulating levels of glucose. The two primary forms of diabetes are insulin-dependent (also referred to herein as juvenile diabetes or Type I diabetes) and insulin-independent (also referred to herein as adult-onset diabetes or Type II diabetes). Type I diabetes is less common and typically brought on by autoimmune destruction of p cells, the primary source of insulin. 90% or more of those with diabetes suffer from Type II diabetes. This form of the disease is characterized by reduced insulin secretion and/or reduced sensitivity to insulin (e.g., reduced ability of insulin to stimulate glucose uptake in cells) (Rodger, W., Non-insulin-dependent (Type II) diabetes mellitus. CMAJ. 1991. 145(12)1571-81). Type II diabetes is thought to occur in part due to genetic susceptibility and occurs most often in subjects who are overweight and/or obese.

The term "diabetic" as used herein, refers to an individual comprising one or more types of insulin deficiency (e.g., reduced insulin levels and/or reduced insulin sensitivity). The term diabetic includes, but is not limited to, individuals with juvenile diabetes (Type I diabetes), adult-onset diabetes (Type II diabetes), gestational diabetes mellitus (GDM), and any other conditions of insulin deficiency. The term "diabetic" is a term of art, known and understood by those practicing in the medical profession, a formal definition of which can be found in Harrison's Principles of Medicine (Harrisons, Vol 14, Principles of Internal Medicine, Eds. Fauci, A. S., E. Braunwald. K. J. Isselbacher, J. D. Wilson. J. B. Martin, D. L. Kasper, S. L. Hauser, D. L. Longo, McGraw-Hill, New York, 1999).

Gestational Diabetes Mellitus (GDM)

In some embodiments, methods of the present disclosure may be useful in the detection, diagnosis and/or prognosis of gestational diabetes mellitus (GDM). As used herein, the terms "gestational diabetes mellitus" or "GDM" refer to a diabetic condition characterized by elevated blood glucose levels, carbohydrate intolerance and/or reduced insulin sensitivity that is brought on by pregnancy. In some cases, GDM diagnosis in each country may rely on different standards set by the professional bodies from such countries that issue recommendations to physicians practicing there. GDM may affect up to 18% of pregnancies with adverse outcomes that affect both the mother and offspring, including both short term and long term effects. Currently, diagnosis and monitoring of GDM in pregnant female subjects relies heavily on the measurement of blood glucose levels. Blood glucose is in constant flux and influenced by a number of external factors including meals and level of activity. Glucose levels may change on an hourly basis. This complicates GDM testing by imposing diet requirements and/or restrictions on subjects undergoing testing.

GDM is one of the most prevalent disorders affecting pregnant women and carries with it a greater risk for complications during pregnancy, at the time of birth and even after birth. Additionally, such complications may affect both mother and offspring. Individuals with GDM lack the ability to adequately break down carbohydrates into energy (Okun, N., Can. Fam. Physician. 1997. 43:88-93). In some cases, GDM diagnosis may be carried out through the detection of high blood glucose levels and/or through the observation of a decreased ability to respond to a glucose challenge during pregnancy. Such diagnosis occurs most often in the third trimester. Although mechanisms leading to GDM are still unclear, in some cases, it is believed that hormones that become elevated during pregnancy may interfere with normal insulin signaling, including, but not limited to insulin resistance. This insulin signaling dysfunction leads to decreased cellular glucose uptake and elevated blood glucose levels. GCD59 levels may be elevated in subjects displaying different levels of glucose intolerance including those diagnosed with GDM.

GDM Screening and Diagnosis

GDM is one of the most common medical complications of pregnancy. In each country, GDM diagnosis may be determined by standards set by professional bodies responsible for issuing recommendations to practicing physicians. There is ongoing debate among professional bodies within the United States as well as between professional bodies in the United States and those abroad as to how to approach GDM diagnosis. Such US professional bodies may include, but are not limited to the National Institutes of Health (NIH), the American Diabetes Association (ADA) and the American Congress of Obstetricians and Gynecologists (ACOG).

Such International bodies may include, but are not limited to the International Association of Diabetes and Pregnancy Study Groups (IADPSG). Professional bodies in the US and abroad may tailor their approaches based on different studies, different analysis of such studies and may be affected by health care and economic pressures. Indeed, factors for defining GDM and criteria for diagnosis may change over time. As such, in some embodiments, methods of the present disclosure, described herein, may be conducted in accordance with the most current recommendations issued by professional bodies in each country involved in the health of pregnant women, fetuses, and newborns.

According to some current US practices, screening of all pregnant women for GDM is suggested. In some cases, screening may comprise a review of patient history, assessment of clinical risk factors and/or one or more tests comprising a glucose challenge. As used herein, the term "glucose challenge" refers to a testing component characterized by the administration of glucose to a subject. Glucose challenge testing typically assesses the response in subjects to a glucose challenge. This may comprise analyzing blood glucose levels. The amount of glucose administered during a glucose challenge may vary. Typical tests comprise the administration of from about 50 g to about 100 g of glucose. In other embodiments, 75 g of glucose are administered. In some cases, plasma glucose levels may be assessed after one or more glucose challenge or after a meal. In some embodiments, methods of the present disclosure related to GCD59 detection may be carried out with subjects with or without fasting. Some methods may be carried out with subjects with or without glucose challenge.

"Low risk" pregnant subjects, at the lowest risk of developing GDM, comprise those who are less than 25 years old, have normal body mass index, have no family history of diabetes (at the level of first-degree relatives.) do not have a history of abnormal glucose metabolism, do not have a history of poor obstetric outcome and are not of a high risk ethnicity (e.g. Hispanic, Native American, African American and South Asian). Pregnant subject risk assessment is typically carried out during a first prenatal visit. Women at higher risk of developing GDM (e.g., obese, personal history of GDM, glycosuria, family history of diabetes, etc.) typically undergo testing as soon as possible. If initial tests in such women are negative, retesting is recommended between the $24^{th}$ and $28^{th}$ weeks of pregnancy.

High plasma glucose levels may be indicative of GDM in the absence of a glucose challenge. Some methods disclosed herein comprise fasting glucose tests. According to such tests, fasting plasma glucose (FPG) levels may be determined. Fasting plasma glucose levels refer to levels of glucose measured directly after a period of fasting. Periods of fasting may be from about 1 hour to about 24 hours. In certain embodiments, FPG levels may be measured after about 12 hours of fasting. According to the American diabetes Association (ADA) recommendation for standard of medical care diagnosis of GDM at 24-28 weeks of gestation should be made when FPG≥92 mg/dL (5.1 mmol/L) in women not previously diagnosed with overt diabetes (ADA, Diabetes Care, 37, (Suppl 1), S14-S80, 2014). According to International Association of Diabetes and Pregnancy Study Group (IADPSG) recommendations diagnosis of GDM at the first prenatal visit should be made when FPG≥92 mg/dL (5.1 mmol/L) but <126 mg/dL (7.0 mmol/L) (Metzger B E, Diabetes Care, 33, 676, 2010). In some embodiments, methods described herein for assessing GCD59 in subjects may be carried out in combination with assessments of FPG. Some methods of the present disclosure may be carried out prior to or in response to determinations of FPG levels falling within or outside of GDM diagnosis levels recognized by the ADA and/or IADPSG.

In some embodiments, random glucose tests may be conducted. Such tests measure random plasma glucose levels (also referred to as casual plasma glucose levels). Random glucose levels refer to glucose levels obtained without any consumption restrictions and/or requirements (e.g., fasting). In pregnant subjects, random plasma glucose levels that are greater than 200 mg/dl indicate GDM in such subjects. In certain embodiments, a second measurement is required the next day for both FGP levels and random plasma levels to confirm diagnosis of GDM. In some embodiments of the present invention, GCD59 levels may also be obtained without consumption restrictions and/or requirements (e.g., fasting).

In cases where hyperglycemia is subtle, other approaches may be necessary for diagnosis. In pregnant subjects identified as being high risk, the one-step approach may be sufficient. According to the one-step approach, diagnosis may be carried out by oral glucose tolerance testing (OGTT) without any prior blood glucose screening. For individuals of average risk, the two-step approach is typically carried out. According to the two-step approach, an initial screening comprising a glucose challenge is carried out. In initial screenings of the two-step approach, Recommendations by the American College of Obstetricians made in 2001 call for a 50 g, one-hour oral glucose challenge test (GCT) to be used (Committee on Obstetric Practice. The American College of Obstetricians and Gynecologists: Committee Opinion. 2011). The one hour oral GCT measures blood glucose concentrations 1 hour after the oral administration of 50 g of glucose. 80% of pregnant subjects with GDM comprise blood glucose levels above the cut-off value of 130 mg/dl and 90% comprise levels above the cut-off value of 140 mg/dl. As used herein, the term "cut-off value" refers to a value or level at which an indication may be made with regard to a diagnostic determination or other type of determination, wherein a level below a given cut-off leads to a determination that is different from a determination based on a level above a given cut-off (American Diabetes Association, Diabetes Care. 31(1): S62-S67).

In the second step of the two-step approach, a 100 g OGTT may be carried out. As used herein, the term "oral glucose tolerance test" or "OGTT" refers to a test that measures the ability of the body to utilize glucose. Such testing typically begins in the morning, wherein the subjects have not eaten for 8-12 hours. A baseline concentration is established based on an initial blood sample. As used herein, the term "baseline" when referring to measurements, levels or values refers to an initial measurement, level or value to which subsequent measurements, levels or values may be compared. After the initial blood sample is taken, subjects are given a glucose solution to drink with a measured concentration of glucose. In the 100 g OGTT, 100 g of glucose is administered in the glucose solution. Subjects are typically required to finish the drink within a 5-minute time frame. Finally, OGTTs comprise the obtaining of subsequent blood samples to monitor blood glucose and/or insulin levels. According to the 100 g OGTT, diagnosis of GDM in pregnant subjects may be made when subject blood glucose levels exceed a cut-off value of 95 mg/dl for baseline readings, a cut-off value of 180 mg/dl one hour after glucose administration, a cut-off value of 155 mg/dl two hours after glucose administration and/or a cut-off of 140 mg/dl three hours after glucose administration. In some embodiments, a diagnosis of GDM may require that two out of four tests yield elevated blood glucose levels (e.g., according to any of the assessments described herein).

In some cases, a 75 g OGTT is carried out in the second step of the two step approach to GDM diagnosis. The 75 g OGTT may be carried out according to the 100 g OGTT with the exception that only 75 g of glucose is administered. According to the 75 g OGTT, diagnosis of GDM in pregnant subjects may be made when subject blood glucose levels exceed a cut-off value of 95 mg/dl for baseline readings, a cut-off value of 180 mg/dl one hour after glucose administration and/or a cut-off value of 155 mg/dl two hours after glucose administration. In some embodiments, a diagnosis of GDM may require that two out of four tests yield elevated blood glucose levels.

In some cases, the 2-hour postprandial glucose test is carried out during GDM screening. 2-hour postprandial glucose testing comprises the analysis of blood glucose levels 2 hours after a meal.

In some cases, 1,5-anhydroglucitol testing may be carried out during GDM screening. Levels of 1,5-anhydroglucitol levels are reduced during periods of hyperglycemia (wherein blood glucose levels are above 180 mg/dl), requiring up to 2 weeks to return to normal after hyperglycemic conditions have ended (McGill, J. B. et al., Diabetes Care. 2004. 27(8):1859-65). 1,5-anhydroglucitol testing may be done to determine whether subject have endured extended periods of hyperglycemia.

In some cases, hemoglobin A1c (HbA1c) testing may be carried out during GDM screening. Such testing measures the level of a glycated version of hemoglobin, HbA1c in the blood. HbA1c levels increase during periods of hyperglycemia. HbA1c remains in the blood from about 8 to about 12 weeks until red blood cells comprising HbA1c are replaced, making HbA1c a good longer term reading of overall blood glucose levels during that period (http://medweb.bham.ac.uk/easdec/prevention/what_is_the_hba1c.htm).

In some embodiments, fructosamine testing may be carried out during GDM screening. Fructosamine levels become elevated under hyperglycemic conditions. Elevated levels of fructosamine remain elevated for two to three weeks after hyperglycemic conditions subside, making them a good longer term indicator of high blood glucose levels (Delpierre, G. et al., Biochem J. 2002. 365:801-8).

In some embodiments, subject samples may be obtained and analyzed prior to pregnancy. Such subject samples may be obtained from a female subject. Subject samples may also be used to determine a level of risk of developing GDM and/or pre-eclampsia in a current and/or future pregnancy.

In some embodiments, methods of the present disclosure may be combined with any of the tests described herein. Such tests may include, but are not limited to glucose challenge testing, oral glucose tolerance testing, fasting glucose testing, random glucose testing, 2-hour postprandial glucose testing, hemoglobin A1c (HbA1c) testing, fructosamine testing and 1,5-anhydroglucitol testing. In some embodiments, methods of the present disclosure may be combined with such tests for the purposes of diagnosis, prognosis and/or monitoring of GDM or other diabetic conditions. In some embodiments, methods of the present disclosure may be used for post-partum screening for type-2 diabetes.

In some embodiments, methods of the present disclosure may be combined with detection of other glycated proteins. Many other proteins present within bodily fluids comprise amino groups that may be capable of being glycated. Such proteins may include glycated albumin, glycated hemoglobin, glycated immunoglobulins, glycated hemopexin, glycated vitamin D binding protein, glycated fibrinogen alpha chain, glycated apolipoprotein A1, glycated transferrin, glycated macroglobulin alpha 2, glycated complement component 4A, glycated fibrinogen beta chain, glycated fibrinogen alpha chain, glycated abhydrolase domain-containing protein 14B, glycated amiloride-sensitive amine oxidase copper-containing precursor, glycated angiotensin-converting enzyme isoform 1 precursor, glycated peptidase family M2 Angiotensin converting enzyme, glycated aconitase 1, glycated lysosomal acid phosphatase isoform 1 precursor, glycated pancreatitis-associated protein, glycated alpha-actinin-4, glycated metalloproteinase with thrombospondin type 1 motifs, glycated aspartylglucosaminidase, glycated adenosylhomocysteinase, glycated alpha-2-HS-glycoprotein, glycated alcohol dehydrogenase $NADP^+$, glycated aldo-keto reductase family 1, glycated aldehyde dehydrogenase family 1 member L1, glycated aldolase B fructose-bisphosphate, glycated pancreatic amylase alpha 2A, and glycated apolipoprotein A4 (Ukita et al., Clin. Chem. (1991) 37:504; Johansen et al., Glycobiol. (2006) 16:844; and Davies et al., J. Exp. Med. (1989) 170:637). In some embodiments. GCD59 may be detected as part of a panel or array of biomarkers comprising any of the glycated proteins listed above.

GDM Categories

In some embodiments, pregnant subjects may be placed into different subcategories of disease based on certain criteria. Two such categories include those with impaired glucose tolerance (IGT) and those with impaired fasting glucose (IFG). These categories are designated for subjects whose glucose levels are above normal, but do not rise to the level of GDM or that fall short of the requirement for GDM diagnosis. Factors determining placement of subjects into such categories may be different for each country and may be controlled by professional bodies in such countries responsible for providing recommendations to physicians practicing in such countries.

In some embodiments, pregnant subjects may be diagnosed with IFG when fasted glucose levels in such subjects comprise from about 100 mg/dl to about 125 mg/dl as compared to those with normal fasted glucose levels (e.g., less than 92 mg/dL according to assessments described previously) and those whose levels lead to a provisional diagnosis of GDM [in some cases with levels≥92 mg/dL (5.1 mmol/L), or with levels≥92 mg/dL (5.1 mmol/L) but <126 mg/dL (7.0 mmol/L)]. In some cases, pregnant subjects may be diagnosed with IGT after OGTT results. In some cases, pregnant subjects with IGT may comprise blood glucose levels from about 140 mg/dl to about 199 mg/dl two hours after glucose administration as compared to those with normal levels (in some cases with levels less than 140 mg/dl) and those whose levels lead to a provisional diagnosis of GDM (in some cases with levels greater than 200 mg/dl).

In some embodiments, pregnant subjects with IGT and/or IFG are referred to as having pre-diabetes. As used herein, the term "pre-diabetes" refers to a condition characterized by high risk for developing diabetes (American Diabetes Association, Diabetes Care. 2008. 31(1): S62-S67). Factors determining designation of subjects into the category of pre-diabetes may be different for each country and may be controlled by professional bodies in such countries responsible for providing recommendations to physicians practicing in such countries.

In some cases, pregnant subjects suffering from GDM may be assigned to a category comprising a class of GDM developed by Dr. Priscilla White, referred to herein as "White's GDM class" (Dunn, P. M., Dr. Priscilla White (1900-1989) of Boston and pregnancy diabetes. Arch Dis Child Fetal Neonatal Ed. 2004 May; 89(3): F276-8, herein incorporated by reference in its entirety). Such GDM classes may include any of those listed in Table 8.

TABLE 8

GDM classes

| Class | Description |
|---|---|
| A1 | insulin independent |
| A2 | insulin dependent |
| B | diabetic <10 years, onset after age 20 |
| C | diabetic 10-19 years, onset between ages 10-19, no vascular complications |
| D | diabetic >20 years, onset before age 10, with vascular complications |
| F | with nephropathy |
| R | with retinopathy |
| T | with prior kidney transplant |
| H | with heart disease |

White's GDM classes include Class A1, Class A2, Class B, Class C, Class D, Class F, Class R, Class T and Class H. Of these, Class A1 and Class A2 are used to classify subjects with GDM, but not pre-existing diabetes. The other Classes are used to categories pregnant subjects that suffer from diabetes that developed at some point prior to pregnancy.

In some embodiments, GDM may be categorized according to two or more levels of GDM severity. As used herein, the term "level of GDM severity" refers to a category of disease characterized by different levels of complications or negative outcomes, typically from less severe to more severe. GDM severity may be assigned based on the level of one or more factors that correlate with such complications or negative outcomes. In other embodiments, GDM severity may be assigned based on the metabolism of blood glucose. GDM severity may also be determined by levels of GCD59. In such embodiments, mild, moderate and severe GDM levels may be assigned to subjects depending on where concentration levels of GCD59, obtained from subject samples, fall between predetermined cut-off values.

Preliminary Indications and Risk Factors

Typically, there are no symptoms for GDM. In some cases, symptoms do occur and include, but are not limited to thirst, fatigue, nausea, vomiting, bladder infection, yeast infection and blurred vision (http://www.nlm.nih.gov/medlineplus/ency/article/000896.htm). Preliminary indications of disease typically involve test results (e.g., elevated glucose levels, elevated levels of glycated proteins).

Risk factors for GDM may include, but are not limited to elevated body mass index (BMI), family history of diabetes or GDM, advanced maternal age, a history of polycystic ovary syndrome, a history of smoking, a history of obstetric issues, high cholesterol, short stature and ethnicity (Ross, G., Australian Family Physician. 2006. 35(6):392-6; Bjorge, T. et al., Am J Epid. 2004. 160(12):1168-76; Ma, R. M, at al., Diabetes Care. 2007. 30(11):2960-1). In some cases, the presence or absence of risk factors may influence one or more course of action with regard to testing and/or treatment of female subjects.

As used herein, the term "body mass index" refers to a number calculated from a subject's weight and height that correlates with the level of body fat of a given subject. This value is obtained from a subject by dividing the weight of the subject in kilograms by (height)$^2$ in meters. In some cases, BMI values may be interpreted as follows: below 18.5 kg/m$^2$—underweight; 18.5 kg/m$^2$-24.9 kg/m$^2$—normal; 25.0 kg/m$^2$-29.9 kg/m$^2$—overweight; 30.0 kg/m$^2$-34.9 kg/m$^2$—grade I obesity; 35.0 kg/m$^2$-39.9 kg/m$^2$—grade II obesity and above 40 kg/m$^2$—grade III obesity. According to such interpretations, subjects who are overweight comprise a 2.14-fold increased risk of developing GDM (Yessoufou, A. et al., Experimental Diabetes Research. 2011. 2011:1-12). Subjects who are obese comprise a 3.56-fold increased risk of developing GDM and subjects who are severely obese comprise an 8.56-fold increased risk of developing GDM. BMI interpretations may be different in each country and may be determined by professional bodies responsible for setting guidelines for physicians practicing within such countries and/or governing bodies.

Pregnant subjects with a history of pre-diabetes and/or GDM have a higher risk of developing GDM. Additionally, pregnant subjects with a family history of diabetes, pre-diabetes and/or GDM have a higher risk of developing GDM. Subject history and/or family history are typically reviewed during the first prenatal appointment. In some embodiments, subject history and/or family history may be used to make decisions about subject testing and/or treatment.

Advanced maternal age is also a risk factor for developing GDM. The percent of pregnant subjects with GDM varies among different age groups (Ross, G., Australian Family Physician. 2006. 35(6):392-6). About 1% of pregnant subjects under 20 develop GDM during pregnancy, while about 1.8% of pregnant subjects from ages 20 to 24 develop GDM, about 2.5% of pregnant subjects from ages 25 to 29 develop GDM, about 4.1% of pregnant subjects from ages 30 to 34 develop GDM, about 6.5% of pregnant subjects from ages 35 to 39 develop GDM, about 9.8% of pregnant subjects from ages 40 to 45 develop GDM and about 12.8% of pregnant subjects over 45 develop GDM.

Rates of GDM are also influenced by ethnicity with higher incidence in pregnant subjects who are African American, Native American, Hispanic and South Asian (including, but not limited to Pacific Islanders) (Kim, S. Y. et al., Prev Chronic Dis. 2012. 9; E88).

GDM-Related Conditions

GDM is a major cause of peri- and post-natal complications for mothers and their offspring. Gestational carriers afflicted with GDM may have or be at risk for developing one or more GDM-related conditions. As used herein, a "GDM-related condition" is any disorder in a gestational carrier or gestational subject associated with or resulting from GDM. GDM-related conditions in gestational carriers may include, but are not limited to complications at delivery, increased number of C-sections, risk of pre-eclampsia/eclampsia, miscarriage and/or post-pregnancy diabetes. Gestational subjects and/or infant subjects born to gestational carriers afflicted with GDM may have or be at risk for developing one or more GDM-related conditions that include, but are not limited to, macrosomia, large for gestational age (LGA), birth defects, birth trauma, hyperbilirubinemia, hypoglycemia, seizures and still birth. In some embodiments, methods of the present disclosure used to diagnose, assess, monitor, or stratify risk (i.e., assigning a level of risk to one or more subjects) for GDM in a gestational carrier may be used to identify gestational subjects and/or infant subjects at risk for developing one or more GDM-related conditions.

GDM-related conditions affecting gestational and/or infant subjects may include macrosomia. As used herein, the term macrosomia refers to a condition in infant subjects characterized by large birth weight. Large birth weight, as used herein refers to birth weights above about 8 pounds, 13 ounces or roughly above 4 kg. Infant subjects characterized with macrosomia comprise about 10% of total births. Often, abnormal or difficult childbirth (also referred to herein as dystocia) and/or birth trauma associated with infant subjects born to pregnant subjects with GDM are due to the large size of such infant subjects, causing physical stress during birth to both the mother and offspring (Najafian, M. et al., Obstetrics and Gynecology. 2012. 2012:353791). In pregnant subjects suffering from GDM, elevated blood glucose levels typically lead to increased glucose and nutrient transport across the placenta to the developing offspring (Yessoufou, A. et al., Experimental Diabetes Research. 2011. 2011:1-12). Excess nutrient levels in the developing offspring may also put such offspring in danger of developing hypoglycemia, or low blood glucose, after birth. Increased nutrient levels in utero lead to elevated insulin production by developing offspring. After birth, the transfer of placental nutrients ceases, and elevated circulating insulin in infant subjects causes blood glucose levels to drop leading to hypoglycemia. In some embodiments, methods of the present disclosure used to diagnose, assess, monitor, or stratify risk for GDM may be used to diagnose, assess, monitor and/or stratify risk for developing macrosomia.

GDM-related conditions may include large for gestational age (LGA). Large for gestational age refers to a condition characterized by birthweights that exceed the 90$^{th}$ percentile at a given gestational age. Although threshold weights may vary for this, generally, babies larger than about 8 pounds and 13 ounces when born at full term fall into the category of LGA. Where a gestational carrier has GDM, LGA may result from excess insulin produced by the fetus in response to high blood glucose levels in the gestational carrier that leads to greater than normal growth and subsequently elevated birth weight. In some embodiments, methods of the present disclosure used to diagnose, assess, monitor, or stratify risk for GDM may be used to identify gestational subjects at risk for developing LGA.

Pregnancy-related hypertensive disorders, such as pre-eclampsia have also been shown to be related to GDM (Feig, D. S. et al., PLoS Med. 2013. 10(4): e1001425.) Pre-eclampsia is a serious medical condition in pregnant subjects characterized by elevated blood pressure and proteinuria (protein in the urine). Studies indicate that pregnant subjects with GDM have a higher risk of developing pre-eclampsia. It has also been shown that the risk of pre-eclampsia increases with intolerance to glucose. Additionally, pregnant subjects with pre-eclampsia have been shown to have a higher incidence of insulin resistance. In some embodiments, methods of the present disclosure used to diagnose, assess, monitor, or stratify risk for GDM may be used to diagnose, assess, monitor and/or stratify risk for developing pre-eclampsia.

Gestational Windows

In the context of embodiments of the present invention, the length of time comprising pregnancy may be divided into two or more gestational windows. As used herein, the term "gestational window" refers to any temporally, developmentally and/or physiologically defined period of a pregnancy. Gestational windows may comprise weeks of pregnancy. The typical term of a human pregnancy is from about 40 to about 42 weeks (but may extend beyond 42 weeks in some cases) and is calculated starting with the end of the last menstrual cycle of a pregnant subject. As such, gestational windows may comprise from about 0 to about 46, from about 0 to about 42, from about 2 to about 42, from about 4 to about 42, from about 8 to about 42, from about 12 to about 42, from about 16 to about 42, from about 20 to about 42, from about 24 to about 42, from about 28 to about 42, from about 32 to about 42, from about 36 to about 42, from about 12 to about 36, from about 16 to about 36, from about 20 to about 36, from about 24 to about 36, from about 10 to about 28, from about 16 to about 28, from about 20 to about 28, from about 16 to about 24, or from about 18 to about 24 weeks of pregnancy. In some cases, gestational windows may comprise week 1, week 2, week 3, week 4, week 5, week 6, week 7, week 8, week 9, week 10, week 11, week 12, week 13, week 14, week 15, week 16, week 17, week 18, week 19, week 20, week 21, week 22, week 23, week 24, week 25, week 26, week 27, week 28, week 29, week 30, week 31, week 32, week 33, week 34, week 35, week 36, week 37, week 38, week 39, week 40, week 41, week 42, week 43, week 44, week 45, week 46 or after week 46 of pregnancy. Gestational windows may also comprise months of pregnancy. The typical term of a pregnancy is 9-10 months. As such, gestational windows may comprise from about month 1 to about month 10, from about month 2 to about month 10, from about month 3 to about month 10, from about month 4 to about month 10, from about month 5 to about month 10, from about month 6 to about month 10, from about month 7 to about month 10, from about month 8 to about month 10, from about month 9 to about month 10, from about month 1 to about month 9, from about month 2 to about month 9, from about month 3 to about month 9, from about month 4 to about month 9, from about month 5 to about month 9, from about month 6 to about month 9, from about month 7 to about month 9, from about month 8 to about mount 9, from about month 1 to about month 6, from about month 1 to about month 4, from about month 1 to about month 3, from about month 3 to about month 9, from about month 3 to about month 6, from about month 4 to about month 6, from about month 3 to about month 7, from about month 2 to about month 7 or from about month 2 to about month 6 of pregnancy. In some cases, gestational windows may comprise month 1, 2, 3, 4, 5, 6, 7, 8, 9 or 10. In other embodiments, gestational windows may comprise trimesters. The term of a pregnancy may be divided into three trimesters. The first trimester may comprise from about 1 month to about 3 months of pregnancy and/or from about week 1 to about week 12 of pregnancy. During the first trimester, typical development comprises fetal growth to a weight of about 28 g (or about 1 ounce) and a length from about 7.6 cm to about 10 cm (or from about 3 to about 4 inches) long. The second trimester may comprise from about 4 months to about 6 months of pregnancy and/or from about 13 weeks to about 28 weeks of pregnancy. During the second trimester, typical development comprises fetal growth to a weight of about 910 g (or about 2 pounds) and length from about 23 cm to about 31 cm (or from about 9 inches to about 12 inches) long. The third trimester may comprise from about 7 months to about 9 months of pregnancy and/or from about 29 to about 40 weeks of pregnancy. During the third trimester, typical development comprises fetal growth to a weight of about 3.2 kg (or about 7 pounds) and length from about 45 cm to about 51 cm (or from about 18 to about 20 inches) long.

In some embodiments, gestational windows may comprise stages of fetal development. Such stages may include, but are not limited to blastocyst formation, placental formation, embryo formation, heart development, lung development, liver development, kidney development, gastrointestinal development and nervous system development.

Monitoring and Therapy

Analyses disclosed herein may comprise the use of a single sample obtained from a subject. Such samples may comprise bodily fluid samples. Bodily fluid samples may include, but are not limited to blood, urine, mucous, amniotic fluid, saliva and/or other sample types disclosed herein. Biomarker levels may be analyzed in a single subject sample or in multiple subject samples. GCD59 levels, for example, may be monitored over time. As used herein, the term "monitoring" refers to the act of observing, evaluating and/or measuring over time. Observing, evaluating and/or measuring may be recorded in the form of one or more amounts or values.

In some embodiments, values for the purposes of monitoring may comprise concentration values or concentration equivalent values. Monitoring is typically carried out by obtaining initial or baseline values by which subsequent values may be compared. During monitoring, one or more subsequent values may be obtained and compared to baseline values and/or any other previously obtained values. Subsequent values may be obtained for the purposes of short-term comparisons, long-term comparisons, weekly comparisons, monthly comparisons and the like. Short-term comparisons may be used to monitor one or more biomarker levels in subject samples in response to a particular challenge (e.g., a glucose challenge) to the subject. Such subject samples may be obtained every 10, 20, 30, 40, 50, 75 and/or 150 minutes and analyzed to generate subsequent values for comparison. Subject samples for short-term comparisons may be obtained every 1, 2, 3, 4, 5, 10, 12 and/or 24 hours for the generation of subsequent values. Such subject samples may comprise blood, urine, mucous, amniotic fluid, saliva and/or any other bodily fluids disclosed herein. Glucose levels and/or levels of glycated proteins may also be obtained from such samples. In some cases, levels of GCD59 (including, but not limited to concentration values) may be obtained from subject samples for short-term comparisons.

In some embodiments, long-term comparisons may be used to monitor one or more biomarker levels/concentrations in subjects. Subsequent values obtained for long-term comparisons may be obtained each week, each month, each quarter, each year and/or at least each year. Long-term comparisons may comprise subsequent values obtained from subject samples obtained about 2 weeks to about 2 months apart. Such subject samples may comprise bodily fluids samples. Such bodily fluid samples may comprise blood, urine, mucous, amniotic fluid, saliva and/or any other bodily fluid samples disclosed herein. In some embodiments, glucose levels may be obtained from samples for long-term comparisons. In other embodiments, levels of glycated proteins may be obtained from samples for long-term comparisons. In further embodiments, GCD59 levels (e.g. GCD59 concentration levels) may be obtained.

In embodiments related to monitoring of GDM, observance, evaluation and/or measurement values may include, but are not limited to values reflecting weight, blood glucose levels, levels of glycated proteins (e.g., GCD59), biomarker levels, fetal weight, fetal size and BMI. Monitoring of GDM may be carried out through repeated tests and/or observations. Baseline values may be obtained prior to pregnancy, upon a first prenatal medical examination or within a given interval of pregnancy. Baseline values may, for example, be obtained from about 12 weeks to about 36 weeks of pregnancy, from about 20 weeks to about 36 weeks of pregnancy and/or from about 24 to about 28 weeks of pregnancy (including during week 24 of pregnancy, during week 25 of pregnancy, during week 26 of pregnancy, during week 27 of pregnancy and/or during week 28 of pregnancy. Some baseline values may be concentration values. Such concentration values may be obtained from a variety of sources. Baseline concentration values may also be obtained from bodily fluids including, but not limited to blood, urine, mucous, amniotic fluid, saliva and/or any other bodily fluid disclosed herein. Subject sample levels may be compared to baseline levels and/or previously obtained levels to determine changes in the level of one or more factor being analyzed. In some case, subject sample levels are compared to a threshold value for one or more factors being analyzed.

In some embodiments, baseline values may comprise the results of one or more tests used to evaluate one or more factors related to GDM. Such tests may include, but are not limited to glucose challenge testing (GCT) the OGTT, the fasting glucose test, the opportunistic glucose test, the 2-hour postprandial glucose test, the HbA1c test, the fructosamine test and the 1,5-anhydroglucitol test.

During GDM monitoring, one or more subsequent values may be obtained and compared to baseline values and/or any other previously obtained values. Some subsequent values may be obtained for the purposes of short-term comparisons, long-term comparisons, weekly comparisons, monthly comparisons, trimester comparisons, transpartum comparisons (e.g., comparisons between pre- and post-delivery), transgestational comparisons (e.g., comparisons between pre-, peri- and/or post-pregnancy) and interpregnancy comparisons (e.g., between a first pregnancy and a second, third and/or fourth pregnancy). Short-term comparisons may be used to monitor one or more biomarker levels in response to a particular challenge (e.g., a glucose challenge) to the subject. Bodily fluid samples obtained for short-term comparisons may be obtained every 10, 20, 30, 40, 50, 75 and/or 150 minutes and analyzed to generate subsequent values for comparison. In other embodiments, bodily fluids for short-term comparisons may be obtained every 1, 2, 3, 4, 5, 10, 12 and/or 24 hours for the generation of subsequent values. Some bodily fluid samples for short-term comparisons may comprise blood, urine, mucous, amniotic fluid, saliva and/or any other bodily fluid disclosed herein. In some cases, glucose levels may be obtained from such samples. Levels of glycated proteins (including, but not limited to concentration values) may also be obtained from bodily fluids for short-term comparisons. Such levels may comprise GCD59 levels.

In some embodiments, long-term comparisons may be used to monitor one or more biomarker levels/concentrations in pregnant subjects. Subsequent values obtained for long-term comparisons may be obtained each week, each month, each trimester, each pregnancy and/or in each of pre-gestational, peri-gestational and post-gestational periods. Some long-term comparisons may comprise subsequent values obtained from subject samples obtained about 2 weeks to about 2 months apart. Some such subject samples may comprise bodily fluids samples. Such bodily fluid samples may comprise blood, urine, mucous, amniotic fluid, saliva and/or any other bodily fluids disclosed herein. In some cases, glucose levels may be obtained from samples for long-term comparisons. In other embodiments, levels of glycated proteins may be obtained from samples for long-term comparisons. In further embodiments, GCD59 levels (e.g., GCD59 concentration levels) may be obtained.

Monitoring may be carried out to observe the onset of one or more conditions and/or diseases. Some monitoring may be carried out to determine the onset of GDM and/or pre-eclampsia. In such embodiments, baseline values obtained may not indicate GDM and/or pre-eclampsia; however, subsequent values obtained may indicate onset. Onset may be determined by monitoring subject samples, including, but not limited to bodily fluids. Such bodily fluids may include blood, urine, mucous, amniotic fluid, saliva and/or any other bodily fluids disclosed herein. In some subject samples, glucose levels may be monitored to determine onset of GDM and/or pre-eclampsia. In other embodiments, levels of glycated proteins may be monitored to determine onset of GDM and/or pre-eclampsia. In further embodiments, GCD59 levels (e.g., GCD59 concentration levels) may be monitored to determine onset of GDM and/or pre-eclampsia.

In some embodiments, monitoring may be carried out to observe or assess the progression or regression of one or more conditions and/or diseases. Some monitoring may be carried out to observe or assess the progression or regression of GDM and/or pre-eclampsia. In such embodiments, baseline values obtained may indicate GDM and/or pre-eclampsia: however, subsequent values obtained may indicate progression or regression of disease. Progression or regression may be assessed by monitoring subject samples, including, but not limited to bodily fluids. Such bodily fluids may include blood, urine, mucous, amniotic fluid, saliva and/or any other bodily fluids disclosed herein. In some embodiments, glucose levels may be monitored to assess progression or regression of GDM and/or pre-eclampsia. In other embodiments, levels of glycated proteins may be monitored to assess progression or regression of GDM and/or pre-eclampsia. In further embodiments, GCD59 levels (e.g., GCD59 concentration levels) may be monitored to assess progression or regression of GDM and/or pre-eclampsia.

In some embodiments, monitoring may be carried out to observe or assess the progression of a diabetic condition in a postpartum subject. As used herein, the term "postpartum subject" refers to a subject that has recently given birth. Postpartum subjects may include subjects that have given birth in about the last hour, about the last day, about the last month, about the last 3 months and/or about the last year. In some embodiments, methods of the present disclosure may be used to determine GCD59 levels in one or more samples obtained from postpartum subjects. Such GCD59 levels obtained from one or more samples obtained from postpartum subjects may be used to diagnose, prognose or otherwise analyze one or more diabetic condition in such postpartum subjects.

In some embodiments, evaluation of subject samples may be carried out in order to apply an appropriate form of therapy. Such subject samples may be obtained from pregnant subjects with GDM. Therapeutic strategies for GDM may comprise diet modulation, increased activity, increased exercise, periodic blood glucose monitoring and/or insulin therapy. Selecting one or more therapeutic strategies based on evaluation of samples from a pregnant subject and applying one or more of the selected therapeutic strategies to the pregnant subject may prevent GDM-related conditions that effect infant subjects born to such pregnant subjects. Samples obtained from such pregnant subjects may be evaluated for levels of one or more biomarkers in order to select one or more therapeutic strategies. Such biomarkers may include glycated proteins, including, but not limited to GCD59. GCD59 concentration values obtained from pregnant subject samples may be used to select one or more therapies for the treatment of GDM. In such embodiments, one or more GDM-related conditions in infant subjects born to such pregnant subjects may be reduced, reversed and/or prevented.

In some embodiments, methods of the present disclosure may be used to monitor subjects undergoing treatment for GDM. Such methods may comprise adjusting treatment dosages and/or types of therapy based on insights obtained from any of the types of monitoring described herein.

Companion Diagnostics

In some embodiments, methods of the present disclosure may be used as companion diagnostics. As used herein, the term "companion diagnostic" refers to an assay, the results of which aid in the diagnosis or treatment of subjects. Companion diagnostics may be useful for stratifying patient disease, disorder or condition severity levels, allowing for modulation of treatment regimen and dose to reduce costs, shorten the duration of clinical trial, increase safety and/or increase effectiveness. Companion diagnostics may be used to predict the development of a disease, disorder or condition and aid in the prescription of preventative therapies. Some companion diagnostics may be used to select subjects for one or more clinical trials. In some cases, companion diagnostic assays may go hand-in-hand with a specific treatment to facilitate treatment optimization.

In some embodiments, methods of the present disclosure may be useful as companion diagnostics for diseases, disorders and/or conditions related to glycemic levels. Some companion diagnostics of the present invention may be useful for predicting and/or determining the severity of diabetes, pre-diabetes or other diabetic conditions including, but not limited to GDM. Some companion diagnostics of the present invention may be used to stratify subjects by risk of developing diabetic complications. Such diabetic complications may include, but are not limited to diabetic ketoacidosis, hyperglycemia, hypoglycemia, hyperglycemia hyperosmolar state, diabetic coma, infections of the respiratory tract, gum disease, heart damage, kidney damage, decreased sensation, vision loss, cardiovascular disease, muscle deterioration and stroke. Some companion diagnostics of the present invention may be used to facilitate and expedite drug development for anti-diabetic and metabolic disease drugs.

Point of Care Testing

In some embodiments, methods of the present disclosure, described herein may be used for point-of-care testing. As used herein, the term "point-of-care testing" refers to medical testing that is carried out at or near a site where a subject is receiving medical care. Point-of-care testing may facilitate shorter intervals between testing, review of test results and treatment. Point-of-care testing may also allow for patients to be tested and receive treatments determined by the results of such testing during the same day and/or during the same medical visit.

Platform Technologies

In some embodiments, methods of the present disclosure may be carried out using one or more platform technologies. As used herein, a "platform technology" refers to an instrument or system configured to standardize one or more steps of a method or assay. Platform technologies may be used, for example, to carry out immunological assays (e.g., ELISAs, immunoprecipitation assays, immunofluorescence assays, EIAs, RIAs, and Western blot analysis). Platform technologies may include one or more commercially available instruments or systems used to carry out immunological assays, for example, one or more Bio-Rad (Hercules, Calif.) instruments (including, but not limited to an IMARK™ Microplate Absorbance Reader, an XMARK™ Microplate Absorbance Spectrophotometer, a PW 41 Microplate Washer, and/or an IMMUNOWASH™ 1575 Microplate Washer); one or more BioTek (Winooski, Vt.) instruments (including, but not limited to an ELX800™ Absorbance Reader, a SYNERGY™ HT Multi-mode Microplate Reader, an ELX50™ Microplate Strip Washer, a PRECISION™ XS Automated Pipetting System, a MULTIFLO™ Automated Dispenser, an EL406™ Washer Dispenser, a MULTIFLO™ FX Multi-mode Dispenser, a 405 TS™ Microplate Washer, a 405 LS™ Microplate Washer, an ELx405 Select Deep Well Washer, and/or an ELx50 Washer); one or more Thermo-Fisher (Waltham, Mass.) instruments (including, but not limited to a MULTISKAN™ FC Microplate Photometer, a MULTISKAN® GO Microplate Spectrophotometer, a MULTIDROP™ Combi Reagent Dispenser, a MULTIDROP™ 384 Reagent Dispenser, a MULTIDROP™ DW Reagent Dispenser, and/or a WELLWASH™ Microplate Washer); one or more Molecular Devices (Sunnyvale, Calif.) instruments (including, but not limited to a GENEPIX® 4300A Microarray Scanner, a GENEPIX® 4400A Microarray Scanner, a GENEPIX® 4000B Microarray Scanner, a AQUAMAX® Microplate Washer, a MULTIWASH+™ Microplate Washer, and/or a GENEPIX® SL50 Automated Slide Loader); and/or one or more Tecan (Männedorf, Switzerland) instruments (including, but not limited to a SUNRISE™ absorbance microplate reader, an INFINITE® F50 absorbance microplate reader, a HYDROFLEX™ microplate washer, a HYDROSPEED™ microplate washer, and/or a CONNEC™ microplate stacker).

In some embodiments, platform technologies include automated platform technologies. Automated platform technologies are automated instruments or systems configured to carry out one or more steps of a method or assay in a standardized manner and independent of human manipulation, but may carry out such steps based on human input or guidance. Automated platform technologies may include one or more commercially available systems used to carry out immunological assays, for example, one or more Bio-Rad (Hercules, Calif.) systems (including, but not limited to a BIO-PLEX® 200 System and/or a BIO-PLEX® 3D Suspension Array System); one or more Tecan (Männedorf, Switzerland) systems (including, but not limited to a FREEDOM EVO® series system); a TRITURUS® system (Grifols, Los Angeles, CA); one or more Hamilton Laboratory Solutions (Manitowac, Wis.) systems (including, but not limited to a Microlab STAR™ Line System, a Microlab NIMBUS™ system, and/or a Microlab VANTAGE™ Liquid Handling System); one or more Abbott Laboratories (Abbott Park, IL) systems (including, but not limited to an ARCHITECT™ i2000SR immunoassay analyzer, an ARCHITECT™ i1000SR immunoassay analyzer, and/or an ARCHITECT™ i4000SR immunoassay analyzer); one or more Roche Diagnostics (Branford, CT) systems (including, but not limited to a COBAS® 8100 automated workflow series system, a COBAS® 8000 modular analyzer system, a COBAS® 6000 analyzer system, a COBAS® 4000 analyzer system, a COBAS® c 513 analyzer system, and/or a Urisys 2400@ analyser system); one or more Meso Scale Discovery (Rockville, MD) systems (including, but not limited to a MESO QuickPlex SQ 120 system and/or a MESO SECTOR S 600 system); one or more Siemens (Munich, Germany) systems (including, but not limited to, DIMENSION® EXL™ systems, DIMENSION VISTA® systems, DIMENSION® XPAND® Plus systems, DIMENSION® RXL MAX® systems, ADVIA Centaur XPT Immunoassay systems, ADVIA Centaur XP Immunoassay systems, ADVIA Centaur CP Immunoassay systems, IMMULITE 2000 XPi Immunoassay systems, IMMULITE 1000 Immunoassay systems, VersaCell systems, and/or VersaCell X3 systems); and/or one or more Luminex (Austin, Tex.) systems (including, but not limited to a MAGPIX® System and/or a LUMINEX® 100/200™ System).

In some embodiments, platform technologies used to carry out immunological assays may include one or modules capable of performing one or more desired steps. Such modules may be configured to carry out one or more of sample distribution, reagent addition and/or removal, incubation, mixing, signal detection, signal analysis, analyte quantification, rinsing, and sample and/or substrate disposal.

Formulations and Administration

Pharmaceutical Formulations

In some embodiments, the compounds or compositions of the present disclosure can be formulated using one or more excipients to: (1) increase stability; (2) increase cell permeability; (3) permit the sustained or delayed release (e.g., from a formulation); and/or (4) alter the biodistribution (e.g., target the composition to specific tissues or cell types). In addition to traditional excipients such as any and all solvents, dispersion media, diluents, or other liquid vehicles, dispersion or suspension aids, surface active agents, isotonic agents, thickening or emulsifying agents, preservatives, formulations of the present invention can include, without limitation, liposomes, lipid nanoparticles, polymers, lipoplexes, core-shell nanoparticles, peptides, proteins, cells transfected with the compounds or compositions of the invention (e.g., for transplantation into a subject) and combinations thereof.

Excipients

As used herein, the term "excipient" refers to any substance combined with a compound and/or composition of the invention before use. In some embodiments, excipients are inactive and used primarily as a carrier, diluent or vehicle for a compound and/or composition of the present invention. Various excipients for formulating pharmaceutical compositions and techniques for preparing the composition are known in the art (see Remington: The Science and Practice of Pharmacy, 21$^{st}$ Edition, A. R. Gennaro, Lippincott, Williams & Wilkins, Baltimore, Md., 2006; incorporated herein by reference).

The use of a conventional excipient medium is contemplated within the scope of the present disclosure, except insofar as any conventional excipient medium may be incompatible with a substance or its derivatives, such as by producing any undesirable biological effect or otherwise interacting in a deleterious manner with any other component(s) of the pharmaceutical composition.

Formulations of the pharmaceutical compositions described herein may be prepared by any method known or hereafter developed in the art of pharmacology. In general, such preparatory methods include the step of associating the active ingredient with an excipient and/or one or more other accessory ingredients.

A pharmaceutical composition in accordance with the present disclosure may be prepared, packaged, and/or sold in bulk, as a single unit dose, and/or as a plurality of single unit doses.

Relative amounts of the active ingredient, the pharmaceutically acceptable excipient, and/or any additional ingredients in a pharmaceutical composition in accordance with the present disclosure may vary, depending upon the identity, size, and/or condition of the subject being treated and further depending upon the route by which the composition is to be administered.

In some embodiments, a pharmaceutically acceptable excipient is at least 95%, at least 96%, at least 97%, at least 98%, at least 99%, or 100% pure. In some embodiments, an excipient is approved for use in humans and for veterinary use. In some embodiments, an excipient is approved by United States Food and Drug Administration. In some embodiments, an excipient is pharmaceutical grade. In some embodiments, an excipient meets the standards of the United States Pharmacopoeia (USP), the European Pharmacopoeia (EP), the British Pharmacopoeia, and/or the International Pharmacopoeia.

Pharmaceutically acceptable excipients used in the manufacture of pharmaceutical compositions include, but are not limited to, inert diluents, dispersing and/or granulating agents, surface active agents and/or emulsifiers, disintegrating agents, binding agents, preservatives, buffering agents, lubricating agents, and/or oils. Such excipients may optionally be included in pharmaceutical compositions.

Exemplary diluents include, but are not limited to, calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and/or combinations thereof.

Exemplary granulating and/or dispersing agents include, but are not limited to, potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (VEEGUM®), sodium lauryl sulfate, quaternary ammonium compounds, etc., and/or combinations thereof.

Exemplary surface active agents and/or emulsifiers include, but are not limited to, natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and VEEGUM® [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [TWEEN®20], polyoxyethylene sorbitan [TWEENn®60], polyoxyethylene sorbitan monooleate [TWEEN®80], sorbitan monopalmitate [SPAN®40], sorbitan monostearate [Span®60], sorbitan tristearate [Span®65], glyceryl monooleate, sorbitan monooleate [SPAN®80]), polyoxyethylene esters (e.g. polyoxyethylene monostearate [MYRJ®45], polyoxyethylene hydrogenated castor oil, polyethoxylated castor oil, polyoxymethylene stearate, and SOLUTOL®), sucrose fatty acid esters, polyethylene glycol fatty acid esters (e.g. CREMOPHOR®), polyoxyethylene ethers. (e.g. polyoxyethylene lauryl ether [BRIJ®30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, PLUORINC® F 68, POLOXAMER®188, cetrimonium bromide, cetylpyridinium chloride, benzalkonium chloride, docusate sodium, etc. and/or combinations thereof.

Exemplary binding agents include, but are not limited to, starch (e.g. cornstarch and starch paste); gelatin; sugars (e.g. sucrose, glucose, dextrose, dextrin, molasses, lactose, lactitol, mannitol); natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum®), and larch arabogalactan); alginates; polyethylene oxide; polyethylene glycol; inorganic calcium salts; silicic acid; polymethacrylates; waxes; water; alcohol; etc.; and combinations thereof.

Exemplary preservatives may include, but are not limited to, antioxidants, chelating agents, antimicrobial preservatives, antifungal preservatives, alcohol preservatives, acidic preservatives, and/or other preservatives. Exemplary antioxidants include, but are not limited to, alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and/or sodium sulfite. Exemplary chelating agents include ethylenediaminetetraacetic acid (EDTA), citric acid monohydrate, disodium edetate, dipotassium edetate, edetic acid, fumaric acid, malic acid, phosphoric acid, sodium edetate, tartaric acid, and/or trisodium edetate. Exemplary antimicrobial preservatives include, but are not limited to, benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and/or thimerosal. Exemplary antifungal preservatives include, but are not limited to, butyl paraben, methyl paraben, ethyl paraben, propyl paraben, benzoic acid, hydroxybenzoic acid, potassium benzoate, potassium sorbate, sodium benzoate, sodium propionate, and/or sorbic acid. Exemplary alcohol preservatives include, but are not limited to, ethanol, polyethylene glycol, phenol, phenolic compounds, bisphenol, chlorobutanol, hydroxybenzoate, and/or phenylethyl alcohol. Exemplary acidic preservatives include, but are not limited to, vitamin A, vitamin C, vitamin E, beta-carotene, citric acid, acetic acid, dehydroacetic acid, ascorbic acid, sorbic acid, and/or phytic acid. Other preservatives include, but are not limited to, tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, GLYDANT PLUS®, PHENONIP®, methylparaben, GERMALL®115, GERMABEN® II, NEOLONE™, KATHON™, and/or EUXYL®.

Exemplary buffering agents include, but are not limited to, citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, etc., and/or combinations thereof.

Exemplary lubricating agents include, but are not limited to, magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, etc., and combinations thereof.

Exemplary oils include, but are not limited to, almond, apricot kernel, avocado, babassu, bergamot, black current seed, borage, cade, camomile, canola, caraway, camauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and/or combinations thereof.

Excipients such as cocoa butter and suppository waxes, coloring agents, coating agents, sweetening, flavoring, and/or perfuming agents can be present in the composition, according to the judgment of the formulator.

Vehicles

Liposomes, Lipoplexes and Lipid Nanoparticles

Compounds or compositions of the present disclosure may be formulated using one or more liposomes, lipoplexes, or lipid nanoparticles. In one embodiment, pharmaceutical compounds or compositions of the present disclosure further comprise liposomes. Liposomes are artificially-prepared vesicles which may primarily comprise one or more lipid bilayers and may be used as a delivery vehicle for the administration of nutrients and pharmaceutical formulations. Liposomes can be of different sizes such as, but not limited to, a multilamellar vesicle (MLV) which may be hundreds of nanometers in diameter and may contain a series of concentric bilayers separated by narrow aqueous compartments, a small unicellular vesicle (SUV) which may be smaller than 50 nm in diameter, and a large unilamellar vesicle (LUV) which may be between 50 and 500 nm in diameter. Liposome design may include, but is not limited to, opsonins or ligands in order to improve the attachment of liposomes to unhealthy tissue or to activate events such as, but not limited to, endocytosis. Liposomes may contain a low or a high pH in order to improve the delivery of the pharmaceutical formulations.

The formation of liposomes may depend on the physicochemical characteristics such as, but not limited to, the pharmaceutical formulation entrapped and the liposomal ingredients, the nature of the medium in which the lipid vesicles are dispersed, the effective concentration of the entrapped substance and its potential toxicity, any additional processes involved during the application and/or delivery of the vesicles, the optimization size, polydispersity and the shelf-life of the vesicles for the intended application, and the batch-to-batch reproducibility and possibility of large-scale production of safe and efficient liposomal products.

In one embodiment such formulations may also be constructed or compositions altered such that they passively or actively are directed to different cell types in vivo.

Formulations can also be selectively targeted through expression of different ligands on their surface as exemplified by, but not limited by, folate, transferrin, N-acetylgalactosamine (GalNAc), and antibody targeted approaches.

Liposomes, lipoplexes, or lipid nanoparticles may be used to improve the functional efficacy of the compounds or compositions of the present disclosure as these formulations may be able to increase cell transfection with compositions of the invention. The liposomes, lipoplexes, or lipid nanoparticles may also be used to increase the stability of the compounds or compositions of the invention.

Liposomes that are specifically formulated for antibody cargo are prepared according to techniques known in the art, such as described by Eppstein et al. (Eppstein, D. A. et al., *Biological activity of liposome-encapsulated murine interferon gamma is mediated by a cell membrane receptor*. Proc Natl Acad Sci USA. 1985 June; 82(11):3688-92); Hwang et al. (Hwang, K. J. et al., *Hepatic uptake and degradation of unilamellar sphingomyelin/cholesterol liposomes; a kinetic study*. Proc Natl Acad Sci USA. 1980 July; 77(7):4030-4); U.S. Pat. Nos. 4,485,045 and 4,544,545. Production of liposomes with sustained circulation time is also described in U.S. Pat. No. 5,013,556.

Liposomes comprising compounds or compositions of the present invention may be generated using reverse phase evaporation utilizing lipids such as phosphatidylcholine, cholesterol as well as phosphatidylethanolamine that has been polyethylene glycol-derivatized. Filters with defined pore size are used to extrude liposomes of the desired diameter. In another embodiment, compositions of the present invention can be conjugated to the external surface of liposomes by disulfide interchange reaction as is described by Martin et al. (Martin, F. J. et al., *Irreversible coupling of immunoglobulin fragments to preformed vesicles. An improved method for liposome targeting*. J Biol Chem. 1982 Jan. 10; 257(1):286-8).

Polymers and Nanoparticles

Compounds or compositions of the invention can be formulated using natural and/or synthetic polymers. Non-limiting examples of polymers which may be used for delivery include, but are not limited to DMRI/DOPE, poloxamer, chitosan, cyclodextrin, and poly (lactic-co-glycolic acid) (PLGA) polymers. These may be biodegradable.

The polymer formulation can permit the sustained or delayed release of the compositions (e.g., following intramuscular or subcutaneous injection). The altered release profile for the compounds or compositions of the present disclosure can result in, for example, release of the compounds or compositions over an extended period of time. The polymer formulation may also be used to increase the stability of compounds or compositions of the invention.

Polymer formulations can also be selectively targeted through expression of different ligands as exemplified by, but not limited by, folate, transferrin, and N-acetylgalactosamine (GalNAc) (Benoit et al., Biomacromolecules. 2011 12:2708-2714: Rozema et al., Proc Natl Acad Sci USA. 2007 104:12982-12887; Davis. Mol Pharm. 2009 6:659-668; Davis, Nature 2010 464:1067-1070; herein incorporated by reference in its entirety).

Compounds or compositions of the present disclosure can also be formulated as nanoparticles using a combination of polymers, lipids, and/or other biodegradable agents, such as, but not limited to, calcium phosphate. Components may be combined in a core-shell, hybrid, and/or layer-by-layer architecture, to allow for fine-tuning of the nanoparticle so that the delivery the compounds or compositions of the invention may be enhanced. For compounds or compositions of the present disclosure, systems based on poly(2-(methacryloyloxy) ethyl phosphorylcholine)-block-(2-(di-isopropylamino)ethyl methacrylate), (PMPC-PDPA), a pH sensitive diblock copolymer that self-assembles to form nanometer-sized vesicles, also known as polymersomes, at physiological pH may be used. These polymersomes have been shown to successfully deliver relatively high payloads within live cells. (Massignani, et al, Cellular delivery of antibodies: effective targeted subcellular imaging and new therapeutic tool. Nature Proceedings, May, 2010).

In one embodiment, a PEG-charge-conversional polymer (Pitella et al., Biomaterials. 2011 32:3106-3114) may be used to form a nanoparticle to deliver the compounds or compositions of the present invention. The PEG-charge-conversional polymer may improve upon the PEG-polyanion block copolymers by being cleaved into a polycation at acidic pH, thus enhancing endosomal escape.

The use of core-shell nanoparticles has additionally focused on a high-throughput approach to synthesize cationic cross-linked nanogel cores and various shells (Siegwart et al., Proc Natl Acad Sci USA. 2011 108:12996-13001). The complexation, delivery, and internalization of the polymeric nanoparticles can be precisely controlled by altering the chemical composition in both the core and shell components of the nanoparticle.

In one embodiment, matrices of poly (ethylene-co-vinyl acetate), are used to deliver the compounds or compositions of the invention. Such matrices are described in Nature Biotechnology 10, 1446-1449 (1992).

Routes of Administration

The compounds or compositions of the present invention may be administered by any of the standard methods or routes known in the art.

Compounds or compositions of the present invention may be administered by any route which results in a therapeutically effective outcome. These include, but are not limited to enteral, gastroenteral, epidural, oral, transdermal, epidural (peridural), intracerebral (into the cerebrum), intracerebroventricular (into the cerebral ventricles), epicutaneous (application onto the skin), intradermal, (into the skin itself), subcutaneous (under the skin), nasal administration (through the nose), intravenous (into a vein), intraarterial (into an artery), intramuscular (into a muscle), intracardiac (into the heart), intraosseous infusion (into the bone marrow), intrathecal (into the spinal canal), intraperitoneal. (infusion or injection into the peritoneum), intravesical infusion, intravitreal, (through the eye), intracavernous injection, (into the base of the penis), intravaginal administration, intrauterine, extra-amniotic administration, transdermal (diffusion through the intact skin for systemic distribution), transmucosal (diffusion through a mucous membrane), insufflation (snorting), sublingual, sublabial, enema, eye drops (onto the conjunctiva), or in ear drops. In specific embodiments, compounds or compositions may be administered in a way which allows them cross the blood-brain barrier, vascular barrier, or other epithelial barrier. Non-limiting routes of administration compounds or compositions of the present invention are described below.

Parenteral and Injectable Administration

Liquid dosage forms for oral and parenteral administration include, but are not limited to, pharmaceutically acceptable emulsions, microemulsions, solutions, suspensions, syrups, and/or elixirs. In addition to active ingredients, liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, oral compositions can include adjuvants such as wetting agents, emulsifying and suspending agents, sweetening, flavoring, and/or perfuming agents. In certain embodiments for parenteral administration, compositions are mixed with solubilizing agents such as CREMOPHOR®, alcohols, oils, modified oils, glycols, polysorbates, cyclodextrins, polymers, and/or combinations thereof. In other embodiments, surfactants are included such as hydroxypropylcellulose.

Injectable preparations, for example, sterile injectable aqueous or oleaginous suspensions may be formulated according to the known art using suitable dispersing agents, wetting agents, and/or suspending agents. Sterile injectable preparations may be sterile injectable solutions, suspensions, and/or emulsions in nontoxic parenterally acceptable diluents and/or solvents, for example, as a solution in 1,3-butanediol. Among the acceptable vehicles and solvents that may be employed are water, Ringer's solution, U.S.P., and isotonic sodium chloride solution. Sterile, fixed oils are conventionally employed as a solvent or suspending medium. For this purpose, any bland fixed oil can be employed including synthetic mono- or diglycerides. Fatty acids such as oleic acid can be used in the preparation of injectables.

Injectable formulations can be sterilized, for example, by filtration through a bacterial-retaining filter, and/or by incorporating sterilizing agents in the form of sterile solid compositions which can be dissolved or dispersed in sterile water or other sterile injectable medium prior to use.

In order to prolong the effect of an active ingredient, it is often desirable to slow the absorption of the active ingredient from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are prepared by entrapping the drug in liposomes or microemulsions which are compatible with body tissues.

Rectal and Vaginal Administration

Compositions for rectal or vaginal administration are typically suppositories which can be prepared by mixing compositions with suitable non-irritating excipients such as cocoa butter, polyethylene glycol or a suppository wax which are solid at ambient temperature but liquid at body temperature and therefore melt in the rectum or vaginal cavity and release the active ingredient.

Oral Administration

Solid dosage forms for oral administration include capsules, tablets, pills, powders, and granules. In such solid dosage forms, an active ingredient is mixed with at least one inert, pharmaceutically acceptable excipient such as sodium citrate or dicalcium phosphate and/or fillers or extenders (e.g. starches, lactose, sucrose, glucose, mannitol, and silicic acid), binders (e.g. carboxymethylcellulose, alginates, gelatin, polyvinylpyrrolidinone, sucrose, and acacia), humectants (e.g. glycerol), disintegrating agents (e.g. agar, calcium carbonate, potato or tapioca starch, alginic acid, certain silicates, and sodium carbonate), solution retarding agents (e.g. paraffin), absorption accelerators (e.g. quaternary ammonium compounds), wetting agents (e.g. cetyl alcohol and glycerol monostearate), absorbents (e.g. kaolin and bentonite clay), and lubricants (e.g. talc, calcium stearate, magnesium stearate, solid polyethylene glycols, sodium lauryl sulfate), and mixtures thereof. In the case of capsules, tablets and pills, the dosage form may comprise buffering agents.

Topical or Transdermal Administration

As described herein, compounds or compositions of the present disclosure may be formulated for administration topically. The skin may be an ideal target site for delivery as it is readily accessible. Gene expression may be restricted not only to the skin, potentially avoiding nonspecific toxicity, but also to specific layers and cell types within the skin.

The site of cutaneous expression of the delivered compounds or compositions will depend on the route of nucleic acid delivery. Three routes are commonly considered to deliver compounds or compositions of the present invention to the skin: (i) topical application (e.g. for local/regional treatment and/or cosmetic applications); (ii) intradermal injection (e.g. for local/regional treatment and/or cosmetic applications); and (iii) systemic delivery (e.g. for treatment of dermatologic diseases that affect both cutaneous and extra cutaneous regions). Compounds or compositions of the invention can be delivered to the skin by several different approaches known in the art.

In one embodiment, the invention provides for a variety of dressings (e.g., wound dressings) or bandages (e.g., adhesive bandages) for conveniently and/or effectively carrying out methods of the present invention. Typically dressing or bandages may comprise sufficient amounts of pharmaceutical compositions and/or compounds or compositions of the present disclosure described herein to allow a user to perform multiple treatments of a subject(s).

In one embodiment, the invention provides for compounds or compositions to be delivered in more than one injection.

Dosage forms for topical and/or transdermal administration of a composition may include ointments, pastes, creams, lotions, gels, powders, solutions, sprays, inhalants and/or patches. Generally, an active ingredient is admixed under sterile conditions with a pharmaceutically acceptable excipient and/or any needed preservatives and/or buffers as may be required.

Additionally, the present invention contemplates the use of transdermal patches, which often have the added advantage of providing controlled delivery of a compound to the body. Such dosage forms may be prepared, for example, by dissolving and/or dispensing the compound in the proper medium. Alternatively, or additionally, rate may be controlled by either providing a rate controlling membrane and/or by dispersing the compound in a polymer matrix and/or gel.

Formulations suitable for topical administration include, but are not limited to, liquid and/or semi liquid preparations such as liniments, lotions, oil in water and/or water in oil emulsions such as creams, ointments and/or pastes, and/or solutions and/or suspensions.

Topically-administrable formulations may, for example, comprise from about 1% to about 10% (w/w) active ingredient, although the concentration of active ingredient may be as high as the solubility limit of the active ingredient in the solvent. Formulations for topical administration may further comprise one or more of the additional ingredients described herein.

Depot Administration

As described herein, in some embodiments, compounds or compositions of the present invention are formulated in depots for extended release. Generally, a specific organ or tissue (a "target tissue") is targeted for administration.

In some embodiments, compounds or compositions of the present invention are spatially retained within or proximal to a target tissue. Provided are methods of providing compounds or compositions to one or more target tissue of a mammalian subject by contacting the one or more target tissue (comprising one or more target cells) with compounds or compositions under conditions such that the compounds or compositions, are substantially retained in the target tissue, meaning that at least 10, 20, 30, 40, 50, 60, 70, 80, 85, 90, 95, 96, 97, 98, 99, 99.9, 99.99 or greater than 99.99% of the composition is retained in the target tissue. Advantageously, retention is determined by measuring the level of the compositions entering the target tissues and/or cells. For example, at least 1, 5, 10, 20, 30, 40, 50, 60, 70, 80, 85, 90, 95, 96, 97, 98, 99, 99.9, 99.99 or greater than 99.99% of the compounds or compositions of the invention administered to the subject are present intracellularly at a period of time following administration. For example, intramuscular injection to a mammalian subject is performed using an aqueous composition of the present invention and a transfection reagent, and retention of the composition is determined by measuring the level of the compounds or compositions of the invention present in the muscle cells.

Certain aspects of the invention are directed to methods of providing compounds or compositions to target tissues of mammalian subjects, by contacting the target tissues (containing one or more target cells) with compounds or compositions under conditions such that the compounds or compositions are substantially retained in the target tissue. In some embodiments, effective amounts of the compounds or compositions of the present disclosure may be used such that the effect of interest is produced in at least one target cell. Compounds or compositions generally contain cell penetration agents and a pharmaceutically acceptable carrier, although compounds or compositions in "naked" form (such as compounds or compositions without cell penetration agents or other agents) are also contemplated.

In some embodiments, compounds or compositions include a plurality of compounds or compositions. Optionally, compositions also contain cell penetration agents to assist in the intracellular delivery of compositions. A determination is made of the composition dose required to target a target of interest in a substantial percentage of cells contained within a predetermined volume of the target tissue (generally, without targeting compounds in tissue adjacent to the predetermined volume, or distally to target tissues). Subsequent to this determination, the determined dose may be introduced directly into the tissue of the mammalian subject.

In one embodiment, the invention provides for the compounds or compositions to be delivered in more than one injection or by split dose injections.

Pulmonary Administration

Pharmaceutical compositions may be prepared, packaged, and/or sold in formulations suitable for pulmonary administration via the buccal cavity. Such formulations may comprise dry particles further comprising active ingredients and having a diameter in the range from about 0.5 nm to about 7 nm or from about 1 nm to about 6 nm. Such compositions are suitably in the form of dry powders for administration using a device comprising a dry powder reservoir to which a stream of propellant may be directed to disperse the powder and/or using a self-propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nm and at least 95% of the particles by number have a diameter less than 7 nm. Alternatively, at least 95% of the particles by weight have a diameter greater than 1 nm and at least 90% of the particles by number have a diameter less than 6 nm. Dry powder compositions may include a solid fine powder diluent such as sugar and are conveniently provided in a unit dose form.

Low boiling propellants generally include liquid propellants having a boiling point of below 65° F. at atmospheric pressure. Generally, the propellant may constitute 50% to 99.9% (w/w) of the composition, and active ingredient may constitute 0.1% to 20% (w/w) of the composition. A propellant may further comprise additional ingredients such as a liquid non-ionic and/or solid anionic surfactant and/or a solid diluent (which may have a particle size of the same order as particles comprising the active ingredient).

Pharmaceutical compositions formulated for pulmonary delivery may provide an active ingredient in the form of droplets of a solution and/or suspension. Such formulations may be prepared, packaged, and/or sold as aqueous and/or dilute alcoholic solutions and/or suspensions, optionally sterile, comprising active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methy hydroxybenzoate. Droplets provided by this route of administration may have an average diameter in the range from about 0.1 nm to about 200 nm.

Intranasal, Nasal and Buccal Administration

Formulations described herein as being useful for pulmonary delivery are useful for intranasal delivery of a pharmaceutical composition. Another formulation suitable for intranasal administration is a coarse powder comprising the active ingredient and having an average particle from about 0.2 μm to 500 μm. Such a formulation is administered in the manner in which snuff is taken, i.e. by rapid inhalation through the nasal passage from a container of the powder held close to the nose.

Formulations suitable for nasal administration may, for example, comprise from about as little as 0.1% (w/w) and as much as 100% (w/w) of active ingredient, and may comprise one or more of the additional ingredients described herein. A pharmaceutical composition may be prepared, packaged, and/or sold in a formulation suitable for buccal administration. Such formulations may, for example, be in the form of tablets and/or lozenges made using conventional methods, and may have, for example, 0.1% to 20% (w/w) active ingredient, the balance comprising an orally dissolvable and/or degradable composition and, optionally, one or more of the additional ingredients described herein. Alternately, formulations suitable for buccal administration may comprise a powder and/or an aerosolized and/or atomized solution and/or suspension comprising active ingredient. Such powdered, aerosolized, and/or aerosolized formulations, when dispersed, may have an average particle and/or droplet size in the range from about 0.1 nm to about 200 nm, and may further comprise one or more of any additional ingredients described herein.

Ophthalmic or Otic Administration

A pharmaceutical composition may be prepared, packaged, and/or sold in a formulation suitable for ophthalmic or otic administration. Such formulations may, for example, be in the form of eye or ear drops including, for example, a 0.1 to 1.0% (w/w) solution and/or suspension of the active ingredient in an aqueous or oily liquid excipient. Such drops may further comprise buffering agents, salts, and/or one or more other of any additional ingredients described herein. Other ophthalmically-administrable formulations which are useful include those which comprise the active ingredient in microcrystalline form and/or in a liposomal preparation. Subretinal inserts may also be used as a form of administration.

Payload Administration

Compounds or compositions of the invention described herein may be used in a number of different scenarios in which delivery of a substance (the "payload") to a biological target is desired, for example delivery of detectable substances for detection of the target, or delivery of a therapeutic or diagnostic agent. Detection methods can include, but are not limited to, both imaging in vitro and in vivo imaging methods, e.g., immunohistochemistry, bioluminescence imaging (BLI), Magnetic Resonance Imaging (MRI), positron emission tomography (PET), electron microscopy, X-ray computed tomography, Raman imaging, optical coherence tomography, absorption imaging, thermal imaging, fluorescence reflectance imaging, fluorescence microscopy, fluorescence molecular tomographic imaging, nuclear magnetic resonance imaging, X-ray imaging, ultrasound imaging, photoacoustic imaging, lab assays, or in any situation where tagging/staining/imaging is required.

Compounds or compositions of the present disclosure can be designed to include both a linker and a payload in any useful orientation. For example, a linker having two ends is used to attach one end to the payload and the other end to the compounds or compositions of the present disclosure. In some embodiments, the compounds or compositions of the invention can include more than one payload as well as a cleavable linker. In another example, a drug that may be attached to the compounds or compositions of the present disclosure via a linker and may be fluorescently labeled can be used to track the drug in vivo, e.g. intracellularly.

Other examples include, but are not limited to, the use of the compounds or compositions of the present disclosure in reversible drug delivery into cells.

In some embodiments, compounds or compositions of the present disclosure described herein can be used in intracellular targeting of a payload, e.g., detectable or therapeutic agents, to specific organelles. In addition, compounds or compositions of the present disclosure may be used to deliver therapeutic agents to cells or tissues, e.g., in living animals. For example, compounds or compositions described herein may be used to deliver chemotherapeutic agents to kill cancer cells. Compounds or compositions described herein attached to therapeutic agents through linkers can facilitate membrane permeation allowing the therapeutic agent to travel into a cell to reach an intracellular target.

In some embodiments, the payload may be a therapeutic agent such as a cytotoxin, radioactive ion, chemotherapeutic, or other therapeutic agent. A cytotoxin or cytotoxic agent includes any agent that may be detrimental to cells. Examples include, but are not limited to, taxol, cytochalasin B, gramicidin D, ethidium bromide, emetine, mitomycin, etoposide, teniposide, vincristine, vinblastine, colchicine, doxorubicin, daunorubicin, dihydroxyanthracinedione, mitoxantrone, mithramycin, actinomycin D, 1-dehydrotestosterone, glucocorticoids, procaine, tetracaine, lidocaine, propranolol, puromycin, maytansinoids, e.g., maytansinol (see U.S. Pat. No. 5,208,020 incorporated herein in its entirety), rachelmycin (CC-1065, see U.S. Pat. Nos. 5,475,092, 5,585,499, and 5,846,545, all of which are incorporated herein by reference), and analogs or homologs thereof. Radioactive ions include, but are not limited to iodine (e.g., iodine 125 or iodine 131), strontium 89, phosphorous, palladium, cesium, iridium, phosphate, cobalt, yttrium 90, samarium 153, and praseodymium. Other therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thiotepa chlorambucil, rachelmycin (CC-1065), melphalan, carmustine (BSNU), lomustine (CCNU), cyclophosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine, vinblastine, taxol and maytansinoids).

In some embodiments, the payload may be a detectable agent, such as various organic small molecules, inorganic compounds, nanoparticles, enzymes or enzyme substrates, fluorescent materials, luminescent materials (e.g., luminol), bioluminescent materials (e.g., luciferase, luciferin, and aequorin), chemiluminescent materials, radioactive materials (e.g., $^{18}F$, $^{62}Ga$, $^{81m}Kr$, $^{82}Rb$, $^{111}In$, $^{123}I$, $^{133}Xe$, $^{201}Tl$, $^{125}I$, $^{35}S$, $^{14}C$, $^{3}H$, or $^{99m}Tc$ (e.g., as pertechnetate (technetate (VII), $TcO_4^-$)), and contrast agents (e.g., gold (e.g., gold nanoparticles), gadolinium (e.g., chelated Gd), iron oxides (e.g., superparamagnetic iron oxide (SPIO), monocrystalline iron oxide nanoparticles (MIONs), and ultrasmall superparamagnetic iron oxide (USPIO)), manganese chelates (e.g., Mn-DPDP), barium sulfate, iodinated contrast media (iohexol), microbubbles, or perfluorocarbons). Such optically-detectable labels include for example, without limitation, 4-acetamido-4'-isothiocyanatostilbene-2,2'disulfonic acid; acridine and derivatives (e.g., acridine and acridine isothiocyanate); 5-(2'-aminoethyl)aminonaphthalene-1-sulfonic acid (EDANS); 4-amino-N-[3-vinylsulfonyl)phenyl]naphthalimide-3,5 disulfonate; N-(4-anilino-1-naphthyl)maleimide; anthranilamide; BODIPY; Brilliant Yellow; coumarin and derivatives (e.g., coumarin, 7-amino-4-methylcoumarin (AMC, Coumarin 120), and 7-amino-4-trifluoromethylcoumarin (Coumarin 151)); cyanine dyes; cyanosine; 4',6-diaminidino-2-phenylindole (DAPI); 5',5''-dibromopyrogallol-sulfonaphthalein (Bromopyrogallol Red); 7-diethylamino-3-(4'-isothiocyanatophenvl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]-naphthalene-1-sulfonyl chloride (DNS, dansylchloride); 4-dimethylaminophenylazophenvl-4'-isothiocyanate (DABITC); eosin and derivatives (e.g., cosin and cosin isothiocyanate); erythrosin and derivatives (e.g., erythrosin B and erythrosin isothiocyanate); ethidium; fluorescein and derivatives (e.g., 5-carboxyfluorescein (FAM), 5-(4,6-dichlorotriazin-2-yl)aminofluorescein (DTAF), 2',7'-dimethoxy-4'5'-dichloro-6-carboxyfluorescein, fluorescein, fluorescein isothiocyanate, X-rhodamine-5-(and-6)-isothiocyanate (QFITC orXRITC), and fluorescamine); 2-[2-[3-[[1,3-dihydro-1,1-dimethyl-3-(3-sulfopropyl)-2H-benz[e]indol-2-ylidene]ethylidene]-2-[4-(ethoxycarbonyl)-1-piperazinyl]-1-cyclopenten-1-yl]ethenyl]-1,1-dimethyl-3-(3-sulforpropyl)-1H-benz[e]indolium hydroxide, inner salt, compound with n,n-diethylethanamine(1:1) (IR144); 5-chloro-2-[2-[3-[(5-chloro-3-ethyl-2(3H)-benzothiazol-ylidene)ethylidene]-2-(diphenylamino)-1-cyclopenten-1-yl]ethenyl]-3-ethyl benzothiazolium perchlorate (IR140); Malachite Green isothiocyanate; 4-methylumbelliferone orthocresolphthalein; nitrotyrosine; pararosaniline; Phenol Red; B-phycocrythrin; o-phthaldialdehyde; pyrene and derivatives (e.g., pyrene, pyrene butyrate, and succinimidyl 1-pyrene); butyrate quantum dots; Reactive Red 4 (CIBACRON™ Brilliant Red 3B-A); rhodamine and derivatives (e.g., 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red), N,N,N',N'-tetramethyl-6-carboxyrhodamine (TAMRA) tetramethyl iodamine, and tetramethyl rhodamine isothiocyanate (TRITC)); riboflavin; resolicit acid; terbium chelate derivatives; Cyanine-3 (Cy3): Cyanine-5 (Cy5); cyanine-5.5 (Cy5.5), Cyanine-7 (Cy7): IRD 700; IRD 800; Alexa 647; La Jolta Blue; phthalo cyanine; and naphthalo cyanine.

In some embodiments, the detectable agent may be a non-detectable precursor that becomes detectable upon activation (e.g., fluorogenic tetrazine-fluorophore constructs (e.g., tetrazine-BODIPY FL, tetrazine-Oregon Green 488, or tetrazine-BODIPY TMR-X) or enzyme activatable fluorogenic agents (e.g., PROSENSE® (VisEn Medical))). In vitro assays in which the enzyme labeled compositions can be used include, but are not limited to, enzyme linked immunosorbent assays (ELISAs), immunoprecipitation assays, immunofluorescence assays, enzyme immunoassays (ETA), radioimmunoassays (RIA), and Western blot analysis.

Dosage

The compounds or compositions of the present disclosure may be delivered for any of therapeutic, pharmaceutical, diagnostic or imaging by any appropriate route taking into consideration likely advances in the sciences of drug delivery. Delivery may be naked or formulated.

Naked Delivery

In some embodiments, compounds or compositions of the present disclosure may be delivered to cells, tissues, organs or organisms in naked form. As used herein in, the term "naked" refers to delivery that is free from agents or modifications which promote transfection or permeability. Compounds or compositions of the present disclosure may be delivered to cells, tissues, organs and/or organisms using routes of administration known in the art and described herein. Naked delivery may include formulation in a simple buffer such as saline or PBS.

Formulated Delivery

In some embodiments, compounds or compositions of the present disclosure may be formulated, using methods described herein. Formulations may comprise compounds or compositions of the present disclosure which may be modified and/or unmodified. Formulations may further include, but are not limited to, cell penetration agents, pharmaceutically acceptable carriers, delivery agents, bioerodible or biocompatible polymers, solvents, and sustained-release delivery depots. Compounds or compositions of the present disclosure may be delivered to cells using routes of administration known in the art and described herein.

Compounds or compositions may also be formulated for direct delivery to organs or tissues in any of several ways in the art including, but not limited to, direct soaking or bathing, via a catheter, by gels, powder, ointments, creams, gels, lotions, and/or drops, by using substrates such as fabric or biodegradable materials coated or impregnated with compounds or compositions, and the like.

Dosing

The present invention provides methods comprising administering one or more of the compounds or compositions of the invention in accordance with the invention to a subject in need thereof. Nucleic acids encoding antibodies, proteins or complexes comprising compounds or compositions of the present disclosure, or pharmaceutical, imaging, diagnostic, or prophylactic compounds or compositions thereof, may be administered to a subject using any amount and any route of administration effective for preventing, treating, diagnosing, or imaging a disease, disorder, and/or condition. The exact amount required will vary from subject to subject, depending on the species, age, and general condition of the subject, the severity of the disease, the particular composition, its mode of administration, its mode of activity, and the like. Compounds or compositions in accordance with the invention are typically formulated in dosage unit form for ease of administration and uniformity of dosage. It will be understood, however, that the total daily usage of the compounds or compositions of the present invention will be decided by the attending physician within the scope of sound medical judgment. The specific therapeutically effective, prophylactically effective, or appropriate imaging dose level for any particular subject will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

In certain embodiments, compounds or compositions in accordance with the present invention may be administered at dosage levels sufficient to deliver from about 0.0001 mg/kg to about 100 mg/kg, from about 0.01 mg/kg to about 50 mg/kg, from about 0.1 mg/kg to about 40 mg/kg, from about 0.5 mg/kg to about 20 mg/kg, 0.5 mg/kg to about 30 mg/kg, from about 0.01 mg/kg to about 10 mg/kg, from about 0.1 mg/kg to about 10 mg/kg, from about 2.5 mg/kg to about 5.0 mg/kg, or from about 1 mg/kg to about 25 mg/kg, of subject body weight per day, one or more times a day, to obtain the desired therapeutic, diagnostic, prophylactic, or imaging effect. The desired dosage may be delivered three times a day, two times a day, once a day, every other day, every third day, every week, every two weeks, every three weeks, or every four weeks. In certain embodiments, the desired dosage may be delivered using multiple administrations (e.g., two, three, four, five, six, seven, eight, nine, ten, eleven, twelve, thirteen, fourteen, or more administrations).

According to the present invention, compounds or compositions of the present disclosure may be administered in split-dose regimens. As used herein, a "split dose" is the division of single unit dose or total daily dose into two or more doses, e.g., two or more administrations of the single unit dose. As used herein, a "single unit dose" is a dose of any therapeutic administered in one dose/at one time/single route/single point of contact, i.e., single administration event. As used herein, a "total daily dose" is an amount given or prescribed in a 24 hr period. It may be administered as a single unit dose. In one embodiment compounds or compositions of the present disclosure are administered to a subject in split doses. Compounds or compositions of the present disclosure may be formulated in buffer only or in a formulation described herein. Pharmaceutical compositions of the present invention as described herein may be formulated into a dosage form described herein, such as a topical, intranasal, intratracheal, or injectable (e.g., intravenous, intraocular, intravitreal, intramuscular, intracardiac, intraperitoneal or subcutaneous). General considerations in the formulation and/or manufacture of pharmaceutical agents may be found, for example, in Remington: The Science and Practice of Pharmacy $21^{st}$ ed., Lippincott Williams & Wilkins, 2005 (incorporated herein by reference).

In some embodiments, dosage of the compositions of the present disclosure may be adjusted to reduce bystander effects. As used herein the "bystander effect" refers to any negative effects on non-target cells or cells neighboring target cells (also referred to herein as bystander cells). According to such methods, doses or conjugate types may be adjusted to reduce bystander effects. Such adjustments may lead to the treatments with greater than 95%, greater than 90%, greater than 85%, greater than 80%, greater than 75%, greater than 70%, greater than 65%, greater than 60%, greater than 55%, greater than 50%, greater than 45%, greater than 40%, greater than 35%, greater than 30%, or greater than 25% of bystander cells remaining viable.

Coatings or Shells

Solid dosage forms of tablets, dragees, capsules, pills, and granules can be prepared with coatings and shells such as enteric coatings and other coatings well known in the pharmaceutical formulating art. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type may be employed as fillers in soft and hard-filled gelatin capsules using such excipients as lactose or milk sugar as well as high molecular weight polyethylene glycols and the like.

Combinations

In some embodiments, compounds or compositions of the present disclosure may be used in combination with one or more other therapeutic, prophylactic, diagnostic, or imaging agents. By "in combination with," it is not intended to imply that the agents must be administered at the same time and/or formulated for delivery together, although these methods of delivery are within the scope of the present disclosure. Compounds or compositions can be administered concurrently with, prior to, or subsequent to, one or more other desired therapeutics or medical procedures. In general, each agent will be administered at a dose and/or on a time schedule determined for that agent. In some embodiments, the present disclosure encompasses the delivery of pharmaceutical, prophylactic, diagnostic, and/or imaging compositions in combination with agents that may improve their bioavailability, reduce and/or modify their metabolism, inhibit their excretion, and/or modify their distribution within the body.

Measurements
Bioavailability

Compounds and compositions of the invention, when formulated into a composition with a delivery/formulation agent or vehicle as described herein, can exhibit an increase in bioavailability as compared to a composition lacking a delivery agent as described herein. As used herein, the term "bioavailability" refers to the systemic availability of a given amount of the compounds and compositions of the invention, administered to a mammal. Bioavailability can be assessed by measuring the area under the curve (AUC) or the maximum serum or plasma concentration ($C_{max}$) of the unchanged form of a compound following administration of the compound to a mammal. AUC is a determination of the area under the curve plotting the serum or plasma concentration of a compound along the ordinate (Y-axis) against time along the abscissa (X-axis). Generally, the AUC for a particular compound can be calculated using methods known to those of ordinary skill in the art and as described in G. S. Banker, Modern Pharmaceutics, Drugs and the Pharmaceutical Sciences, v. 72, Marcel Dekker, New York, Inc., 1996, herein incorporated by reference.

The $C_{max}$ value is the maximum concentration of the compound achieved in the serum or plasma of a mammal following administration of the compound to the mammal. The $C_{max}$ value of a particular compound can be measured using methods known to those of ordinary skill in the art. The phrases "increasing bioavailability" or "improving the pharmacokinetics," as used herein mean that the systemic availability of the compounds and compositions of the invention, measured as AUC, $C_{max}$, or $C_{min}$ in a mammal is greater, when co-administered with a delivery agent as described herein, than when such co-administration does not take place. In some embodiments, the bioavailability of the compounds and compositions of the invention can increase by at least about 2%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100%.

Therapeutic Window

Compounds and compositions of the invention, when formulated into a composition with a delivery agent as described herein, can exhibit an increase in the therapeutic window of the administered compounds and compositions of the invention as compared to the therapeutic window of the administered compounds and compositions of the invention lacking a delivery agent as described herein. As used herein "therapeutic window" refers to the range of plasma concentrations, or the range of levels of therapeutically active substance at the site of action, with a high probability of eliciting a therapeutic effect. In some embodiments, the therapeutic window of the compounds and compositions of the invention when co-administered with a delivery agent as described herein can increase by at least about 2%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100%.

In some embodiments, compounds and compositions of the invention are detectable in subject samples for at least 2 days, at least 5 days, at least 10 days, at least 2 weeks, at least 4 weeks, at least 2 months, at least 6 months, or at least a year after administration.

Volume of Distribution

Compounds and compositions of the invention, when formulated into a composition with a delivery agent as described herein, can exhibit an improved volume of distribution ($V_{dist}$), e.g., reduced or targeted, relative to a composition lacking a delivery agent as described herein. The volume of distribution ($V_{dist}$) relates the amount of the drug in the body to the concentration of the drug in the blood or plasma. As used herein, the term "volume of distribution" refers to the fluid volume that would be required to contain the total amount of the drug in the body at the same concentration as in the blood or plasma: $V_{dist}$ equals the amount of drug in the body/concentration of drug in blood or plasma. For example, for a 10 mg dose and a plasma concentration of 10 mg/L, the volume of distribution would be 1 liter. The volume of distribution reflects the extent to which the drug is present in the extravascular tissue. A large volume of distribution reflects the tendency of a compound to bind to the tissue components compared with plasma protein binding. In a clinical setting, $V_{dist}$ can be used to determine a loading dose to achieve a steady state concentration. In some embodiments, co-administration with a delivery agent may be used to modulate the volume of distribution of compounds and/or compositions of the present disclosure. For example, the volume of distribution may be decreased by at least about 2%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, or at least about 70%.

In some embodiments, compounds and compositions of the invention comprise compositions and/or complexes in combination with one or more pharmaceutically acceptable excipients. Pharmaceutical compositions may optionally comprise one or more additional active substances, e.g. therapeutically and/or prophylactically active substances. General considerations in the formulation and/or manufacture of pharmaceutical agents may be found, for example, in *Remington: The Science and Practice of Pharmacy* $21^{st}$ ed., Lippincott Williams & Wilkins, 2005 (incorporated herein by reference).

In some embodiments, compositions are administered to humans, human patients or subjects. For the purposes of the present disclosure, the phrase "active ingredient" generally refers to compounds and compositions of the invention to be delivered as described herein.

Although the descriptions of pharmaceutical compositions provided herein are principally directed to pharmaceutical compositions which are suitable for administration to humans, it will be understood by the skilled artisan that such compositions are generally suitable for administration to any other animal. e.g., to non-human animals, e.g. non-human mammals. Modification of pharmaceutical compositions suitable for administration to humans in order to render the compositions suitable for administration to various animals is well understood, and the ordinarily skilled veterinary pharmacologist can design and/or perform such modification with merely ordinary, if any, experimentation. Subjects to which administration of the pharmaceutical compositions is contemplated include, but are not limited to, humans and/or other primates; mammals, including commercially relevant mammals such as cattle, pigs, horses, sheep, cats, dogs, mice, and/or rats; and/or birds, including commercially relevant birds such as poultry, chickens, ducks, geese, and/or turkeys.

Formulations of the pharmaceutical compositions described herein may be prepared by any method known or hereafter developed in the art of pharmacology. In general, such preparatory methods include the step of bringing the active ingredient into association with an excipient and/or one or more other accessory ingredients, and then, if necessary and/or desirable, dividing, shaping and/or packaging the product into a desired single- or multi-dose unit.

A pharmaceutical composition in accordance with the invention may be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition in accordance with the invention will vary, depending upon the identity, size, and/or condition of the subject treated and further depending upon the route by which the composition is to be administered. By way of example, the composition may comprise between 0.1% and 100%, e.g., between 0.5 and 50%, between 1-30%, between 5-80%, or at least 80% (w/w) active ingredient. In one embodiment, active ingredients are antibodies directed toward cancer cells.

Diagnostic and Monitoring Applications

In some embodiments, the present disclosure provides methods of detecting GCD59 that include obtaining a subject sample; applying the subject sample to a substrate having a CD59 capture antibody; applying an Amadori-modified GCD59 detection antibody; and detecting the Amadori-modified GCD59 detection antibody. The subject sample may include, but is not limited to one or more of a cell, a tissue, a tissue section, and a body fluid, e.g., urine, blood, sweat, serum, plasma, and saliva.

According to some methods, samples are used without pretreatment. In some cases, samples may be diluted prior to analysis. Such dilutions may be at least 10:1, at least 5:1, at least 2:1, at least 1:1, at least 1:10, at least 1:100, at least 1:1.000, at least 1:10,000, at least 1:100,000, at least 1:1,000,000, at least 1:109, at least $1:10^{12}$, or at least $1:10^{15}$. In some cases, samples are diluted from about 1:200 to about 1:300. In some cases, samples are treated with reducing agents, oxidizing agents, dithiothreitol (DTT), and/or beta-mercaptoethanol (BME) prior to analysis.

As used herein, the term "reducing agent" refers to any electron donor chemical or compound involved in or used for oxidation-reduction reactions. In some embodiments, reducing agents are selected from sodium borohydride ($NaBH_4$) and sodium cyanoborohydride ($NaCNBH_3$). Sample pretreatment with reducing agents may be conducted to modify glycated side chain structure, e.g., for detection agent recognition of GCD59 with reduced K41. $NaCNBH_3$ treatment reduces Schiff's base glycated K41 to glucitollysine. $NaBH_4$ treatment reduces both Schiff's base glycated K41 and Amadori-modified glycated K41 to glucitollysine.

Reducing agents may be used alone or in solution (referred to herein as "reducing agent solution"). Reducing agent solutions may include any of a variety of solvents. In some embodiments, reducing agent solutions include water. In some embodiments, reducing agent solutions include organic solvents. Organic solvents are solvents that include carbon-based components. In some embodiments, organic solvents may include, but are not limited to, 1,1-dichloroethane, 1,2-dichloroethane, 1,2-dimethoxy-ethane, 1-butanol, 1-heptanol, 1-hexanol, 1-octanol, 1-pentanol, 1-propanol, 2-aminoethanol, 2-butanol, 2-butanone, bis(2-methoxyethyl) ether, 2-pentanol, 2-pentanone, 2-propanol, 3-pentanol, 3-pentanone, acetic acid, acetone, acetonitrile, acetyl acetone, aniline, anisole, benzene, benzonitrile, benzyl alcohol, carbon disulfide, carbon tetrachloride, chlorobenzene, chloroform, cyclohexane, cyclohexanol, cyclohexanone, diethyl ether, diethylamine, diethylene glycol, diglyme, dimethoxyethane (glyme), dimethyl sulfoxide (DMSO), dimethylether, N,N-dimethylformamide (DMF), N,N-dimethyl-acetamide, dimethylphthalate, dimethylsulfoxide (DMSO), di-n-butylphthalate, dioxane, ethanol, ether, ethyl acetate, ethyl acetoacetate, ethyl benzoate, ethylene glycol, glycerin, heptane, 2-ethylhexanol, Hexamethylphosphoramide, Hexamethylphosphorous triamide (HMPT), hexane, i-butanol, methanol, methyl acetate, methyl t-butyl ether (MTBE), methylene chloride, N,N-dimethylaniline, nitromethane, N-methyl-2-pyrrolidinone, pentane, Petroleum ether (ligroine), pyridine, t-butyl alcohol, tetraglyme, tetrahydrofuran (THF), toluene, triethyl amine, nitromethane and triethylene glycol dimethyl ether. In some embodiments, reducing agent solutions may comprise triethylene glycol dimethyl ether, bis(2-methoxyethyl) ether and/or tetraglyme solvents.

Reducing agent solutions with organic solvents may include $NaBH_4$ solutions. Such solutions may include or be prepared from commercially available preparations (for example, from Sigma-Aldrich, St. Louis, Mo.). Such commercial preparations may include, but are not limited to, 99% Sodium Borohydride Solution 0.5 M in bis(2-methoxyethyl) ether; 99° % Sodium Borohydride Solution 3 M in tetraglyme ether; 99% Sodium Borohydride Solution 2.0 M in triethylene glycol dimethyl ether; 99.5% Sodium Borohydride Solution 0.5 M in bis(2-methoxyethyl) ether; 99.5% Sodium Borohydride Solution 3 M in tetraglyme ether; 99.5% Sodium Borohydride Solution 2.0 M in triethylene glycol dimethyl ether; 99.9% Sodium Borohydride Solution 3 M in tetraglyme ether; 99.9% Sodium Borohydride Solution 2.0 M in triethylene glycol dimethyl ether; 99.95% Sodium Borohydride Solution 0.5 M in bis(2-methoxyethyl) ether; 99.95% Sodium Borohydride Solution 3 M in tetraglyme ether; 99.95% Sodium Borohydride Solution 2.0 M in triethylene glycol dimethyl ether; 99.99% Sodium Borohydride Solution 0.5 M in bis(2-methoxyethyl) ether; 99.99% Sodium Borohydride Solution 3 M in tetraglyme ether; 99.99% Sodium Borohydride Solution 2.0 M in triethylene glycol dimethyl ether; 99.999% Sodium Borohydride Solution 0.5 M in bis(2-methoxyethyl) ether; 99.999% Sodium Borohydride Solution 3 M in tetraglyme ether; 99.999% Sodium Borohydride Solution 2.0 M in triethylene glycol dimethyl ether; and 99.9% Sodium Borohydride Solution 0.5 M in bis(2-methoxyethyl) ether.

Reducing agent solutions may include reducing agent concentrations of from about 0.1 M to about 10 M. In some embodiments, stock solutions of reducing agent solutions are used that require dilution prior to use. Reducing agent stock solutions may include greater than 1 M reducing agent concentrations (e.g., from about 1.1 to about 1.5 M, from about 1.2 M to about 2 M, from about 1.7 M to about 3 M, from about 2.5 M to about 4 M, from about 3.5 M to about 5 M, from about 4.5 M to about 8 M, or from about 6 M to about 10 M). Reducing agent stock solutions may be diluted to from about 0.5 M to about 1 M reducing agent concentrations prior to sample treatment. Dilution may be carried out using aqueous and/or organic solvents.

In some embodiments, the anti-Amadori-modified GCD59 detection antibodies used in methods of the disclosure may include detectable labels. Such detectable labels may include, but are not limited to biotin, streptavidin, avidin, fluorescent labels, enzymatic labels, luminescent labels, and radioactive labels. In some methods, anti-Amadori-modified GCD59 detection antibodies may be detected using a secondary antibody.

In some embodiments, 1 M reducing agent solutions may be combined with subject samples at a ratio of from about 1:1 (sample:reducing agent solution) to about 1:1000. For example, the ratio may be 1:5, 1:10, 1:20, 1:100 or 1:500. Samples may be incubated with reducing agent solution for from about 20 minutes to about 2 hours, from about 1 hour to about 4 hours, from about 3 hours to about 24 hours, from about 12 hours to about 3 days, from about 2 days to about 5 days, or for at least 5 days to allow sample reduction to occur.

According to some methods of the disclosure, microtiter plates are used.

In some embodiments, methods of the disclosure may be used for monitoring, detecting, and/or screening for diabetes in subjects. In some embodiments, methods of the disclosure may be used for assessing and/or stratifying risk in diabetic subjects. Some methods may be used as part of a companion diagnostic for diabetes-related indications.

In some embodiments, methods of the disclosure may be used for drug development. Such embodiments may include testing and/or developing therapeutics for diabetes-related indications. In some cases, methods of the disclosure may be used to conduct clinical trials.

In some embodiments, methods of the disclosure include remote monitoring of subjects. Such methods may incorporate all or part of other methods taught herein.

In some embodiments, methods of the present disclosure include methods of assessing GCD59 for the presence of at least one N-glycosylation. CD59 in an N-glycosylated membrane GPI-anchored protein that is a primary regulator of complement activation. Multiple glycosylation enzymatic routes lead to the formation of mature carbohydrate units on proteins and these modifications may be cell and/or tissue specific. Assessing samples for CD59 N-glycosylation may be used to identify organs and/or tissues that are most affected by CD59 glycation at residue K41. In some cases, CD59 may be N-glycosylated on residue N18. In some embodiments plasma, serum, and/or urine may be assessed to identify the organ/tissue most affected by glycation and therefore most susceptible for vascular complications of diabetes. For example, detection of kidney-specific N-glycosylated GCD59, the predominant form of GCD59 in blood and urine samples of pre-diabetic or diabetic patients, may indicate patient susceptibility for development of diabetes nephropathy. In some cases, this detection may be carried out before the onset of actual kidney damage that may otherwise go undetected with current diagnostic methods. Such early detection may be used to raise patient awareness and indicate the need for life style changes. In some cases, early detection may direct a physician to initiate early preventive therapeutic intervention.

In some embodiments, the present disclosure provides methods of assessing GCD59 that include the steps of isolating GCD59 with an antibody capable of binding K41 Amadori-modified GCD59 and detecting at least one N-glycosylation present on GCD59 (e.g., N-glycosylation on residue N18 of GCD59).

Methods of the present disclosure may include methods of identifying at least one of: (1) predisposition to an organ specific complication of diabetes; (2) pre-clinical diabetic peripheral neuropathy; (3) pre-clinical diabetic nephropathy; (4) pre-clinical diabetic retinopathy; and (5) pre-clinical diabetic vascular disease. Such methods may include the steps of: (1) isolating GCD59 with an antibody specific for K41 Amadori-modified GCD59 and (2) detecting at least one N-glycosylation present on GCD59 (e.g., N-glycosylation on residue N18 of GCD59).

Detection of GCD59 N-glycosylation may be carried out by any methods known in the art. In some cases, GCD59 N-glycosylation is detected using immunological methods. In other embodiments, GCD59 N-glycosylation may be detected using mass spectrometry.

Point of Care Testing

Kits and methods (including all or part of such methods) disclosed may be formatted for point of care use. In some embodiments, point of care use may include the use of one or more patient monitoring device. Such devices that may include a device capable of receiving and/or transmitting an electronic signal. In some cases, patient monitoring devices may be or be combined with smart devices (e.g., a smart phone or smart watch).

CD59 Glycation Inhibition

In some embodiments, the present disclosure provides CD59 glycation inhibitors and methods of developing such inhibitors. Human CD59 is a major complement regulator and its normal function may be reduced or blocked by glycation which can occur under hyperglycemic conditions, hCD59 contains a putative glycation motif that includes residues K41 and H44. These residues fall within the proximity of W40 considered to be an integral part of the active site of the protein. Glycation of K41 requires H44 to provide acid-base catalysis for the chemical reaction between glucose and the epsilon amino group of K41. Glycation of hCD59 at K41 may increase the risk of developing diabetes-related complications, including, but not limited to vascular diabetes.

Methods of the present disclosure may include methods of inhibiting CD59 glycation. According to some such methods, agents may be administered that target CD59 and block K41 glycation. Such agents may target, for example, H44 of human CD59 and block glycation of K41. In some embodiments, anti-Amadori-modified GCD59 antibodies may be used in screening procedures to identify agents targeting CD59 and blocking K41 glycation.

Methods of the present disclosure may include methods of developing inhibitors of hCD59 K41 glycation. Such methods may include the use of one or more antibodies capable of binding K41-glycated CD59, including, but not limited to any of the anti-K41 Amadori-modified hCD59 antibodies described herein. In some embodiments, such methods include the steps of: (1) contacting a sample with at least one test compound, wherein the sample includes hCD59 (purified or recombinant) and conditions suitable for K41 glycation and (2) evaluating the level of K41-glycated hCD59 in the sample using a GCD59 detection antibody. The evaluation may be carried out according to any of the methods described herein or previously in any of U.S. Pat. Nos. 6,835,545; 7,049,082; 7,439,330; 9,068,006; 9,417,248; and U.S. Publication No. US2016/0299150, the contents of each of which are herein incorporated by reference in their entirety. Such methods may include the use of a standard agent, including, but not limited to a GCD59 surrogate compound. Where test compounds are capable of inhibiting hCD59 K41 glycation, the level of GCD59 detected will be reduced. Test compounds may include, but are not limited to small molecules, peptides, synthetic constructs, fusion proteins, aptamers, nucleic acids, and antibodies.

III. Kits

In some embodiments, the present disclosure provides kits for determining the concentration of GCD59 in a subject sample. Such kits may include one or more of (1) a capture antibody, (2) a detection antibody, and (3) instructions for use. Some kits include compounds for the generation of a standard curve. Such compounds may include standard agents (e.g., surrogate compounds). In some embodiments, surrogate compounds may include any of those disclosed in U.S. Pat. No. 9,417,248 (e.g., the surrogate compound presented in FIG. 27, therein) or U.S. Publication No. US2016/0299150, the contents of each of which are herein incorporated by reference in their entirety. In some cases, kits include at least one buffer. Such buffers may be used to contact subject samples. Buffers may include reducing agents, oxidizing agents, dithiothreitol (DTT), and/or beta-mercaptoethanol (BME). Reducing agents may be provided as part of a reducing agent solution. Reducing agent solutions may include water and/or organic solvent. The organic solvent may include bis(2-methoxyethyl) ether.

Kits of the disclosure may be used for detecting the presence, level, and/or changes in GCD59 levels. Such kits may include one or more capture antibody to capture CD59 and/or GCD59. Capture antibodies may include any of the antibodies described herein (e.g., antibody H9, encoded by SEQ ID NOs: 9 and 10). Additional kits may include one or more detection antibody to detect GCD59 and/or CD59. Detection antibodies may include any antibodies described herein (e.g., antibodies D2 or D3, encoded by SEQ ID NOs: 6 and 7 for D2 or SEQ ID NOs: 6 and 8 for D3). In some embodiments, kits may include other antibodies known in the art for capturing or detecting CD59 and/or GCD59. Such antibodies may include any of those described and/or claimed in European Patent Number EP2348050, International Publication Number WO2015084994, and U.S. Pat. Nos. 9,068,006, 9,417,248, the contents of each of which are herein incorporated by reference in their entireties.

Kits of the disclosure may include one or more internal controls. Such internal controls may include plasma assay controls and/or controls based on any other bodily fluids. Some kits include one or more of an assay diluent, a conjugate diluent, and a wash buffer. Kit reagents may be lyophilized.

In some embodiments, kits may be used to determine the presence, absence, or quantity of glycosylated protein epitope. Such glycosylated protein epitopes may include glycosylated CD59 epitopes. In some cases, N-glycosylated CD59 and/or GCD59 may be detected. Such kits may be used, for example, to detect cell and/or tissue-specific N-glycosylated epitopes.

Kits may include any of those described and/or claimed in European Patent Number EP2348050, International Publication Number WO2015084994, and U.S. Pat. Nos. 9,068, 006, 9,417,248, the contents of each of which are herein incorporated by reference in their entireties. Such kits may have one or more antibody described herein as a substitute for one or more of the antibodies described in such kits. In some cases, such kits may include an anti-Amadori-modified GCD59 antibody described herein in place of a detection antibody described therein. These kits may be assembled without a reducing agent and may be used for detection and/or quantitation of GCD59 in samples without the need for carrying out a sample reducing step.

IV. Devices

Kits and methods (including all or part of such methods) disclosed may be formatted for use with a device. In some embodiments, device may include a wearable device. Such devices may, for example, be in the form of a watch and/or include a wristband.

Compounds, compositions, methods, kits, and reagents described herein may, in some embodiments, be used with or may be improvements of those described in International Publication Number WO2015084994, the contents of which are herein incorporated by reference in their entirety.

V. Definitions

As used herein, the term "receiver operating characteristic curve" or "ROC curve," refers to a statistical tool that generates a graphical plot to illustrate the performance of a binary classifier system as its discrimination cut-off (threshold) is varied. An ROC curve may serve as a tool for diagnostic test evaluation and may be used to quantify how accurately a medical diagnostic test can discriminate between two patient states. In one example, a ROC curve may be used to demonstrate a tradeoff between sensitivity and specificity in an analysis. Analysis of an ROC curve, employing familiar statistical methods, may be used to identify an optimal diagnostic cut-off for the level of a biomarker. The optimal diagnostic cut-off value may then be used to make a medical decision.

As used herein, the term "threshold value" refers to a value used to divide continuous results into categories (e.g., positive and negative) for purposes of characterizing an agent used to generate the results, to determine the placement of an agent into one or more such categories, or to segregate subjects into categories based on a corresponding value (falling within the range of continuous results) associated with one or more such subjects. In some embodiments, a threshold value may be a level of a biomarker or other indicator used to categorize one or more subjects with biomarker or other indicator levels falling above, falling below, or equal to the threshold value. For example, a threshold value may be a concentration of a factor present in a subject or subject sample that is used to divide subjects into disease categories. Where the threshold value is a level of GCD59 in a subject, the threshold value may be used to assign subjects into diabetic or non-diabetic categories based on whether GCD59 levels in such subjects fall above or below the threshold value, respectively. In some cases, a threshold value may be used to make a medical decision based on whether values associated with one or more patients fall above, fall below, or are equal to the threshold value. In some embodiments, a diagnostic threshold value (also referred to as a "cut-off point") for a biomarker that yields continuous real values may be used to delineate tests positives and test negatives. For example, a training set of blood plasma samples may be used to generate a Receiver Operating Characteristic (ROC) curve that is a plot of the true positive rate against the false positive rate for different possible cut-off points. Analysis of the ROC curve, employing familiar statistical methods that are known to those familiar with the art, may lead to the identification of an optimal diagnostic cut-off for a biomarker. The optimal diagnostic cut-off value may be used to arrive at a medical decision.

VI. Equivalents and Scope

Those skilled in the art will recognize, or be able to ascertain using no more than routine experimentation, many equivalents to the specific embodiments in accordance with the invention described herein. The scope of the present invention is not intended to be limited to the above Description, but rather is as set forth in the appended claims.

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or the entire group members are present in, employed in, or otherwise relevant to a given product or process.

It is also noted that the term "comprising" is intended to be open and permits but does not require the inclusion of additional elements or steps. When the term "comprising" is used herein, the term "consisting of" is thus also encompassed and disclosed.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the invention (e.g., any nucleic acid or protein encoded thereby; any method of production; any method of use; etc.) can be excluded from any one or more claims, for any reason, whether or not related to the existence of prior art.

All cited sources, for example, references, publications, databases, database entries, and art cited herein, are incorporated into this application by reference, even if not expressly stated in the citation. In case of conflicting statements of a cited source and the instant application, the statement in the instant application shall control. Section and table headings are not intended to be limiting.

EXAMPLES

Example 1. Antibody Preparation and Sequencing

Antibodies to CD59 and K41 Amadori-modified GCD59 were each generated using CD59 fragments. For anti-K41 Amadori-modified GCD59 antibody preparation, CD59 fragments having Amadori-modified K41 were used. Antibodies were prepared by mouse immunization and development of hybridoma cells from animals exhibiting successful expression of antibodies with high affinity and specificity. Clone H9 was developed as a capture antibody, binding to both glycated and non-glycated CD59. Clones D2 and D3 were developed as detection antibodies, binding to K41 Amadori-modified GCD59. Antibodies were sequenced and analyzed to identify antibody regions. Resulting sequences are provided in Tables 1-7. Antibodies D2 and D3 were found to have heavy and light chains with identical amino acid sequences, but with heavy chain nucleotide sequences differing by a single nucleotide.

Example 2. GCD59 Detection in a Urine Sample

GCD59 detection in urine samples was carried out using detection antibody D2, described above, specific for Amadori-modified GCD59. Assay plates were first coated with CD59 capture antibody. H9. Urine samples were obtained from two subjects, one known to have a high level of HbA1C (HbA1C-H) and one known to have a low level of HbA1C (HbAC1-L). High levels of HbA1C are a known indicator of elevated blood glucose. Samples were prepared by first adding beta-mercaptoethanol (BME) to a final concentration of 5%. Samples were then boiled at 100° C. for 5 min and centrifuged to pellet any debris. Supernatants were then isolated for the assay. A surrogate compound standard, as shown in FIG. 27 of U.S. Pat. No. 9,417,248, was used to prepare a dilution series for generating a calibration curve. The Amadori-modified GCD59 surrogate included synthetic compounds including capture and detection peptides linked by a flexible linker.

Standard samples, urine samples, as well as control samples [serum dilution buffer (50 mM Acetic acid/Na acetate; 2% NonIdet P40 Substitute; 0.15% Tween 20; 0.1% Triton X-100; 50 ppm ProClin 300) only] were added to the assay plate in triplicate. Urine samples were further diluted using serum dilution buffer to create a series of conditions ranging from 6% v/v urine sample to 0.2% urine sample in serum dilution buffer. Assay plates were placed on a shaker for one hour at room temperature. Plates were then washed with wash buffer [phosphate buffered saline (PBS) with 0.05% TWEEN®-20] before the addition of 100 µl of antibody D2 solution [1.25 µg/ml in PBS with 10% protein-free blocking buffer (Thermo Fisher, Waltham, Mass.)]. Plates were then incubated for 2 hours at room temperature with shaking.

After two hours, plates were washed with wash buffer and incubated with 100 µl of secondary antibody conjugated with horse radish peroxidase (HRP) and incubated for 1 hour at room temperature with shaking in presence of TMB substrate reagents A and B. Plates were quenched by treatment with $H_2SO_4$ solution to generate the colorimetric end product. Wells were then examined spectrophotometrically to obtain optical density values at 450 nm.

A calibration curve (FIG. 1A) was generated based on wells using the surrogate compound standard. Results from urine samples were converted into standard protein units (SPU) based on the calibration curve and plotted against percent urine values from each of the samples (FIG. 1B). Values obtained from HbAC1-H samples indicated concentration dependent antibody D2 binding with around 2.5 SPU in high concentration samples. HbAC1-L sample values were low indicating little to no binding of antibody D2. These results demonstrate the ability of H9 to capture CD59 and D2 to detect Amadori-modified GCD59 in fluid samples in a concentration-dependent manner.

Example 3. GCD59 Detection by Western Blot

Figure 2:
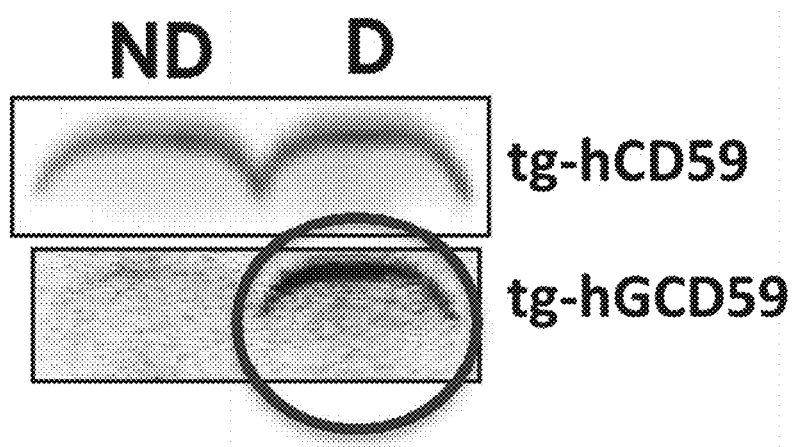
FIG. 2 is an image from Western blot analysis showing detection of Amadori-modified hGCD59 with antibody D2.

The specificity of anti-Amadori-modified hGCD59 mAb D2 and D3 to glycated hCD59 was tested in cell lysates derived from diabetic transgenic mice expressing hCD59 transgene (Tg) in red blood corpuscles (RBCs). Diabetes was induced in the hCD59 transgenic mice by administering one dose of Streptozotein (STZ) and blood glucose was measured after two weeks. A mouse was considered diabetic if its blood sugar level was greater than 200 mg/dL. RBCs were obtained from diabetic transgenic mice (D) and control non-diabetic mice (ND), lysed and proteins were extracted. The protein samples were separated using SDS-PAGE (Sodium Dodecyl sulfate-Polyacrylamide gel electrophoresis) and immunoblotted with anti-Amadori modified hGCD59 antibody (D2) and anti hCD59 antibody (FIG. 2). Consistent with the elevation of glycated CD59 in diabetes, the anti-Amadori modified hGCD59 antibody showed an intense band in the diabetic mice and only a faint band in the control non-diabetic mice. Both the diabetic and control non-diabetic mice showed similar levels of hCD59, demonstrating the specificity of the anti-Amadori modified hGCD59 antibody.

Example 4. ELISA Kit

A sandwich-type ELISA assay is prepared that specifically quantifies GCD59 relative to the glycated CD59 (GCD59) peptide hybrid surrogate. Antibody H9 is used as a capture antibody to capture CD59 in samples tested. The detection antibody is developed using a peptide antigen containing a glucitollysine residue in the equivalent position of K41 in CD59. For this reason, these assays detect the reduced form of GCD59. These anti-glucitollysine GCD59 ELISA kit assays also include a sample preparation step that utilizes $NaBH_4$ as the reducing agent for transformation of the glycated form of GCD59 into the reduced glycated form of GCD59. Kits include solutions of reducing agent in organic solvent to carry out this step.

Sandwich-type Amadori-modified GCD59 ELISA assays do not need sample preparation by $NaBH_4$ reduction due to detection antibody specificity for the non-reduced Amadori-modified form of GCD59. Sample treatment with DTT may, however, improve antibody affinity.

Example 5. Point of Care Testing

Kits and methods disclosed are formatted for use with point of care testing. This includes formatting for use with patient monitoring devices and devices that can be combined with smart devices (e.g., a smart phone).

Example 6. Wearable Devices

Kits and methods disclosed are formatted for use with a wearable device in the form of a watch or other band which may be worn around the wrist, finger, neck or limb.

---

The invention claimed is:

1. An antibody comprising a heavy chain variable domain (VH) and a light chain variable domain (VL), wherein:
   the VH comprises:
   i. a CDR-H1 having an amino acid sequence of SEQ ID NO: 39;
   ii. a CDR-H2 having an amino acid sequence of SEQ ID NO: 41; and
   iii. a CDR-H3 having an amino acid sequence of SEQ ID NO: 43; and
   the VL comprises:
   i. a CDR-L1 having an amino acid sequence of SEQ ID NO: 34;
   ii. a CDR-L2 having an amino acid sequence of SEQ ID NO: 35; and
   iii. a CDR-L3 having an amino acid sequence of SEQ ID NO: 37.

2. The antibody of claim 1, wherein the VH comprises an amino acid sequence having at least 95% sequence identity to an amino acid sequence of SEQ ID NO: 32 and wherein the VL comprises an amino acid sequence that is at least 95% identical to an amino acid sequence of SEQ ID NO: 31.

3. The antibody of claim 2 comprising a heavy chain with an amino acid sequence having at least 95% sequence identity to SEQ ID NO: 5.

4. The antibody of claim 3, wherein said heavy chain is encoded by a nucleotide sequence of SEQ ID NO: 10.

5. The antibody of claim 2 comprising a light chain with an amino acid sequence having at least 95% sequence identity to SEQ ID NO: 4.

6. The antibody of claim 5, wherein said light chain is encoded by a nucleotide sequence of SEQ ID NO: 9.

7. The antibody of claim 1, wherein said antibody binds to CD59.

8. The antibody of claim 7, wherein said antibody binds to a non-glycated epitope of CD59.

9. The antibody of claim 7, wherein said antibody binds to an epitope of CD59 that does not include lysine 41 (1(41).

10. The antibody of claim 1, wherein said antibody binds to a glycated epitope of glycated CD59 (GCD59).

11. A kit comprising:
   a capture agent, wherein the capture agent comprises the antibody of claim 1; and
   instructions for use of said kit.

12. The kit of claim 11 comprising a detection agent, wherein said detection agent is selected from a lectin and a detection antibody, the detection antibody comprising a VH and VL, wherein the VH comprises an amino acid sequence according to SEQ ID NO: 30, and wherein the VL comprises an amino acid sequence according to SEQ ID NO: 29.

13. A method of detecting a target protein in a sample, wherein said target protein comprises GCD59, said method comprising:
   i. obtaining said sample;
   ii. applying said sample to a substrate, said substrate comprising a capture antibody, wherein said capture antibody is selected from at least one of an antibody binding to an N-glycated epitope of CD59, the antibody of claim 9, and the antibody of claim 9;
   iii. applying a detection antibody to said substrate-sample complex, wherein said detection antibody binds to a target epitope, said target epitope comprising a glycated or non-glycated epitope of GCD59; and
   iv. analyzing said substrate-sample complex for the presence of said detection antibody.

14. The method of claim 13, wherein the detection antibody comprises a detectable label.

15. The method of claim 14, wherein the detectable label is selected from the group consisting of biotin, streptavidin, avidin, a fluorescent label, an enzymatic label, a luminescent label, and a radioactive label.

16. The method of any of claim 13, wherein said substrate is selected from at least one of an assay plate, a bead, a membrane, a conducting surface, and a conducting nanoparticle.

* * * * *